(12) United States Patent
Soneda et al.

(10) Patent No.: US 10,968,169 B2
(45) Date of Patent: Apr. 6, 2021

(54) UREA DERIVATIVE

(71) Applicant: Daiichi Sankyo Company, Limited, Tokyo (JP)

(72) Inventors: Tsuyoshi Soneda, Chuo-ku (JP); Yuji Nakamura, Chuo-ku (JP); Koji Matsumoto, Chuo-ku (JP); Naomi Tanaka, Chuo-ku (JP); Taichi Fukunaga, Chuo-ku (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 16/339,305

(22) PCT Filed: Oct. 5, 2017

(86) PCT No.: PCT/JP2017/036272
§ 371 (c)(1),
(2) Date: Apr. 3, 2019

(87) PCT Pub. No.: WO2018/066646
PCT Pub. Date: Apr. 12, 2018

(65) Prior Publication Data
US 2020/0017439 A1 Jan. 16, 2020

(30) Foreign Application Priority Data
Oct. 6, 2016 (JP) .............. JP2016-197867

(51) Int. Cl.
*C07C 275/42* (2006.01)
*C07C 323/44* (2006.01)
*C07D 207/10* (2006.01)
*C07D 211/06* (2006.01)
*C07D 333/36* (2006.01)

(52) U.S. Cl.
CPC .......... *C07C 275/42* (2013.01); *C07C 323/44* (2013.01); *C07D 207/10* (2013.01); *C07D 211/06* (2013.01); *C07D 333/36* (2013.01); *C07B 2200/13* (2013.01)

(58) Field of Classification Search
CPC ................................. C07C 275/42
USPC ....................................... 514/331
See application file for complete search history.

(56) References Cited

U.S. PATENT DOCUMENTS

| 4,944,791 A | 7/1990 | Schröder et al. |
| 7,504,106 B2 | 3/2009 | Skurkovich et al. |
| 2013/0123496 A1 | 5/2013 | Beard et al. |
| 2014/0256685 A1 | 9/2014 | Beard et al. |

FOREIGN PATENT DOCUMENTS

| CA | 2 730 599 C | 9/2016 |
| JP | 58-188864 A | 11/1983 |
| JP | 11-209303 A | 8/1999 |
| JP | 2015-502924 A | 1/2015 |
| JP | 2016069495 A | 5/2016 |
| WO | 2013/062947 A1 | 5/2013 |
| WO | 2013/070600 A1 | 5/2013 |

OTHER PUBLICATIONS

King, Med. Chem. Principle and Practice (1994) pp. 206-208.*
Ichii, O., et al., "Podocyte Injury Caused by Indoxyl Sulfate, a Uremic Toxin and Aryl-Hydrocarbon Receptor Ligand," PLOS One 9(9):e108448, Sep. 2014, 15 pages.
International Search Report dated Nov. 7, 2017, filed in corresponding International Application No. PCT/JP2017/036272, filed Oct. 5, 2017, 3 pages.
Schulman, G., et al., "A Multicenter, Randomized, Double-Blind, Placebo-Controlled, Dose-Ranging Study of AST-120 (Kremezin) in Patients With Moderate to Severe CKD," American Journal of Kidney Diseases 47(4):565-577, Apr. 2006.
Shimizu, H., et al., "Senescence and Dysfunction of Proximal Tubular Cells are Associated With Activated p53 Expression by Indoxyl Sulfate," American Journal of Physiology: Cell Physiology 299(5):C1110-C1117, Nov. 2010.
Yamada, K., et al., "Inhibitory Effect of β-PIPH on Some Enzymic Activities Related to Vitamin $B_6$," Folia Endocrinologica Japonica 37(10):1068-1072, 1962.
Livingston, R.J., et al., "*Homo sapiens* heat shock 70kDa protein 5 (glucose-regulated protein, 78kDa) (HSPA5) gene, complete cds," submitted Jan. 31, 2006 to GenBank: DQ385847.1, NIEHS-SNPs, Environmental Genome Project, NIEHS ES15478, Department of Genome Sciences, Seattle, Wash., 6 pages.
Chemical Abstract Registry No. 1505360-65-5, "Butanoic acid, 2-[[[(4-chlorophenyl)amino]carbonyl]amino]-2-ethyl," Supplier: Aurora Fine Chemicals, Dec. 27, 2013, EPO database, 1 page.

(Continued)

*Primary Examiner* — Taofiq A Solola
(74) *Attorney, Agent, or Firm* — Christensen O'Connor Johnson Kindness PLLC

(57) ABSTRACT

An object of the present invention is to find a novel pharmaceutical that has an excellent tryptophanase inhibitory effect, and suppresses worsening of renal function to preserve the kidney by reducing production of indoxyl sulfate in the blood. The present invention provides a pharmaceutical composition containing, as an active ingredient, a compound represented by the following formula, or a pharmacologically acceptable salt thereof:

[Formula 1]

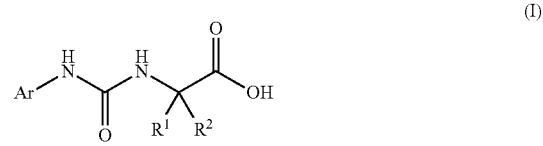

(I)

wherein $R^1$ and $R^2$ are the same or different, and represent a $C_1$-$C_6$ alkyl group or the like, and Ar represents an optionally substituted phenyl group or an optionally substituted thienyl group.

25 Claims, 3 Drawing Sheets

(56) References Cited

OTHER PUBLICATIONS

Chemical Abstract Registry No. 1512071-67-8, "Butanoic acid, 2-ethyl-2-[[[(4-fluorophenyl)amino]carbonyl]amino]," Supplier: Aurora Fine Chemicals, Jan. 6, 2014, EPO database, 1 page.
Chemical Abstract Registry No. 1516378-94-1, "Butanoic acid, 2-[[[(3-chlorophenyl)amino]carbonyl]amino]-2-ethyl," Supplier: Aurora Fine Chemicals, Jan. 10, 2014, EPO database, 1 page.
Chemical Abstract Registry No. 1516916-40-7, "Butanoic acid, 2-ethyl-2-[[(3-thienylamino)carbonyl]amino]," Supplier: Aurora Fine Chemicals, Jan. 10, 2014, EPO database, 1 page.
Chemical Abstract Registry No. 1521451-59-1, "Butanoic acid, 2-[[[(3-cyanophenyl)amino]carbonyl]amino]-2-ethyl," Supplier: Aurora Fine Chemicals, Jan. 16, 2014, EPO database, 1 page.
Chemical Abstract Registry No. 525686-58-1, "Butanoic acid, 2-ethyl-2-[[[(3-fluorophenyl)amino]carbonyl]amino]," Supplier: Aurora Fine Chemicals, Jan. 20, 2014, EPO database, 1 page.
European Extended Search Report dated May 6, 2020, issued in Application No. 17858482.7, filed May 10, 2017, 14 pages.
Wang, C., et al., "Revisiting the SAR of the Antischistosomal Aryl Hydantoin (Ro 13-3978)," Journal of Medicinal Chemistry 59(23):10705-10718, Nov. 2016.
Link, H., and H.R. Stohler, "3-Arylhydantoine, eine Substanzklasse mit schistosomizider Wirkung" [title translation: "3-Arylhydantoine, a Class of Schistosomicidal Compounds," European Journal of Medicinal Chemistry 19(3):261-265, Jan. 1984.
Canadian Office Action dated May 12, 2020, issued in corresponding Application No. CA 3,039,455, filed Apr. 4, 2019, 5 pages.
Chemical Abstract Registry No. 1525686-58-1, "Butanoic acid, 2-[[[(3-chlorophenyl)amino]carbonyllamino]-2-ethyl-," Chemical Catalog Supplier: Aurora Fine Chemicals, Jan. 20, 2014, STN Database, 1 page.
Chemical Abstract Registry No. 1516378-94-1, "Butanoic acid, 2-[[[(3-chlorophenyl)amino]carbonyllamino]-2-ethyl-," Chemical Catalog Supplier: Aurora Fine Chemicals, Jan. 10, 2014, Stn Database. 1 page.
Chemical Abstract Registry No. 1521451-59-1, "Butanoic acid, 2-[[[(3-cyanophenyl)amino]carbonyl]amino]-2-ethyl-," Chemical Catalog Supplier: Aurora Fine Chemicals, Jan. 16, 2014, Stn Database, 1 page.
Chemical Abstract Registry No. 1512071-67-8, "Butanoic acid, 2-ethyl-2-[[[(4-fluorophenyl)amino]carbonyllaminol-," Chemical Catalog Supplier: Aurora Fine Chemicals, STN Database, Jan. 6, 2014, 1 page.
Chemical Abstract Registry No. 1505360-65-5, "Butanoic acid, 2-[[[(4-chlorophenyl)amino]carbonyllamino]-2-ethyl-," Chemical Catalog Supplier: Aurora Fine Chemicals, STN Database, Dec. 27, 2013, 2 pages.
Chemical Abstract Registry No. 1516916-40-7, "Butanoic acid, 2-ethyl-2-[[(3-thienylamino)carbonyl]aminol-," Chemical catalog Supplier: Aurora Fine Chemicals, STN Database, Jan. 10, 2014, 1 page.
Chemical Abstract Registry No. 1978636-84-8, "Butanoic acid, 2-[[[(2,5-difluoro-4-methylphenyl)amino]carbonyl] amino]-2-ethyl-," Chemical Catalog Supplier: Aurora Fine Chemicals, STN Database, Aug. 24, 2016, 1 page.
Chemical Abstract Registry No. 1978134-76-7, "Butanoic acid, 2[[[2-bromo-3-chlorophenyl)aminolcarbonyliamino]-2- athyl-," Chemical Catalog Supplier Aurora Fine Chemicals, STN Database, Aug. 23, 2016, 1 page.
Chemical Abstract Registry No. 1962034-77-0, "Butanoic acid, 2-[[[(2-bromo-4-cyanophenyl)amino]carbonyllamino]-2- athyl-," Chemical Catalog Supplier Aurora Fine Chemicals, Stn Database, Jul. 28, 2016, 1 page.
Chemical Abstract Registry No. 1962026-77-2, "Butanoic acid, 2-[[[(4-bromo-3,5-dimethylphenyl)amino]carbonyl] amino]-2-ethyl-," Chemical Catalog Supplier: Aurora Fine Chemicals, STN Database, Jul. 28, 2016, 1 page.
Chemical Abstract Registry No. 1961514-93-1, "Butanoic acid, 2-ethyl-2-[[[(4-hydroxphenyOmethylamino]carbonyl] amino]-," Chemical Catalog Supplier: Aurora Fine Chemicals, STN Database, Jul. 28, 2016, 1 page.
Chinese Search Report dated Jan. 13, 2021, issued in corresponding Application No. 2017800619757, filed Oct. 5, 2017, 5 pages.
Chinese Office Action dated Jan. 20, 2021, issued in corresponding Application No. 2017800619757, filed Oct. 5, 2017, 14 pages.

* cited by examiner

UREA DERIVATIVE

TECHNICAL FIELD

The present invention relates to a urea derivative having an excellent tryptophanase inhibitory effect, or a pharmacologically acceptable salt thereof.

BACKGROUND ART

Chronic kidney disease is a significant problem in society. In current drug therapy for chronic kidney disease patients, a renin-angiotensin-based inhibitor such as an angiotensin II receptor antagonist (ARB) or an angiotensin converting enzyme (ACE) inhibitor is used as a first-line-drug, and a calcium antagonist and a diuretic are used as second- or third-line-drugs. Based on comorbid diseases and primary diseases, a large number of oral drugs are prescribed, such as therapeutic drugs for hyperuricemia, therapeutic drugs for hyperlipidemia, therapeutic drugs for diabetes, steroid/immunosuppressive agents, antiplatelet drugs/anticoagulation drugs, therapeutic drugs for hyperphosphatemia, erythropoiesis stimulating factor preparations, analgesics, antiarrhythmic drugs, antidepressants, therapeutic drugs for Alzheimer type dementia, Parkinson's disease drugs, proton pump inhibitors (PPI), antiallergic drugs and antimicrobials. There is, however, a demand for development of better therapeutic drugs for these diseases.

Indole, which is produced by tryptophanase-expressing intestinal bacteria with tryptophan as a substrate, is a precursor of indoxyl sulfate (IS), a uremic toxin which accelerates the progression of pathological conditions of chronic kidney disease. Indoxyl sulfate, which is produced from indole through hydroxylation/sulfation, is a uremic toxin that not only deteriorates kidney function and thus accelerates transition to end-stage kidney failure (transition to renal replacement therapy or kidney transplant) but also causes deterioration and dysfunction of blood vessels to cause cardiovascular disease and a further increase in morbidity. Uremic toxins are also deeply involved in disorders of various organs such as nerves, bones, blood cells and skeletal muscles, and uremic symptoms. Spherical adsorptive carbon is commercially available as a pharmaceutical capable of reducing indoxyl sulfate in the blood, and adsorbs indole produced by tryptophanase in the lumen of the digestive tract to evacuate it with excrement. The indoxyl sulfate-reducing function of spherical adsorptive carbon in blood is, however, weak, particularly in humans, and is insufficient because it is unable to reduce blood indoxyl sulfate concentration down to a concentration level of a healthy person (Non Patent Literature 1).

Transition to kidney transplant or dialysis based on kidney dysfunction is increasing worldwide. For example, the number of dialysis patients in Japan exceeds 310,000 at present and is still increasing. A patient needs to go to hospital three times a week for dialysis, and the dialysis itself takes time. Besides, dialysis is a heavy burden also from the point of view of medical economics. Kidney transplant is also considered as an alternative to dialysis, but the number of donors is limited, and there is therefore a significant problem to be solved preserving renal function as long as possible to support the life of patients. In other words, it has become very important to delay transition to renal replacement therapy in patients undergoing conservative treatment of chronic kidney failure to gain time until appearance of a donor for kidney transplantation. Besides, after transition to renal replacement therapy, it is important, also in the sense of water regulation and the like, to suppress worsening of remaining renal function and obtain a sufficient urine volume. Indoxyl sulfate accelerates production of ROS (reactive oxygen species) in renal tubular epithelial cells and accelerates cell senescence (Non Patent Literature 2). It is also known to cause failure in renal glomerular epithelial cells via an AhR (aryl hydrocarbon receptor) (Non Patent Literature 3) Therefore, reducing the production of indoxyl sulfate is expected to greatly reduce such influences on renal cells and to suppress worsening of renal function and preserve the kidney.

Patent Literature 1 and 2 describe an aryl urea derivative having a N-formylpeptide receptor modulatory function, but neither disclose or suggest a compound of formula (I) of the present invention described below, or a specific salt of the compound.

[Formula 1]

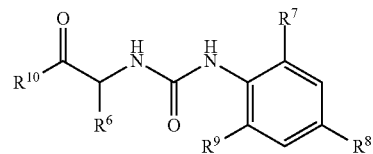

Besides, Patent Literature 3 describes a urea derivative that inhibits fatty acid binding protein (FABP) 4 and/or 5, but neither discloses nor suggests the compound of formula (I) of the present invention described below, or a specific salt of the compound.

[Formula 2]

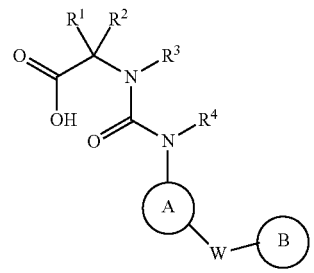

In this formula, $R^1$ and $R^2$ form a cycloalkyl group together with the carbon atom to which they are bound. In addition, a variety of reagents are commercially available from AKos Consulting and Solutions Deutschland GmbH, Aldlab Chemicals, LLC, Aurora Fine Chemicals LLC, Shanghai Chemhere Co., Ltd. and the like, but medical uses such as the tryptophanase inhibitory effect of the present invention are not known.

CITATION LIST

Patent Literature

Patent Literature 1: WO2014/138037
Patent Literature 2: WO2013/070600
Patent Literature 3: WO2014/146995

Non Patent Literature

Non Patent Literature 1: Schulman-G AJKD, Vol. 47, NO 4, 2006

Non Patent Literature 2: Shimizu-H, Am J Physiol Cell Physiol 299: C1110-C1117, 2010

Non Patent Literature 3: Ichii-O, PLOS ONE 9(9), e108448, 2014

SUMMARY OF INVENTION

Technical Problem

Currently known compounds having a tryptophanase inhibitory function are not satisfactory in terms of efficacy, and a tryptophanase inhibitor having excellent efficacy has been desired.

Solution to Problem

The present inventors carried out various synthetic studies aiming to provide a novel pharmaceutical that has excellent tryptophanase inhibitory function and suppresses worsening of renal function to preserve a kidney by greatly reducing the indoxyl sulfate concentration in the blood and kidney by inhibiting the production of indole, i.e., a precursor of indoxyl sulfate. As a result, it was found that a urea derivative having a specific structure or a pharmacologically acceptable salt thereof has excellent tryptophanase inhibitory function, and the present invention was thus accomplished.

The present invention provides a urea derivative having excellent tryptophanase inhibitory function or a pharmacologically acceptable salt thereof, and a pharmaceutical composition containing these.

Specifically, the present invention provides the following:

(1) a pharmaceutical composition comprising, as an active ingredient, a compound represented by the following general formula (I) or a pharmacologically acceptable salt thereof:

[Formula 3]

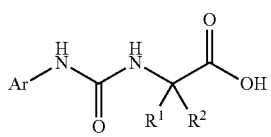

(I)

wherein $R^1$ and $R^2$ are the same or different, and represent a $C_1$-$C_6$ alkyl group, a halogeno $C_1$-$C_6$ alkyl group or a $C_3$-$C_6$ cycloalkyl group; and Ar represents an optionally substituted phenyl group, the substituent being the same or different one to two substituents selected from a halogen atom, a cyano group, a $C_1$-$C_6$ alkyl group, a halogeno $C_1$-$C_6$ alkyl group, a cyano $C_1$-$C_6$ alkyl group, a $C_3$-$C_6$ cycloalkyl group, a cyano $C_3$-$C_6$ cycloalkyl group, a $C_1$-$C_6$ alkoxy group, a halogeno $C_1$-$C_6$ alkoxy group, a $C_1$-$C_6$ alkylthio group, a halogeno $C_1$-$C_6$ alkylthio group, a di($C_1$-$C_3$ alkyl) amino group, a saturated cyclic amino group, a halogeno saturated cyclic amino group, a phenyl group and a halogeno phenyl group; or Ar represents an optionally substituted thienyl group, the substituent being a halogen atom, a cyano group or a $C_1$-$C_6$ alkyl group;

(2) the pharmaceutical composition according to (1), comprising, as an active ingredient, a compound represented by the following general formula (I) or a pharmacologically acceptable salt thereof:

[Formula 4]

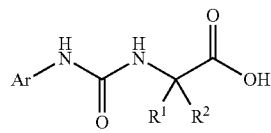

(I)

wherein $R^1$ and $R^2$ are the same or different, and represent a $C_1$-$C_6$ alkyl group or a $C_3$-$C_6$ cycloalkyl group; and Ar represents an optionally substituted phenyl group, the substituent being the same or different one to two substituents selected from a halogen atom, a cyano group, a halogeno $C_1$-$C_6$ alkyl group, a cyano $C_1$-$C_6$ alkyl group, a cyano $C_3$-$C_6$ cycloalkyl group, a halogeno $C_1$-$C_6$ alkoxy group, a halogeno $C_1$-$C_6$ alkylthio group, a saturated cyclic amino group, a halogeno saturated cyclic amino group, a phenyl group and a halogeno phenyl group; or Ar represents a 2- or 3-thienyl group substituted in position 5 with a halogen atom;

(3) a compound represented by the following general formula (I) or a pharmacologically acceptable salt thereof:

[Formula 5]

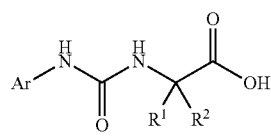

(I)

wherein (A) Ar represents a group represented by the following formula:

[Formula 6]

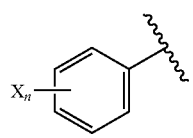

wherein $R^1$ represents a methyl group, $R^2$ represents an ethyl group or a $C_4$-$C_6$ alkyl group, n represents 1 or 2, each X independently represents a halogen atom, a cyano group, a halogeno $C_1$-$C_6$ alkyl group, a cyano $C_1$-$C_6$ alkyl group, a cyano $C_3$-$C_6$ cycloalkyl group, a halogeno $C_1$-$C_6$ alkoxy group, a halogeno $C_1$-$C_6$ alkylthio group, a saturated cyclic amino group, a halogeno saturated cyclic amino group, a phenyl group or a halogeno phenyl group;

(B) Ar represents a group represented by the following formula:

[Formula 7]

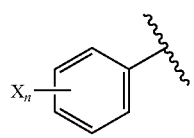

wherein $R^1$ represents a $C_3$-$C_6$ cycloalkyl group, $R^2$ represents a $C_2$-$C_6$ alkyl group or a $C_3$-$C_6$ cycloalkyl group, n represents 0, 1 or 2, and each X independently represents a halogen atom, a cyano group, a halogeno $C_1$-$C_6$ alkyl group, a cyano $C_1$-$C_6$ alkyl group, a cyano $C_3$-$C_6$ cycloalkyl group, a halogeno $C_1$-$C_6$ alkoxy group, a halogeno $C_1$-$C_6$ alkylthio group, a saturated cyclic amino group, a halogeno saturated cyclic amino group, a phenyl group or a halogeno phenyl group;

(C) Ar represents a group represented by the following formula:

[Formula 8]

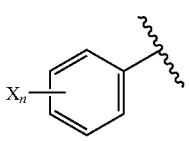

wherein $R^1$ and $R^2$ are the same or different and represent a $C_2$-$C_6$ alkyl group, n represents 1 or 2, and each X independently represents a halogen atom, a cyano group, a halogeno $C_1$-$C_6$ alkyl group, a cyano $C_2$-$C_6$ alkyl group, a cyano $C_3$-$C_6$ cycloalkyl group, a halogeno $C_1$-$C_6$ alkoxy group, a halogeno $C_1$-$C_6$ alkylthio group, a saturated cyclic amino group, a halogeno saturated cyclic amino group, a phenyl group or a halogeno phenyl group, provided that X does not represent a halogen atom or a cyano group when n represents 1; or (D) Ar represents a group represented by the following formula:

[Formula 9]

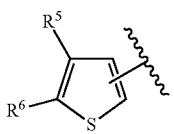

wherein $R^1$ and $R^2$ are the same or different and represent a $C_1$-$C_6$ alkyl group or a $C_3$-$C_6$ cycloalkyl group, $R^5$ represents a hydrogen atom, and $R^6$ represents a halogen atom;

(4) the compound according to (3) represented by the following general formula (I-1) or a pharmacologically acceptable salt thereof:

[Formula 10]

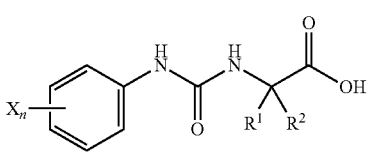

(I-1)

wherein $R^1$ represents a methyl group, $R^2$ represents an ethyl group or a $C_4$-$C_6$ alkyl group, n represents 1 or 2, and each X independently represents a halogen atom, a cyano group, a halogeno $C_1$-$C_6$ alkyl group, a cyano $C_1$-$C_6$ alkyl group, a cyano $C_3$-$C_6$ cycloalkyl group, a halogeno $C_1$-$C_6$ alkoxy group, a halogeno $C_1$-$C_6$ alkylthio group, a saturated cyclic amino group, a halogeno saturated cyclic amino group, a phenyl group or a halogeno phenyl group;

(5) the compound according to (4) represented by the following general formula (I-2) or a pharmacologically acceptable salt thereof:

[Formula 11]

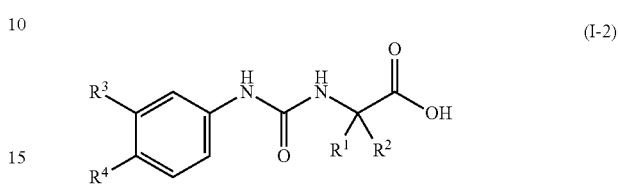

(I-2)

wherein $R^1$ represents a methyl group, $R^2$ represents an ethyl group or a $C_4$-$C_6$ alkyl group, $R^3$ represents a hydrogen atom, a halogen atom or a cyano group, and $R^4$ represents a halogen atom, a cyano group, a halogeno $C_1$-$C_6$ alkyl group, a cyano $C_1$-$C_6$ alkyl group, a cyano $C_3$-$C_6$ cycloalkyl group, a halogeno $C_1$-$C_6$ alkoxy group, a halogeno $C_1$-$C_6$ alkylthio group, a saturated cyclic amino group, a halogeno saturated cyclic amino group, a phenyl group or a halogeno phenyl group;

(6) the compound according to (4) or (5), or a pharmacologically acceptable salt thereof, wherein $R^2$ represents an ethyl group;

(7) the compound according to (5) or (6), or a pharmacologically acceptable salt thereof, wherein $R^3$ represents a hydrogen atom, a fluorine atom or a cyano group;

(8) the compound according to any one of (5) to (7), or a pharmacologically acceptable salt thereof, wherein $R^4$ represents a fluorine atom, a chlorine atom, a bromine atom, an iodine atom, a 2,2,2-trifluoroethyl group, a difluoromethoxy group or a trifluoromethoxy group;

(9) the compound according to (3) represented by the following general formula (I-3), or a pharmacologically acceptable salt thereof:

[Formula 12]

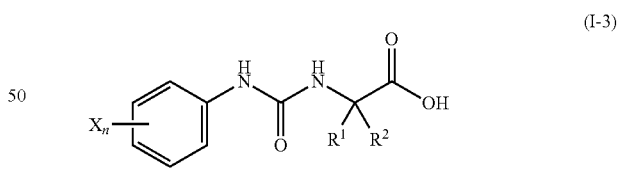

(I-3)

wherein $R^1$ represents a $C_3$-$C_6$ cycloalkyl group, $R^2$ represents a $C_2$-$C_6$ alkyl group or a $C_3$-$C_6$ cycloalkyl group, n represents 0, 1 or 2, and each X independently represents a halogen atom, a cyano group, a halogeno $C_1$-$C_6$ alkyl group, a cyano $C_1$-$C_6$ alkyl group, a cyano $C_3$-$C_6$ cycloalkyl group, a halogeno $C_1$-$C_6$ alkoxy group, a halogeno $C_1$-$C_6$ alkylthio group, a saturated cyclic amino group, a halogeno saturated cyclic amino group, a phenyl group or a halogeno phenyl group;

(10) the compound according to (9) represented by the following general formula (I-4), or a pharmacologically acceptable salt thereof:

[Formula 13]

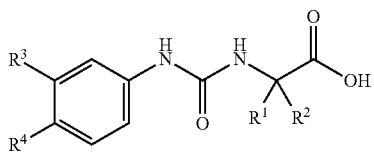

(I-4)

wherein $R^1$ represents a $C_3$-$C_6$ cycloalkyl group, $R^2$ represents a $C_2$-$C_6$ alkyl group or a $C_3$-$C_6$ cycloalkyl group, $R^3$ represents a hydrogen atom, a halogen atom or a cyano group, and $R^4$ represents a halogen atom, a cyano group, a halogeno $C_1$-$C_6$ alkyl group, a cyano $C_1$-$C_6$ alkyl group, a cyano $C_3$-$C_6$ cycloalkyl group, a halogeno $C_1$-$C_6$ alkoxy group, a halogeno $C_1$-$C_6$ alkylthio group, a saturated cyclic amino group, a halogeno saturated cyclic amino group, a phenyl group or a halogeno phenyl group;

(11) the compound according to (9) or (10), or a pharmacologically acceptable salt thereof, wherein $R^1$ represents a cyclopropyl group;

(12) the compound according to any one of (9) to (11), or a pharmacologically acceptable salt thereof, wherein $R^2$ represents an ethyl group or a cyclopropyl group;

(13) the compound according to any one of (10) to (12), or a pharmacologically acceptable salt thereof, wherein $R^3$ represents a hydrogen atom, and $R^4$ represents a fluorine atom, a cyano group, a cyanomethyl group, a 2,2,2-trifluoroethyl group, a difluoromethoxy group or a trifluoromethoxy group;

(14) the compound according to any one of (10) to (12), or a pharmacologically acceptable salt thereof, wherein $R^3$ represents a cyano group, and $R^4$ represents a hydrogen atom;

(15) the compound according to (3) represented by the following general formula (I-5), or a pharmacologically acceptable salt thereof:

[Formula 14]

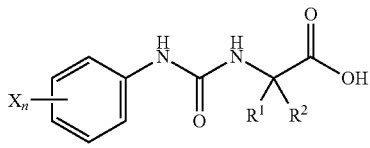

(I-5)

wherein $R^1$ and $R^2$ are the same or different and represent a $C_2$-$C_6$ alkyl group, n represents 1 or 2, and each X independently represents a halogen atom, a cyano group, a halogeno $C_1$-$C_6$ alkyl group, a cyano $C_2$-$C_6$ alkyl group, a cyano $C_3$-$C_6$ cycloalkyl group, a halogeno $C_1$-$C_6$ alkoxy group, a halogeno $C_1$-$C_6$ alkylthio group, a saturated cyclic amino group, a halogeno saturated cyclic amino group, a phenyl group or a halogeno phenyl group, provided that X does not represent a halogen atom or a cyano group when n represents 1;

(16) the compound according to (15) represented by the following general formula (I-6), or a pharmacologically acceptable salt thereof:

[Formula 15]

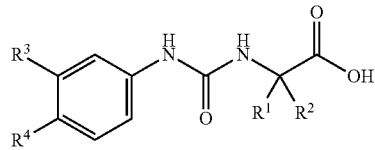

(I-6)

wherein $R^1$ and $R^2$ are the same or different and represent a $C_2$-$C_6$ alkyl group, $R^3$ represents a hydrogen atom, a halogen atom or a cyano group, and $R^4$ represents a halogen atom, a cyano group, a halogeno $C_1$-$C_6$ alkyl group, a cyano $C_2$-$C_6$ alkyl group, a cyano $C_3$-$C_6$ cycloalkyl group, a halogeno $C_1$-$C_6$ alkoxy group, a halogeno $C_1$-$C_6$ alkylthio group, a saturated cyclic amino group, a halogeno saturated cyclic amino group, a phenyl group or a halogeno phenyl group, provided that $R^4$ does not represent a halogen atom or a cyano group when $R^3$ represents a hydrogen atom;

(17) the compound according to (15) or (16), or a pharmacologically acceptable salt thereof, wherein $R^1$ and $R^2$ are the same or different and represent an ethyl group, a propyl group or an isopropyl group;

(18) the compound according to (15) or (16), or a pharmacologically acceptable salt thereof, wherein $R^1$ and $R^2$ represent a combination of an ethyl group and an ethyl group, or an ethyl group and a propyl group;

(19) the compound according to (15) or (16), or a pharmacologically acceptable salt thereof, wherein $R^1$ and $R^2$ both represent an ethyl group;

(20) the compound according to any one of (16) to (19), or a pharmacologically acceptable salt thereof, wherein $R^3$ represents a hydrogen atom;

(21) the compound according to any one of (16) to (19), or a pharmacologically acceptable salt thereof, wherein $R^4$ represents a trifluoromethyl group, a monofluoromethoxy group, a difluoromethoxy group, a trifluoromethoxy group, a trifluoromethylthio group, a phenyl group or a 2-fluorophenyl group;

(22) the compound according to (3) represented by the following general formula (I-7), or a pharmacologically acceptable salt thereof:

[Formula 16]

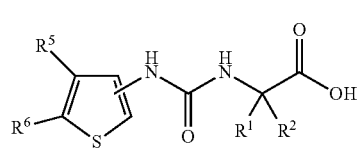

(I-7)

wherein $R^1$ and $R^2$ are the same or different and represent a $C_1$-$C_6$ alkyl group or a $C_3$-$C_6$ cycloalkyl group, $R^5$ represents a hydrogen atom, and $R^6$ represents a halogen atom;

(23) the compound according to (22), or a pharmacologically acceptable salt thereof, wherein $R^1$ and $R^2$ both represent an ethyl group;

(24) the compound according to (22) or (23), or a pharmacologically acceptable salt thereof, wherein $R^6$ represents a chlorine atom;

(25) the compound according to (3), selected from the group consisting of dicyclopropyl({[4-(trifluoromethoxy)phenyl]carbamoyl}amino)acetic acid, 2-cyclopropyl-2-({[4-(trifluoromethoxy)phenyl]carbamoyl}amino)butanoic acid, N-{[4-(difluoromethoxy)phenyl]carbamoyl}-D-isovaline, 2-cyclopropyl-2-({[4-(difluoromethoxy)phenyl]carbamoyl}amino)butanoic acid, N-{[4-(2,2,2-trifluoroethyl)phenyl]carbamoyl}-D-isovaline, N-{[4-(difluoromethoxy)-3-fluorophenyl]carbamoyl}-D-isovaline, 2-cyclopropyl-2-[(phenylcarbamoyl)amino]butanoic acid, 2-cyclopropyl-2-{[(4-fluorophenyl)carbamoyl]amino}butanoic acid, N-[(4-chlorophenyl)carbamoyl]-D-isovaline, 2-{[(5-chlorothiophen-3-yl)carbamoyl]amino}-2-ethylbutanoic acid, N-[(4-bromophenyl)carbamoyl]-D-isovaline, N-[(4-iodophenyl)carbamoyl]-D-isovaline and 2-{[(3-cyanophenyl)carbamoyl]amino}-2-cyclopropylbutanoic acid; or a pharmacologically acceptable salt thereof;

(26) the compound according to (3), selected from the group consisting of: N-{[4-(difluoromethoxy)phenyl]carbamoyl}-D-isovaline, N-{[4-(difluoromethoxy)-3-fluorophenyl]carbamoyl}-D-isovaline, N-[(4-chlorophenyl)carbamoyl]-D-isovaline, N-[(4-bromophenyl)carbamoyl]-D-isovaline, N-[(4-iodophenyl)carbamoyl]-D-isovaline, (2R)-2-{[(3-cyanophenyl)carbamoyl]amino}-2-cyclopropylbutanoic acid, (2S)-2-{[(3-cyanophenyl)carbamoyl]amino}-2-cyclopropylbutanoic acid and 2-{[(5-chlorothiophen-3-yl)carbamoyl]amino}-2-ethylbutanoic acid; or a pharmacologically acceptable salt thereof;

(27) a pharmaceutical composition comprising, as an active ingredient, the compound according to any one of (3) to (26), or a pharmacologically acceptable salt thereof;

(28) a crystalline form of the compound according to (3), selected from the group consisting of:
crystalline N-{[4-(difluoromethoxy)phenyl]carbamoyl}-D-isovaline having characteristic peaks at interplanar spacings d of 7.51, 7.33, 6.67, 6.15, 5.32, 5.24, 4.98, 4.79, 3.96 and 3.59 angstroms;
crystalline N-{[4-(difluoromethoxy)-3-fluorophenyl]carbamoyl}-D-isovaline having characteristic peaks at interplanar spacings of 9.52, 6.10, 5.45, 5.29, 4.94, 4.89, 4.75, 3.80, 3.48 and 3.44 angstroms;
crystalline N-[(4-chlorophenyl)carbamoyl]-D-isovaline having characteristic peaks at interplanar spacings of 15.60, 6.23, 5.68, 5.34, 5.20, 4.59, 4.53, 3.83, 3.37 and 3.15 angstroms;
crystalline N-[(4-bromophenyl)carbamoyl]-D-isovaline having characteristic peaks at interplanar spacings of 15.82, 6.50, 6.25, 5.39, 4.67, 3.92, 3.86, 3.59, 3.39 and 3.16 angstroms;
crystalline N-[(4-iodophenyl)carbamoyl]-D-isovaline having characteristic peaks at interplanar spacings of 16.92, 6.62, 4.99, 4.44, 4.30, 4.18, 3.30, 3.21, 3.07 and 3.02 angstroms;
crystalline (+)-2-{[(3-cyanophenyl)carbamoyl]amino}-2-cyclopropylbutanoic acid having characteristic main peaks at interplanar spacings of 11.30, 8.35, 7.66, 5.64, 5.46, 5.22, 4.73, 4.50, 4.35 and 4.02 angstroms;
crystalline (−)-2-{[(3-cyanophenyl)carbamoyl]amino}-2-cyclopropylbutanoic acid having characteristic peaks at interplanar spacings of 15.66. 11.62, 11.30, 8.35, 7.80, 6.84, 5.45, 5.22, 4.5 and 4.02 angstroms; and
crystalline 2-{[(5-chlorothiophen-3-yl)carbamoyl]amino}-2-ethylbutanoic acid having characteristic peaks at interplanar spacings of 15.82, 9.42, 6.53, 5.85, 5.48, 5.24, 4.69, 4.46, 3.58 and 3.12 angstroms,
all in powder X-ray diffraction obtained through irradiation with copper Kα radiation (wavelength λ=1.54 angstroms);

(29) a pharmaceutical composition comprising, as an active ingredient, any one of the crystalline forms of the compound according to (28);

(30) the pharmaceutical composition according to (1) or (2), comprising, as an active ingredient, a compound selected from the group consisting of:
2-ethyl-2-[(phenylcarbamoyl)amino]butanoic acid,
2-{[3-(chlorophenyl)carbamoyl]amino}-2-ethylbutanoic acid,
2-{[4-(chlorophenyl)carbamoyl]amino}-2-ethylbutanoic acid,
2-ethyl-2-{[4-(fluorophenyl)carbamoyl]amino}butanoic acid,
2-ethyl-2-{[3-(fluorophenyl)carbamoyl]amino}butanoic acid,
2-{[3-(cyanophenyl)carbamoyl]amino}-2-ethylbutanoic acid,
2-({[4-(cyanomethyl)phenyl]carbamoyl}amino)-2-ethylbutanoic acid, and
2-ethyl-2-[(thiophen-3-ylcarbamoyl)amino]butanoic acid,
or a pharmacologically acceptable salt thereof;

(31) the pharmaceutical composition according to (1), (2), (27), (29) or (30), wherein the pharmaceutical composition is a tryptophanase inhibitor;

(32) the pharmaceutical composition according to (1), (2), (27), (29) or (30), wherein the pharmaceutical composition is a pharmaceutical composition for reducing indoxyl sulfate in the blood;

(33) the pharmaceutical composition according to (1), (2), (27), (29) or (30), wherein the pharmaceutical composition is a pharmaceutical composition for suppressing worsening of renal function;

(34) the pharmaceutical composition according to (1), (2), (27), (29) or (30), for preventing or treating a disease caused by an increase in indoxyl sulfate in the blood;

(35) the pharmaceutical composition according to (1), (2), (27), (29) or (30), wherein the pharmaceutical composition is a pharmaceutical composition for delaying transition to renal replacement therapy in a patient in a period of conservative treatment of chronic kidney disease;

(36) the pharmaceutical composition according to (1), (2), (27), (29) or (30), wherein the pharmaceutical composition is a pharmaceutical composition for suppressing worsening of remaining renal function in a patient after transition to renal replacement therapy;

(37) an agent for reducing indoxyl sulfate in the blood, comprising, as an active ingredient, the compound according to any one of (3) to (26) or a pharmacologically acceptable salt thereof, or a crystalline form of the compound according to 28;

(38) an agent for preventing or treating a disease caused by an increase in indoxyl sulfate in the blood, comprising, as an active ingredient, the compound according to any one of (3) to (26) or a pharmacologically acceptable salt thereof, or a crystalline form of the compound according to 28;

(39) an agent for delaying transition to renal replacement therapy in a patient in a period of conservative treatment of chronic kidney disease, comprising, as an active ingredient, the compound according to any one of (3) to (26) or a pharmacologically acceptable salt thereof, or a crystalline form of the compound according to 28;

(40) an agent for suppressing worsening of remaining renal function in a patient after transition to renal replacement therapy, comprising, as an active ingredient, the compound according to any one of (3) to (26) or a pharmacologically acceptable salt thereof, or a crystalline form of the compound according to 28;

(41) use of the compound according to any one of (3) to (26) or a pharmacologically acceptable salt thereof, or a crystalline form of the compound according to 28, for producing a pharmaceutical composition;

(42) the use according to (41), for producing a pharmaceutical composition for preventing or treating a disease caused by an increase in indoxyl sulfate in the blood;

(43) the use according to (41), for producing a pharmaceutical composition for delaying transition to renal replacement therapy in a patient in a period of conservative treatment of chronic kidney disease;

(44) the use according to (41), for producing a pharmaceutical composition for suppressing worsening of remaining renal function in a patient after transition to renal replacement therapy;

(45) a method for reducing indoxyl sulfate in the blood, comprising administering, to a mammal, an effective dose of the compound according to any one of (3) to (26) or a pharmacologically acceptable salt thereof, or a crystalline form of the compound according to 28;

(46) the method according to (45), wherein the mammal is a human;

(47) a method for preventing or treating a disease, comprising administering, to a mammal, an effective dose of the compound according to any one of (3) to (26) or a pharmacologically acceptable salt thereof, or a crystalline form of the compound according to 28;

(48) the method according to (47), wherein the mammal is a human;

(49) the method according to (47) or (48), wherein the disease is a disease caused by an increase in indoxyl sulfate in the blood;

(50) the compound according to any one of (3) to (26) or a pharmacologically acceptable salt thereof, or a crystalline form of the compound according to 28, for use in a method for preventing or treating a disease; and

(51) the compound according to (50) or a pharmacologically acceptable salt thereof, wherein the disease is a disease caused by an increase in indoxyl sulfate in the blood.

Now, definitions of the substituents used in the inventive compound (I) will be described.

In the compound (I) of the present invention, a "$C_1$-$C_6$ alkyl group" is a straight or branched saturated hydrocarbon group having 1 to 6 carbon atoms, and is, for example, a methyl group, an ethyl group, a propyl group, an isopropyl group, a butyl group, a sec-butyl group, a tert-butyl group, an isobutyl group, a pentyl group or a hexyl group, is preferably a straight or branched saturated hydrocarbon group having 1 to 3 carbon atoms ($C_1$-$C_3$ alkyl group), and is more preferably a methyl group or an ethyl group.

In the compound (I) of the present invention, a "halogen atom" is a fluorine atom, a chlorine atom, bromine atom or an iodine atom, and is preferably a fluorine atom or a chlorine atom.

In the compound (I) of the present invention, a "halogeno $C_1$-$C_6$ alkyl group" is the "$C_1$-$C_6$ alkyl group" substituted with the same or different one to three "halogen atoms" described above, and is, for example, a monofluoromethyl group, a monochloromethyl group, a difluoromethyl group, a dichloromethyl group, a chlorofluoromethyl group, a trifluoromethyl group or a 2,2,2-trifluoroethyl group, is preferably a methyl group or an ethyl group substituted with one to three fluorine atoms, is more preferably a monofluoromethyl group, a difluoromethyl group, a trifluoromethyl group or a 2,2,2-trifluoroethyl group, and is particularly preferably a trifluoromethyl group or a 2,2,2-trifluoroethyl group.

In the compound (I) of the present invention, a "$C_3$-$C_6$ cycloalkyl group" is a cyclic saturated hydrocarbon group having 3 to 6 carbon atoms, such as a cyclopropyl group, a cyclobutyl group, a cyclopentyl group or a cyclohexyl group, and is preferably a cyclopropyl group.

In the compound (I) of the present invention, a "cyano $C_1$-$C_6$ alkyl group" is a methyl group substituted with a cyano group and optionally substituted with a $C_1$-$C_5$ alkyl group, and is, for example, a cyanomethyl group, a 1-cyanoethyl group, a 1-cyanopropyl group, a 1-cyanoisopropyl group or a 1-cyanobutyl group, and is preferably a cyanomethyl group or a 1-cyanoethyl group.

In the compound (I) of the present invention, a "cyano $C_3$-$C_6$ cycloalkyl group" is the "$C_3$-$C_6$ cycloalkyl group" substituted with a cyano group, is preferably a cyclopropyl group substituted with a cyano group, and is more preferably a 1-cyanocyclopropyl group.

In the compound (I) of the present invention, a "$C_1$-$C_6$ alkoxy group" is an oxygen atom to which the "$C_1$-$C_6$ alkyl group" is bonded, and is, for example, a methoxy group, an ethoxy group, a propoxy group, an isopropoxy group or a butoxy group, is suitably an oxygen atom to which the "$C_1$-$C_3$ alkyl group" is bonded ($C_1$-$C_3$ alkoxy group), and is more preferably a methoxy group or an ethoxy group.

In the compound (I) of the present invention, a "halogeno $C_1$-$C_6$ alkoxy group" is an oxygen atom substituted by the "halogeno $C_1$-$C_6$ alkyl group", and is, for example, a monofluoromethoxy group, a difluoromethoxy group or a trifluoromethoxy group, and is preferably a difluoromethoxy group or a trifluoromethoxy group.

In the compound (I) of the present invention, a "$C_1$-$C_6$ alkylthio group" is a sulfur atom to which the "$C_1$-$C_6$ alkyl group" is bonded, and is, for example, a methylthio group, an ethylthio group, a propylthio group, an isopropylthio group or a butylthio group, is preferably a sulfur atom to which the "$C_1$-$C_3$ alkyl group" is bonded ($C_1$-$C_3$ alkylthio group), and is more preferably a methylthio group or an ethylthio group.

In the compound (I) of the present invention, a "halogeno $C_1$-$C_6$ alkylthio group" is a sulfur atom substituted by the "halogeno $C_1$-$C_6$ alkyl group", and is, for example, a monofluoromethylthio group, a difluoromethylthio group or a trifluoromethylthio group, and is preferably a difluoromethylthio group or a trifluoromethylthio group.

In the compound (I) of the present invention, a "di($C_1$-$C_3$ alkyl)amino group" is a nitrogen atom to which the "$C_1$-$C_3$ alkyl group" is bonded, and is, for example, a dimethylamino group or a diethylamino group.

In the compound (I) of the present invention, a "saturated cyclic amino group" is a 5- or 6-membered saturated cyclic amino group, and is preferably a 1-pyrrolidinyl group or a 1-piperidinyl group.

In the compound (I) of the present invention, a "halogeno saturated cyclic amino group" is the "saturated cyclic amino group" in which the same or different one to four "halogen atoms" described above are substituted, and is preferably a 3,3-difluoro-1-pyrrolidinyl group.

In the compound (I) of the present invention, a "halogeno phenyl group" is a phenyl group substituted with the same or different one to five "halogen atoms" described above, is preferably a phenyl group substituted with the same or different one to two "halogen atoms" described above, and is more preferably a 2-fluorophenyl group.

In Ar of the compound (I) of the present invention, a substituent of the "substituted phenyl group" is preferably the same or different one to two substituents selected from a halogen atom, a cyano group, a halogeno $C_1$-$C_6$ alkyl group, a cyano $C_1$-$C_6$ alkyl group, a cyano $C_3$-$C_6$ cycloalkyl group, a halogeno $C_1$-$C_6$ alkoxy group, a halogeno $C_1$-$C_6$ alkylthio group, a saturated cyclic amino group, a halogeno saturated cyclic amino group, a phenyl group or a halogeno phenyl group, is more preferably a fluorine atom, a chlorine atom, a bromine atom, an iodine atom, a 2,2,2-trifluoroethyl group, a difluoromethoxy group, a trifluoromethoxy group, a cyano group, a trifluoromethyl group, a trifluoromethylthio group, a phenyl group or a 2-fluorophenyl group, and is further preferably a fluorine atom, a chlorine atom, a bromine atom, an iodine atom, a difluoromethoxy group, a trifluoromethoxy group or a cyano group.

In the compound (I) of the present invention, a "thienyl group" is a 2-thienyl group or a 3-thienyl group.

In Ar of the compound (I) of the present invention, the "substituent of a substituted thienyl group" is preferably a "halogen atom", and is more preferably a chlorine atom.

Specific examples of preferable compounds of the compound (I) of the present invention include: dicyclopropyl({[4-(trifluoromethoxy)phenyl]carbamoyl}amino)acetic acid, 2-cyclopropyl-2-({[4-(trifluoromethoxy)phenyl] carbamoyl}amino)butanoic acid, N-{[4-(difluoromethoxy) phenyl]carbamoyl}-D-isovaline, 2-cyclopropyl-2-({[4-(difluoromethoxy)phenyl]carbamoyl}amino)butanoic acid, N-{ [4-(2,2,2-trifluoroethyl)phenyl]carbamoyl}-D-isovaline, N-{[4-(difluoromethoxy)-3-fluorophenyl]carbamoyl}-D-isovaline, 2-cyclopropyl-2-[(phenylcarbamoyl)amino]butanoic acid, 2-cyclopropyl-2-{[(4-fluorophenyl)carbamoyl] amino}butanoic acid, N-[(4-chlorophenyl)carbamoyl]-D-isovaline, 2-{[(5-chlorothiophen-3-yl)carbamoyl]amino}-2-ethylbutanoic acid, N-[(4-bromophenyl)carbamoyl]-D-isovaline, N-[(4-iodophenyl)carbamoyl]-D-isovaline and 2-{[(3-cyanophenyl)carbamoyl]amino}-2-cyclopropylbutanoic acid. Specific examples of a more preferable compound include: N-{[4-(difluoromethoxy)phenyl]carbamoyl}-D-isovaline, N-{[4-(difluoromethoxy)-3-fluorophenyl] carbamoyl}-D-isovaline, N-[(4-chlorophenyl)carbamoyl]-D-isovaline, N-[(4-bromophenyl)carbamoyl]-D-isovaline, N-[(4-iodophenyl)carbamoyl]-D-isovaline, (2R)-2-{[(3-cyanophenyl)carbamoyl]amino}-2-cyclopropylbutanoic acid, (2S)-2-{[(3-cyanophenyl)carbamoyl]amino}-2-cyclopropylbutanoic acid and 2-{[(5-chlorothiophen-3-yl)carbamoyl]amino}-2-ethylbutanoic acid.

In the compound (I) of the present invention, the term "a pharmacologically acceptable salt thereof" refers to a salt usable as a pharmaceutical. When a compound has an acidic group or a basic group, the compound can be changed into a "salt with a base" or an "acid addition salt" through reaction with a base or an acid, and the term refers to such a salt.

Preferable examples of the pharmacologically acceptable "salt with a base" of the compound include alkali metal salts such as sodium salts, potassium salts and lithium salts; alkaline earth metal salts such as magnesium salts and calcium salts; organic basic salts such as N-methylmorpholine salts, triethylamine salts, tributylamine salts, diisopropylethylamine salts, dicyclohexylamine salts, N-methylpiperidine salts, pyridine salts, 4-pyrrolidinopyridine salt and picoline salts, or amino acid salts such as glycine salts, lysine salts, arginine salts, ornithine salts, glutamic acid salts and aspartic acid salts, and alkali metal salts or alkaline earth metal salts are more preferable.

Preferable examples of the pharmacologically acceptable "acid addition salt" of the compound include inorganic acid salts such as hydrohalogenic acid salts like hydrofluoric acid salts, hydrochloric acid salts, hydrobromic acid salts and hydroiodic acid salts, nitric acid salts, perchloric acid salts, sulfuric acid salts and phosphoric acid salts; organic acid salts such as lower alkanesulfonic acid salts like methanesulfonic acid salts, trifluoromethanesulfonic acid salts and ethanesulfonic acid salts, arylsulfonic acid salts like benzenesulfonic acid salts and p-toluenesulfonic acid salts, acetic acid salts, malic acid salts, fumaric acid salts, succinic acid salts, citric acid salts, ascorbic acid salts, tartaric acid salts, oxalic acid salts and maleic acid salts; and amino acid salts such as glycine salts, lysine salts, arginine salts, ornithine salts, glutamic acid salts and aspartic acid salts, and hydrohalogenic acid salts (particularly hydrochloric acid salts) are most preferable.

The compound (I) of the present invention or a pharmacologically acceptable salt thereof may absorb moisture when left in air to be changed into a hydrate, and such a hydrate is also embraced in the present invention.

The compound (I) of the present invention or a pharmacologically acceptable salt thereof may be changed into a solvate when left in a solvent, and such a solvate is also embraced in the present invention.

The compound (I) of the present invention or a pharmacologically acceptable salt thereof includes crystalline forms thereof. The crystalline forms of the present invention refer to solids having an internal structure three-dimensionally composed of regularly repeated constituent atoms (or a group thereof), and are distinguished from amorphous solids not having such a regular internal structure.

Even crystals of the same compound may be produced in the form of a plurality of crystalline forms (crystal polymorphs) having different internal structures and physiochemical properties depending on crystallization conditions, and the crystalline form of the present invention may be any one of the crystal polymorphs, or may be a mixture of two or more crystal polymorphs.

The crystalline forms of the present invention may form hydrates by absorbing moisture to have water attached thereto when left in air or by heating to 25 to 150° C. under usual atmospheric conditions. Besides, the crystalline forms of the present invention may contain, as attached residual solvent or a solvate, a solvent used at the time of the crystallization.

In the present description, the crystalline forms of the present invention may sometimes be expressed based on powder X-ray diffraction data. The powder X-ray diffraction, the measurement/diffraction may be performed by methods usually employed in the field of the present invention, and can be performed, for example, by a method described in an example. Besides, in general, a hydrate or a dehydrated form is changed in its lattice constant through attachment/detachment of water of crystallization, which may change a diffraction angle (2θ) in the powder X-ray diffraction. Furthermore, peak intensity may be changed by a difference of a growth surface of the crystal (crystal habit) in some cases. Accordingly, when the crystalline forms of the present invention are expressed based on powder X-ray diffraction data, not only crystals having the same diffraction angle at a peak and X-ray diffraction diagram in powder X-ray diffraction, but also hydrates and dehydrated forms obtained from the crystals, are embraced in the scope of the present invention.

Examples of one aspect of the compound (I) of the present invention include crystalline N-{[4-(difluoromethoxy)phenyl]carbamoyl}-D-isovaline, N-{[4-(difluoromethoxy)-3-fluorophenyl]carbamoyl}-D-isovaline, N-[(4-chlorophenyl) carbamoyl]-D-isovaline, N-[(4-bromophenyl)carbamoyl]-D-isovaline, N-[(4-iodophenyl)carbamoyl]-D-isovaline, (+)-2-{[(3-cyanophenyl)carbamoyl]amino}-2-cyclopropylbutanoic acid, (−)-2-{[(3-cyanophenyl)carbamoyl]amino}-2-cyclopropylbutanoic acid and 2-{[(5-chlorothiophen-3-yl) carbamoyl]amino}-2-ethylbutanoic acid.

A preferable specific example includes crystalline N-{[4-(difluoromethoxy)phenyl]carbamoyl}-D-isovaline having, in powder X-ray diffraction obtained through irradiation with copper Kα radiation (wavelength λ=1.54 angstroms), characteristic peaks at interplanar spacings d of 7.51, 7.33, 6.67, 6.15, 5.32, 5.24, 4.98, 4.79, 3.96 and 3.59 angstroms. This crystalline form presents the powder X-ray diffraction diagram of FIG. 1 through irradiation with copper Kα radiation (wavelength λ=1.54 angstroms).

In each of the powder X-ray diffraction patterns illustrated in FIG. 1 and FIGS. 2 to 8 mentioned below, the ordinate indicates diffraction intensity in count/sec. (CPS), and the abscissa indicates diffraction angle 2θ (degrees). Besides, the interplanar spacing d (unit: angstrom) can be calculated in accordance with an expression, 2d sin θ=nλ with n set to 1.

Another preferable specific example of the present invention includes crystalline N-{[4-(difluoromethoxy)-3-fluorophenyl]carbamoyl}-D-isovaline having, in powder X-ray diffraction obtained through irradiation with copper Kα radiation (wavelength λ=1.54 angstroms), characteristic peaks at interplanar spacings d of 9.52, 6.10, 5.45, 5.29, 4.94, 4.89, 4.75, 3.80, 3.48 and 3.44 angstroms. This crystalline form presents the powder X-ray diffraction diagram of FIG. 2 through irradiation with copper Kα radiation (wavelength λ=1.54 angstroms).

Still another preferable specific example of the present invention includes crystalline N-[(4-chlorophenyl)carbamoyl]-D-isovaline having, in powder X-ray diffraction obtained through irradiation with copper Kα radiation (wavelength λ=1.54 angstroms), characteristic peaks at interplanar spacings d of 15.60, 6.23, 5.68, 5.34, 5.20, 4.59, 4.53, 3.83, 3.37 and 3.15 angstroms. This crystalline form presents the powder X-ray diffraction diagram of FIG. 3 through irradiation with copper Kα radiation (wavelength λ=1.54 angstroms).

Still another preferable specific example of the present invention includes crystalline 2-{[(5-chlorothiophen-3-yl)carbamoyl]amino}-2-ethylbutanoic acid having, in powder X-ray diffraction obtained through irradiation with copper Kα radiation (wavelength λ=1.54 angstroms), characteristic peaks at interplanar spacings d of 15.82, 9.42, 6.53, 5.85, 5.48, 5.24, 4.69, 4.46, 3.58 and 3.12 angstroms. This crystalline form presents the powder X-ray diffraction diagram of FIG. 4 through irradiation with copper Kα radiation (wavelength λ=1.54 angstroms).

Still another preferable specific example of the present invention includes crystalline N-[(4-bromophenyl)carbamoyl]-D-isovaline having, in powder X-ray diffraction obtained through irradiation with copper Kα radiation (wavelength λ=1.54 angstroms), characteristic peaks at interplanar spacings d of 15.82, 6.50, 6.25, 5.39, 4.67, 3.92, 3.86, 3.59, 3.39 and 3.16 angstroms. This crystalline form presents the powder X-ray diffraction diagram of FIG. 5 through irradiation with copper Kα radiation (wavelength λ=1.54 angstroms).

Still another preferable specific example of the present invention includes crystalline N-[(4-iodophenyl)carbamoyl]-D-isovaline having, in powder X-ray diffraction obtained through irradiation with copper Kα radiation (wavelength λ=1.54 angstroms), characteristic peaks at interplanar spacings d of 16.92, 6.62, 4.99, 4.44, 4.30, 4.18, 3.30, 3.21, 3.07 and 3.02 angstroms. This crystalline form presents the powder X-ray diffraction diagram of FIG. 6 through irradiation with copper Kα radiation (wavelength λ=1.54 angstroms).

Still another preferable specific example of the present invention includes crystalline (+)-2-{[(3-cyanophenyl)carbamoyl]amino}-2-cyclopropylbutanoic acid having, in powder X-ray diffraction obtained through irradiation with copper Kα radiation (wavelength λ=1.54 angstroms), characteristic main peaks at interplanar spacings d of 11.30, 8.35, 7.66, 5.64, 5.46, 5.22, 4.73, 4.50, 4.35 and 4.02 angstroms. This crystalline form presents the powder X-ray diffraction diagram of FIG. 7 through irradiation with copper Kα radiation (wavelength λ=1.54 angstroms).

Still another preferable specific example of the present invention includes crystalline (−)-2-{[(3-cyanophenyl)carbamoyl]amino}-2-cyclopropylbutanoic acid having, in powder X-ray diffraction obtained through irradiation with copper Kα radiation (wavelength λ=1.54 angstroms), characteristic peaks at interplanar spacings d of 15.66, 11.62, 11.30, 8.35, 7.80, 6.84, 5.45, 5.22, 4.5 and 4.02 angstroms. This crystalline form presents the powder X-ray diffraction diagram of FIG. 8 through irradiation with copper Kα radiation (wavelength λ=1.54 angstroms).

Since the compound (I) of the present invention has a carboxyl group, a compound obtained by converting the carboxyl group into a pharmacologically acceptable prodrug is also embraced in the present invention. The term "a pharmacologically acceptable prodrug" refers to a compound that is converted into the compound (I) of the present invention through a reaction with an enzyme, a gastric acid or the like under physiological conditions in a living body, namely, a compound changed into the compound (I) of the present invention through enzymatically caused oxidation, reduction, hydrolysis or the like, or a compound changed into the compound (I) of the present invention through hydrolysis or the like caused by gastric acid or the like.

Examples of such a prodrug include compounds obtained through esterification, amidation or the like of the carboxyl group of the compound (I) of the present invention (for example, compounds obtained through ethyl esterification, phenyl esterification, carboxymethyl esterification, dimethylaminomethyl esterification, pivaloyloxymethyl esterification, ethoxycarbonyloxy ethyl esterification, phthalidyl esterification, (5-methyl-2-oxo-1,3-dioxolen-4-yl)methyl esterification, cyclohexyloxy carbonylethyl esterification, sulfate esterification, glucuronidation, glycosidation, galactosidation and methyl amidation of the carboxyl group).

A pharmacologically acceptable prodrug of the compound (I) of the present invention can be easily produced from the compound (I) of the present invention by a known method. Besides, a prodrug of the compound of the present invention includes those changed into the compound (I) of the present invention under physiological conditions described in "Iyakuhin no Kaihatsu (Development of Pharmaceuticals)", vol. 7 Bunshi Sekkei (Molecular Design), pp. 163-198, published by Hirokawa Shoten Co. in 1990.

The compound (I) of the present invention may produce a geometric isomer or a tautomer depending on the selected substituents, and an isolated compound of such isomers and mixtures thereof in an arbitrary ratio are embraced in the present invention.

The compound (I) of the present invention has optical isomers based on asymmetric center(s) in the molecule. Unless otherwise specified, in the compound of the present invention, such isomers and mixtures of such isomers are all represented by a single formula, namely, general formula (I). Accordingly, it is noted that the present invention embraces all of these isomers and mixtures of these isomers.

A mixture of these isomers can be separated by known separation means.

The compound (I) of the present invention can contain an atomic isotope of one or more atoms constituting the compound at a non-natural ratio. Examples of the atomic isotope include deuterium ($^2$H), tritium ($^3$H), iodine-125 ($^{125}$I) and carbon-14 ($^{14}$C). Besides, the compound can be radiolabeled with a radioisotope such as tritium ($^3$H), iodine-125 ($^{125}$I) or carbon-14 ($^{14}$C). The thus radiolabeled compound is useful as a therapeutic or prophylactic agent, a research reagent such as an assay reagent, and a diagnostic agent such as an in vivo image diagnostic agent. It is noted that all isotopic variants of the compound of the present invention are embraced in the scope of the present invention no matter whether or not they are radioactive.

Advantageous Effects of Invention

The compound (I) of the present invention or a pharmacologically acceptable salt thereof has excellent tryptophanase inhibitory function and is useful as an agent for reducing indoxyl sulfate in the blood, an agent for preventing or treating a disease caused by an increase in indoxyl sulfate in the blood, an agent for delaying transition to renal replacement therapy in a patient in a period of conservative treatment of chronic kidney disease, and an agent for suppressing worsening of remaining renal function in a patient after transition to renal replacement therapy.

DESCRIPTION OF EMBODIMENTS

Figure 1:
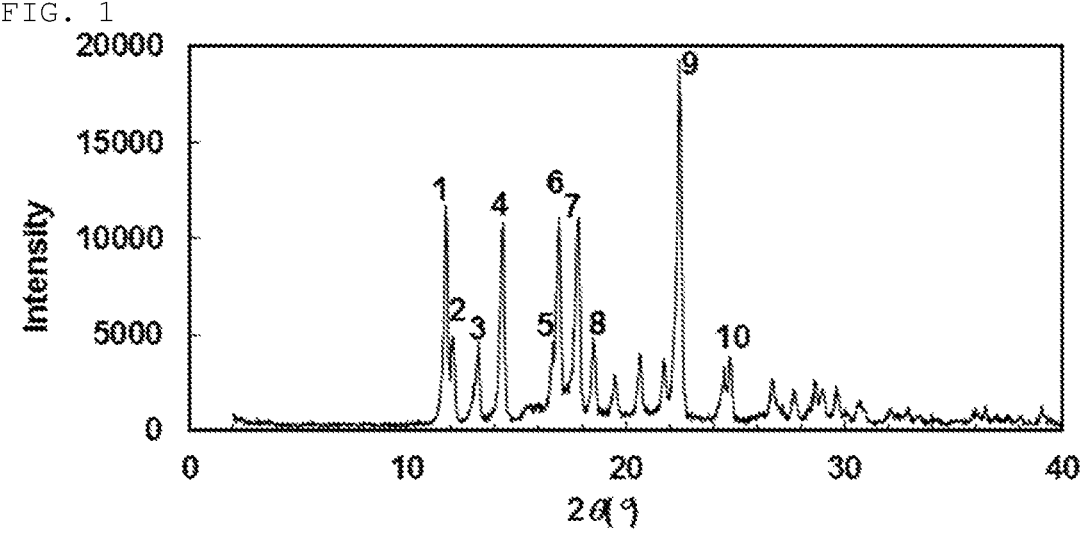
FIG. 1 is a powder X-ray diffraction diagram of crystals obtained in Example 8. The ordinate indicates diffraction intensity in count/sec. (cps), and the abscissa indicates a value of diffraction angle 2θ.

Now, representative methods for producing the compound (I) of the present invention and starting compounds used in the production of the compound (I) of the present invention will be described, and it is noted that the present invention is not limited to these methods.

Production Method 1

The compound of the present invention and pharmacologically acceptable salts thereof can be produced by applying a variety of known synthesis methods based on the characteristics of the basic structure or the type of substituent(s) of the compound to be produced.

Depending on the type of a functional group, it may be effective in terms of production technology, in some cases, to replace the functional group with an appropriate protective group (a group that can be easily converted into the functional group) at a stage from raw material to intermediate. Examples of such protective groups include protective groups described in Greene's Protective Groups in Organic Synthesis, written by P. G. M. Wuts and T. W. Greene (4th edition, 2006), and the protective group may be appropriately selected in accordance with reaction conditions for these.

In such a method, a reaction is performed by introducing the protective group, and then, the protective group is removed if necessary, and thus a desired compound can be obtained. Besides, a prodrug of the compound of the present invention can be produced, at a stage from raw material to intermediate similarly to the protective group, by introducing a specific group or by further performing a reaction using a resultant compound. The reaction can be performed by applying a usual method of esterification, amidation, dehydration or the like.

[Method A]

Method A is a method for producing the compound (I) of the present invention.

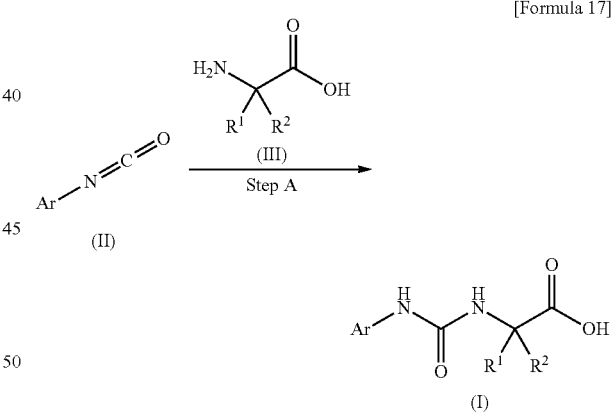

[Formula 17]

In the formula, $R^1$, $R^2$ and Ar are as defined above.

(Step A) Step of Forming Urea

This step is a step of producing the compound (I) of the present invention by reacting a compound (II) with a compound (III) in the presence of a base.

In this step, usually, the reaction temperature is 0° C. to room temperature, and the reaction time is 1 to 24 hours.

Examples of the base used in this step include a tertiary amine such as triethylamine or N,N-diisopropylethylamine; an aqueous solution of an inorganic base such as potassium carbonate or sodium hydrogen carbonate; or an aqueous solution of an alkali metal hydroxide such as sodium hydroxide or potassium hydroxide, and an aqueous solution of an alkali metal hydroxide is preferable.

As a solvent used in this step, a halogenated solvent such as dichloromethane; an ether such as tetrahydrofuran; acetonitrile; or a mixed solvent of any of these is preferred.

In this step, the reaction can also be performed in the absence of a base. For example, the compound (II) may be added to an acetonitrile suspension of the compound (III) at room temperature for performing the reaction. Usually, the reaction temperature is about 0° C. to 80° C., and the reaction time is about 1 hour to 24 hours.

The compound (II) can be obtained as a commercially available product, or can be produced by a method described later.

Besides, the compound (III) can be obtained as a commercially available product, or can be produced by a known method (for example, Tetrahedron: Asymmetry, 2007, 18, 569-623) or an equivalent method.

[Method B]

Method B is a method for producing the compound (II) used in the method A.

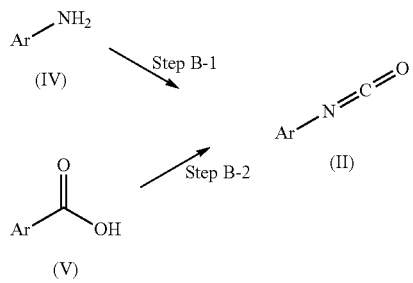

[Formula 18]

In this formula, Ar is as defined above.

(Step B-1) Isocyanation Step

This step is a step of isocyanating a compound (IV) through a reaction with phosgene, triphosgene or the like performed in the presence or absence of a base.

The base used in this step is preferably triethylamine or the like, and as a solvent, toluene, 1,4-dioxane, dichloromethane or a mixed solvent of these is usually used.

In this step, the reaction temperature is usually 0° C. to 100° C., and the reaction time is usually about 1 hour to 24 hours.

(Step B-2) Isocyanation Step Through Curtius Rearrangement

This is a step of producing the compound (III) through thermal decomposition after acyl-azidating a carboxylic acid of a compound (V) through a reaction with diphenylphosphoryl azide performed in the presence of a base.

As a solvent used in this step, not only an aromatic hydrocarbon-based solvent such as toluene but also any of various solvents such as tetrahydrofuran and N,N-dimethylformamide can be used.

In this step, usually, the reaction temperature is room temperature to about 110° C., and the reaction time is 1 hour to 12 hours.

The compounds (IV) and (V) can be obtained as commercially available products, or can be produced by a known method (for example, the 4th series of experimental chemistry 20 and 22, edited by Chemical Society of Japan), or an equivalent method.

[Method C]

Method C is a method for producing the compound (I) of the present invention, and is an alternative method to the method A.

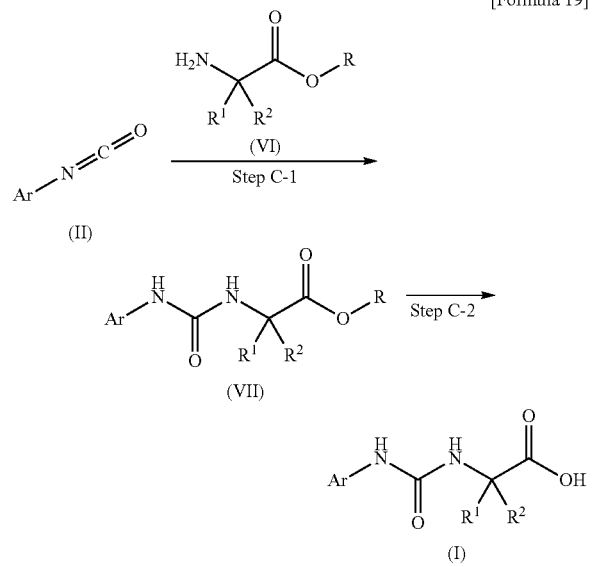

[Formula 19]

In the formula, $R^1$, $R^2$ and Ar are as defined above, and R represents a methyl group, an ethyl group, a propyl group, a t-butyl group or a benzyl group.

(Step C-1) Step of Forming Urea

This step is a step of obtaining a compound (VII) by reacting the compound (II) with a compound (VI) having a protected carboxylic acid moiety.

As a solvent used in this step, not only an ether such as tetrahydrofuran but also any of various solvents such as N,N-dimethylformamide, dichloromethane and acetonitrile can be used.

In this step, the reaction temperature is usually about 0° C. to 70° C., and the reaction time is usually about 0.2 hours to 12 hours.

The compound (II) can be obtained as a commercially available product, or can be produced by the method B described above.

Besides, the compound (VI) can be obtained as a commercially available product, or can be produced by a method described below.

(Step C-2) Step of Hydrolyzing Ester

This step is a step of obtaining the compound (I) of the present invention by hydrolyzing an ester group of the compound (VII) in a solvent in the presence of a base.

The base used in this step is preferably an alkali metal hydroxide such as sodium hydroxide or potassium hydroxide, and the solvent used is preferably a mixed solvent of water and tetrahydrofuran/methanol, or the like.

In this step, the reaction temperature is usually about room temperature to 80° C., and the reaction time is usually about 1 hour to 24 hours.

In this step, when the group R is a benzyl group, the reaction can usually be performed in an alcohol solution such as methanol under a hydrogen atmosphere and in the presence of a catalyst such as 10% palladium/carbon.

In this step, when the group R is a t-butyl group, the reaction can be performed in a dichloromethane solution with trifluoroacetic acid added.

[Method D]

Method D is a method for producing a compound corresponding to the compound (VI) used in the method C.

[Formula 20]

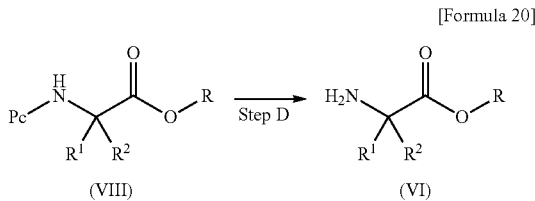

In this formula, $R^1$, $R^2$ and R are as defined above, and Pc represents a protective group of an amino group such as a tert-butoxycarbonyl group.

(Step D) Deprotection Step

This step is a step of obtaining the compound (VI) by performing a reaction under usual conditions for deprotection of an amino group.

In this step, when the protective group of the amino group is a tert-butoxycarbonyl group, the reaction is usually performed in a methylene chloride solution with trifluoroacetic acid added.

In this step, the reaction temperature is usually about room temperature, and the reaction time is usually about 1 hour.

A compound (VIII) can be obtained as a commercially available product, or can be produced by appropriately protecting the compound (III) by a method described in Greene's Protective Groups in Organic Synthesis, written by P. G. M. Wuts and T. W. Greene (4th edition, 2006).

[Method E]

Method E is a method for producing the compound (I-a) of the present invention, and is an alternative method to the methods A and C. When a substituent in position 4 of the benzene ring of the starting compound (IX) is a bromine atom, a group such as $C_3$-$C_5$ saturated cyclic amino group, a halogeno $C_3$-$C_5$ saturated cyclic amino group or di($C_1$-$C_3$ alkyl)amino group can be introduced by substitution through steps E-1, E-2, E-3 and E-4.

[Formula 21]

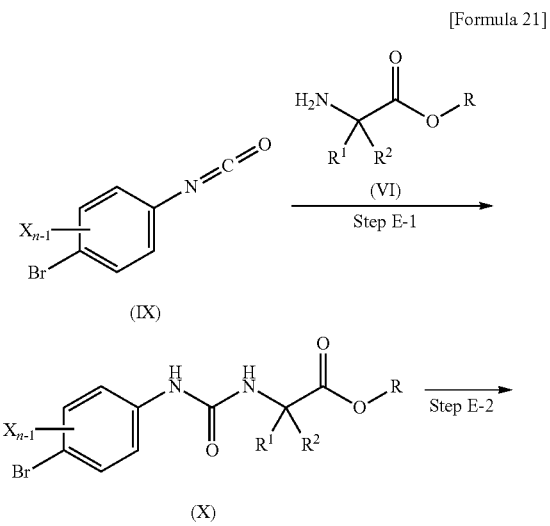

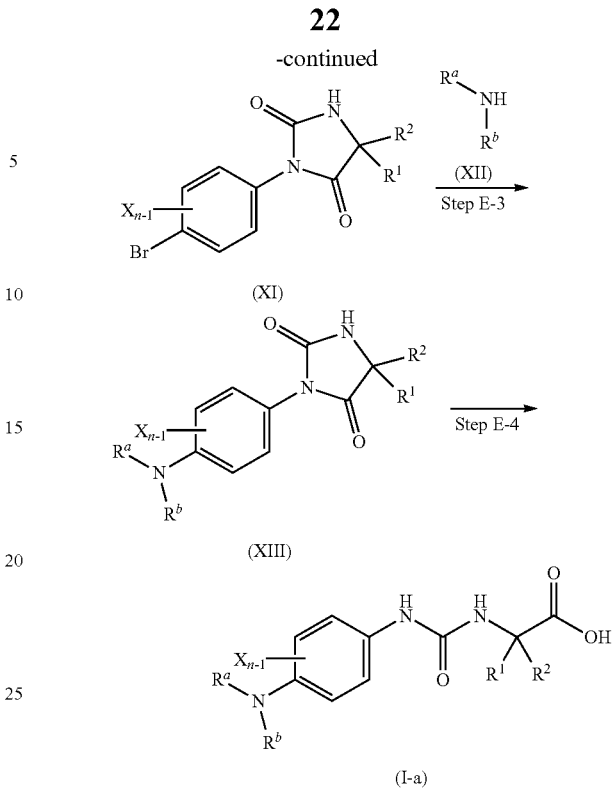

In the formula, $R^1$, $R^2$, R and X are as defined above, n represents 1 or 2, and the group $NR^aR^b$ represents a saturated cyclic amino group, a halogeno saturated cyclic amino group or a di($C_1$-$C_3$ alkyl) amino group.

(Step E-1) Step of Forming Urea

This step is a step of performing production under conditions similar to those of the step C-1 of the method C.

(Step E-2) Step of Forming Cyclized Product

This step is a step of obtaining a compound (XI) by cyclizing the compound (X) in a molecule in the presence of a base.

The base used in this step is preferably an alkali metal hydroxide such as sodium hydroxide or potassium hydroxide, and the solvent used is preferably a mixed solvent of water and tetrahydrofuran/methanol or the like.

In this step, the reaction temperature is usually about room temperature, and the reaction time is usually about 1 hour to 24 hours.

(Step E-3) Step of Producing Compound (XIII) Through Coupling Reaction

This step is a step of producing a compound (XIII) from the compound (XI) and a compound (XII) through a Buchwald-Hartwig cross-coupling reaction.

In this step, the reaction is performed in a solvent in the presence of a catalyst, a ligand and a base.

Examples of the catalyst used in this step include chloro(2-dicyclohexylphophino-2',6'-diisopropoxy-1,1'-biphenyl)[2-(2-aminoethylphenyl)]palladium (II), palladium acetate or tris(dibenzylideneacetone)dipalladium (0).

Examples of the ligand used in this step include 2-dicyclohexylphosphino-2',6'-diisopropoxybiphenyl, 2-(dicyclohexylphosphino)-3,6-dimethoxy-2',4',6'-triisopropyl-1,1'-biphenyl or 2-dicyclohexylphosphino-2',4',6'-triisopropylbiphenyl.

Examples of the base used in this step include cesium carbonate, sodium tert-butoxide or lithium bis(trimethylsilyl)amide.

Examples of the solvent used in this step include aromatic hydrocarbons such as toluene; or ethers such as tetrahydrofuran and 1,4-dioxane.

In this step, the reaction temperature is usually room temperature to 110° C., and the reaction time is usually about 1 hour to 24 hours.

The compound (XII) can be obtained as a commercially available product.

(Step E-4) Step of Hydrolyzing Hydantoin

This step is a step of obtaining the compound (I-a) of the present invention by hydrolyzing the compound (XIII) in a solvent in the presence of a base.

The base used in this step is preferably an alkali metal hydroxide such as sodium hydroxide or potassium hydroxide, and the solvent used is preferably a mixed solvent of water and tetrahydrofuran/methanol or the like.

In this step, the reaction temperature is usually about room temperature to 80° C., and the reaction time is usually about 1 hour to 24 hours.

[Method F]

Method F is a method for producing the compound (I-b) of the present invention, and is an alternative method to the methods A and C. When the substituent in position 4 of the benzene ring of the starting compound (IX) is a bromine atom, a group such as a phenyl group or a halogeno phenyl group can be introduced by substitution through steps E-1, E-2, F-1 and F-2.

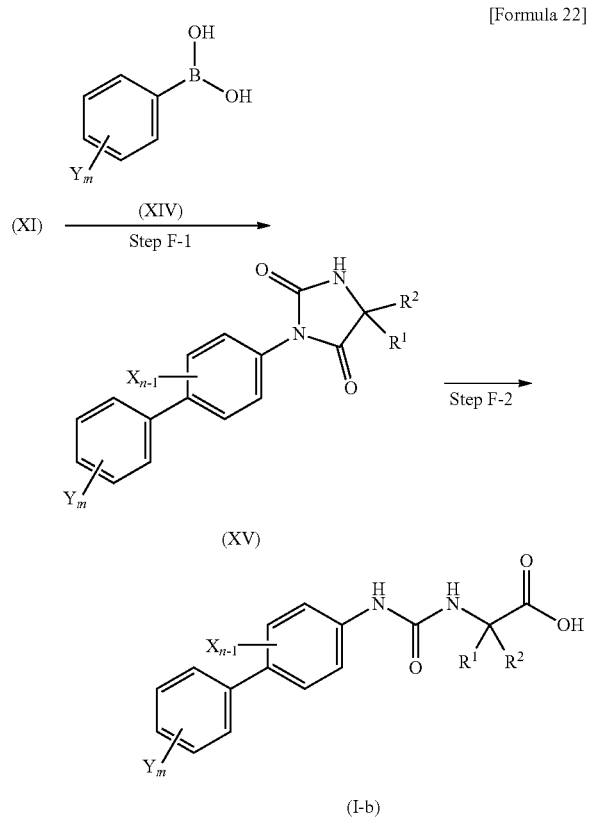

[Formula 22]

In the formula, $R^1$, $R^2$, X and n are as defined above, Y represents a halogen atom, and m represents 0, 1, 2, 3, 4 or 5.

(Step F-1) Step of Producing Compound (XV) Through Coupling Reaction

This step is a step of producing a compound (XV) from the compound (XI) and a compound (XIV) through a Suzuki-Miyaura Cross-coupling reaction.

In this step, the reaction is performed in a solvent in the presence of a catalyst and a base.

Examples of the catalyst used in this step include catalysts containing various transition metals and various ligands such as tetrakis triphenylphosphine palladium (0), bis(triphenylphosphine)palladium (II) dichloride and chloro(2-dicyclohexylphosphino-2',4',6'-triisopropyl-1,1'-biphenyl)[2-(2'-amino-1,1'-biphenyl)palladium (II).

The base used in this step is, for example, potassium phosphate, potassium acetate or potassium carbonate.

Examples of the solvent used in this step include 1,2-dimethoxyethane, tetrahydrofuran, and a mixed solvent of an ether such as 1,4-dioxane and water.

In this step, the reaction temperature is room temperature to 100° C.

In this step, the reaction time is about 1 hour to 24 hours.

The compound (XIV) can be obtained as a commercially available product.

(Step F-2) Step of Hydrolyzing Hydantoin

This is a step of performing production under conditions similar to those of the step E-4 of the method E.

A compound produced by the above-described method can be isolated and purified by a known method, such as extraction, precipitation, distillation, chromatography, fractional crystallization or recrystallization.

Besides, when the compound or a production intermediate has asymmetric carbon(s), it has optical isomers. Such optical isomers can be isolated and purified by a usual method such as fractional crystallization by recrystallizing with an appropriate salt (salt resolution) or column chromatography. For a method for resolving an optical isomer from a racemate, "Enantiomers, Racemates and Resolution, John Wiley And Sons, Inc." written by J. Jacques et al. can be referred to.

The compound (I) of the present invention or a pharmacologically acceptable salt thereof can reduce indoxyl sulfate in the blood. In the present invention, the term "reduce indoxyl sulfate in the blood" refers to reducing indoxyl sulfate concentration in human blood as compared with a value obtained before administering the compound of the present invention, and preferably reducing the indoxyl sulfate concentration in human blood as compared with a value obtained before administering the compound of the present invention by 0.1 mg/dL or more. For example, the indoxyl sulfate concentration in the blood of a kidney disease patient in CKD-stage 4, which is 0.45 md/dL on average, is reduced preferably to 0.24 mg/dL, that is, to the concentration of a kidney disease patient in CKD-stage 3; is reduced more preferably to 0.13 mg/dL, that is, to the concentration of a kidney disease patient in CKD-stage 2; and is reduced most preferably to 0.075 mg/dL, that is, to the level in a human not suffering from kidney disease. The indoxyl sulfate concentration in the blood of a terminal kidney disease patient including a dialysis patient in CKD-stage 5, which is 1.30 md/dL on average, is reduced preferably to 0.45 mg/dL, that is, to the concentration of a kidney disease patient in CKD-stage 4; is reduced more preferably to 0.24 mg/dL, that is, to the concentration of a kidney disease patient in CKD-stage 3; is reduced further more preferably to 0.13 mg/dL, that is, to the concentration of a kidney disease patient in CKD-stage 2; and is reduced most preferably to 0.075 mg/dL, that is, to the level in a human not suffering from kidney disease (ELLIS-RJ Nephrology 21 170-177 (2016)). The concentration of indoxyl sulfate in the blood can be quantitatively determined by singly employing liquid chromatography (fluorescence detection) or its combination with a mass spectrometer used successively.

The compound (I) of the present invention or a pharmacologically acceptable salt thereof can suppress worsening of renal function. In the present invention, the term "suppress worsening of renal function" refers to reducing leakage of protein such as albumin into urine, suppressing deterioration of GFR (glomerular filtration rate), or suppressing an increase in a biochemical marker in the blood and urine reflecting dysfunction of the kidney.

The compound (I) of the present invention or a pharmacologically acceptable salt thereof can prevent or treat a disease caused by an increase in indoxyl sulfate in the blood. In the present invention, the term "a disease caused by an increase in indoxyl sulfate in the blood" refers to chronic kidney disease (CKD), renal anemia, obstructive arteriosclerosis or ischemic heart disease, and is particularly chronic kidney disease.

In the present invention, the term "prevent" refers to reducing the probability of developing a disease caused by an increase in indoxyl sulfate in the blood. For example, when the disease caused by an increase in indoxyl sulfate in the blood is CKD, it refers to the probability of developing CKD in the future for a person with normal renal function having a soluble urokinase plasminogen activator receptor (suPAR) concentration in the blood of 4020 pg/mL or higher being reduced as compared with that of a person with normal renal function having a suPAR concentration in the blood lower than 2373 pg/mL (by three times or more, HR: 3.13: Hayek-S S, N Engl J Med 373: 1916-1925, 2015). The probability of developing CKD can be checked based on whether an estimated GFR<60 mL/min/1.73 m$^2$.

In the present invention, the term "treat" refers to suppressing advance or progression of pathological conditions of a disease caused by an increase in indoxyl sulfate in the blood, or improving the pathological conditions.

When the disease caused by an increase in indoxyl sulfate in the blood is CKD, the term "suppress advance or progression" refers to preventing an increase in leakage of protein such as albumin into urine, maintaining the GFR, and maintaining or suppressing an increase in a biochemical marker in the blood and urine reflecting the dysfunction of the kidney. It can be checked, for example, whether proteinuria of 0.3 g/gCr and albuminuria of 100 mg/gCr or more of a CKD patient is maintained for 6 months to 1 year, or by maintaining an eGFR of 30 mL/min/1.73 m$^2$ of a CKD patient for 6 months to 1 year. The term "improve pathological conditions" refers to lowering severity of CKD to a lower rank. For example, it can be checked whether albumin in urine of 0.6 g/gCr is reduced to 0.3 g/gCr (the severity of CKD is thus lowered from A3 to A2). Besides, it can also be checked whether a GFR of 25 mL/min/1.73 m$^2$ is increased to 35 mL/min/1.73 m$^2$ (the severity of CKD is thus lowered from G4 to G3b).

The compound (I) of the present invention or a pharmacologically acceptable salt thereof can delay transition to renal replacement therapy in a patient in a period of conservative treatment of chronic kidney disease.

In the present invention, the term "conservative treatment of chronic kidney disease" refers, in a patient having been diagnosed as having chronic kidney disease, to preventing the gradually deteriorating renal function after the diagnosis from further deteriorating by reducing the burden on the kidney having deteriorated function, or by reducing damage to other organs caused by the deteriorated renal function.

In the present invention, the term "delay transition to renal replacement therapy in a patient in a period of conservative treatment of chronic kidney disease" refers to extending the period until a criterion for introducing hemodialysis, introducing peritoneal dialysis or practicing preemptive kidney transplant is satisfied. For example, in the case of a chronic kidney disease patient for which it is planned to introduce peritoneal dialysis, it refers to extending the period until GFR, which is used as a criterion for the introduction, is lowered to about 6 mL/min/1.73 m$^2$.

The compound (I) of the present invention or a pharmacologically acceptable salt thereof can suppress worsening of remaining renal function in a patient after transition to renal replacement therapy. In the present invention, the term "worsening of remaining renal function in a patient after transition to renal replacement therapy" refers to, for example, reducing the urine amount per day after introducing dialysis as compared with that before the introduction, and specifically, reducing the urine amount that was 400 mL or more per day before introducing dialysis down to less than 400 mL after the introduction. The worsening of remaining renal function can be evaluated also by measuring creatinine clearance or a Kt/V value {(urea concentration in urine)/(urea concentration in the blood)×(urine amount per day)×7 days}.

In the present invention, the term "suppress worsening of remaining renal function in a patient after transition to renal replacement therapy" refers to avoiding anuria. For example, when peritoneal dialysis (PD) is practiced before hemodialysis (HD) for the purpose of maintaining and not reducing a urine amount of 20 mL/day for 6 months to 1 year, or further maintaining remaining renal function, it can be checked whether or not a period of the PD before transition to the HD can be further extended.

An example of a dosage form of the compound (I) of the present invention or a pharmacologically acceptable salt thereof includes oral administration with a tablet, a granule, a powder, a capsule or a syrup.

Examples of an oral pharmaceutical form of the compound (I) of the present invention or a pharmacologically acceptable salt thereof include a tablet (including an orally disintegrating tablet), a pill, a granule, a powder, a capsule, a solution (including a spray), a suspension, an emulsion, a syrup, a paste and an elixir. A pharmaceutical in such a form can be prepared in accordance with a usual method by using an additive appropriately selected, if necessary, from pharmaceutically acceptable additives such as an excipient, a binder, a diluent, a stabilizer, a preservative, a colorant, a dissolution assisting agent, a suspending agent, a buffer or a humectant.

The dose of a formulation of the present invention is varied depending on the symptom, the age, the weight and the like, and is 0.1 to 1000 mg, preferably 1 to 300 mg, per adult once or several times a day. The formulation of the present invention can be administered to a non-human mammal.

The inventive compound or a pharmacologically acceptable salt thereof can be used together with another drug. Examples of concomitant drugs that can be used include, for example, a cardiovascular drug such as an angiotensin II receptor antagonist, an angiotensin-converting enzyme inhibitor, a calcium antagonist, a diuretic and a spherical carbonaceous adsorbent, and those used in the drug therapy of a chronic kidney disease patient, and also include a large number of oral drugs including those prescribed based on a comorbid disease and the primary disease, such as a therapeutic drug for hyperuricemia, a therapeutic drug for hyperlipidemia, a therapeutic drug for diabetes, a steroid/immunosuppressive agent, an antiplatelet drug/anticoagulation drug, a therapeutic drug for hyperphosphatemia, an erythropoiesis stimulating factor preparation, an analgesic, an antiarrhythmic drug, an antidepressant, a therapeutic drug for dementia of Alzheimer type, a Parkinson's disease drug, a proton pump inhibitor (PPI), an antiallergic agent, an antibacterial and an OTC pharmaceutical.

The "angiotensin II receptor antagonist" corresponds to losartan, candesartan, valsartan, telmisartan, olmesartan, irbesartan, azilsartan and the like.

The "angiotensin-converting enzyme inhibitor" corresponds to captopril, enalapril, alacepril, delapril, cilazapril, lisinopril, benazepril, imidapril, temocapril, quinapril, trandolapril, perindopril erbumine and the like.

The "calcium antagonist" corresponds to nifedipine, amlodipine, efonidipine, cilnidipine, nicardipine, nisoldipine, nitrendipine, nilvadipine, barnidipine, felodipine, benidipine, manidipine, azelnidipine, aranidipine, diltiazem and the like.

The "diuretic" corresponds to trichlormethiazide, benzylhydrochlorothiazide, hydrochlorothiazide, meticrane, indapamide, tripamide, mefruside, furosemide, triamteren and the like.

Besides, the compound of the present invention or a pharmacologically acceptable salt thereof can be formed into a combination drug with any of the above-described therapeutic drugs to be concomitantly used. A blending ratio with the concomitant drug can be arbitrarily set, and usually the blending ratio between the inventive compound or a pharmacologically acceptable salt thereof and the therapeutic drug to be concomitantly used is, in a weight ratio, usually 1:0.0001 to 200, and particularly preferably 1:0.001 to 10.

The present invention will now be described in more detail with reference to examples, test examples and formulation examples, and it is noted that the scope of the present invention is not limited to these examples.

EXAMPLES

The present invention will now be described in more detail with reference to examples and test examples, and it is noted that the scope of the present invention is not limited to these examples.

Elution in column chromatography in each example was performed under observation by TLC (thin layer chromatography). In the TLC observation, silica gel 60F$_{254}$ manufactured by Merck was used as a TLC plate, the solvent used as an elution solvent in column chromatography was used as a developing solvent, and a UV detector was employed as a detection method. For the column chromatography, an automated chromatograph (Purif-α2) manufactured by Shoko Scientific Co., Ltd. was used. The elution solvent was determined based on the TLC observation.

In the examples described below, nuclear magnetic resonance (hereinafter referred to as $^1$H NMR) spectra were indicated in δ values (ppm) in terms of chemical shift values with tetramethylsilane used as a reference material. Splitting patterns were represented by s for singlet, d for doublet, t for triplet, q for quartet, m for multiplet and br for broad.

Mass analysis (hereinafter referred to as MS) was carried out by an API (atmospheric pressure ionization) method.

Example 1

2-Ethyl-2-({[4-(trifluoromethoxy)phenyl]carbamoyl}amino)butanoic acid

[Formula 23]

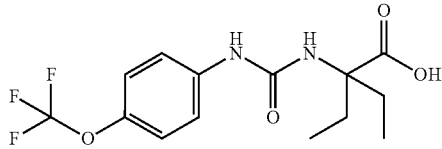

To a water (10 mL) suspension of 2-amino-2-ethylbutanoic acid (CAS Registry Number: 2566-29-2) (0.65 g, 4.96 mmol), a 1N sodium hydroxide solution (5.00 mL, 5.00 mmol), dichloromethane (20 mL) and 1-isocyanato-4-(trifluoromethoxy)benzene (CAS Registry Number: 35037-73-1) (2.00 g, 9.85 mmol) were added, followed by stirring at room temperature overnight. Ethyl acetate was added to the resultant, an organic layer and an aqueous layer were separated, and then, the aqueous layer was acidified with dilute hydrochloric acid and extracted with ethyl acetate. The thus obtained extract was dried over anhydrous sodium sulfate, filtered and concentrated under reduced pressure. A solid produced by adding a mixed solvent of ethyl acetate/n-hexane to the resultant residue was filtered and dried under reduced pressure to obtain 498 mg (30%) of the title compound in the form of a white solid.

$^1$H-NMR (500 MHz, DMSO-D$_6$) δ: 13.02 (1H, br s), 9.11 (1H, s), 7.44-7.41 (2H, m), 7.18 (2H, d, J=8.8 Hz), 6.37 (1H, s), 2.25-2.17 (2H, m), 1.73-1.65 (2H, m), 0.71 (6H, t, J=7.3 Hz).

MS m/z: 335 (M+H)$^+$.

Example 2

2-Cyclopropyl-2-({[4-(trifluoromethoxy)phenyl]carbamoyl}amino)propanoic acid

[Formula 24]

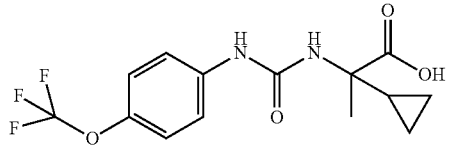

In the same manner as in Example 1, 0.43 g (43%) of the title compound was obtained in the form of a white solid from 2-amino-2-cyclopropylpropanoic acid (CAS Registry Number: 5687-72-9) (0.39 g, 3.02 mmol), a 1N sodium hydroxide solution (3.00 mL, 3.00 mmol) and 1-isocyanato-4-(trifluoromethoxy)benzene (CAS Registry Number: 35037-73-1) (0.84 g, 4.14 mmol).

$^1$H-NMR (400 MHz, DMSO-D$_6$) δ: 12.29 (1H, br s), 8.70 (1H, s), 7.42-7.38 (2H, m), 7.18 (2H, d, J=9.0 Hz), 6.39 (1H, s), 1.25 (3H, s), 1.25-1.17 (1H, m), 0.44-0.34 (4H, m).

MS m/z: 333 (M+H)$^+$.

Example 3

2-Methyl-N-{[4-(trifluoromethoxy)phenyl]carbamoyl}leucine

[Formula 25]

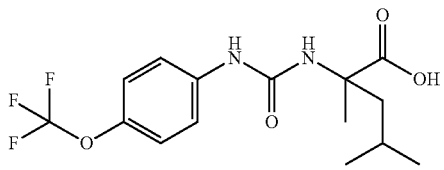

To a 1N sodium hydroxide (0.83 mL, 0.83 mmol) solution of 2-methylleucine (CAS Registry Number: 144-24-1) (100 mg, 0.69 mmol), a dichloromethane (3 mL) solution of 1-isocyanato-4-(trifluoromethoxy)benzene (CAS Registry Number: 35037-73-1) (280 mg, 1.38 mmol) was added, followed by stirring at room temperature for 4 hours. Ethyl acetate, water and a 1N sodium hydroxide solution (0.83 mL) were added to the resultant, and an organic layer and an aqueous layer were separated. A solid obtained by acidifying the aqueous layer with 2N hydrochloric acid was filtered, washed successively with water and n-hexane, and dried under reduced pressure to obtain 199 mg (83%) of the title compound in the form of a white solid.

$^{1}$H-NMR (400 MHz, DMSO-D$_{6}$) δ: 12.93 (1H, br s), 9.00 (1H, s), 7.46-7.41 (2H, m), 7.20 (2H, d, J=9.0 Hz), 6.52 (1H, s), 2.08 (1H, dd, J=13.3, 4.7 Hz), 1.66-1.56 (2H, m), 1.47 (3H, s), 0.86 (3H, d, J=6.3 Hz), 0.83 (3H, d, J=6.6 Hz).

MS m/z: 349 (M+H)$^{+}$.

Example 4

(−)-N-{[4-(Trifluoromethoxy)phenyl]carbamoyl}-D-isovaline

[Formula 26]

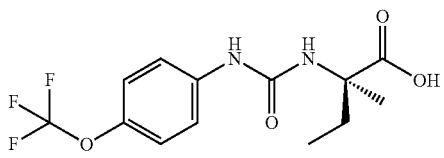

To a 1N sodium hydroxide (1.02 mL, 1.02 mmol) solution of D-isovaline (CAS Registry Number: 3059-97-0) (100 mg, 0.85 mmol), a dichloromethane (3 mL) solution of 1-isocyanato-4-(trifluoromethoxy)benzene (CAS Registry Number: 35037-73-1) (347 mg, 1.71 mmol) was added, followed by stirring at room temperature overnight. Ethyl acetate, water and a 1N sodium hydroxide solution (1.02 mL) were added to the resultant, and an organic layer and an aqueous layer were separated. A solid obtained by acidifying the aqueous layer with 2N hydrochloric acid was filtered, washed successively with water and n-hexane, and dried under reduced pressure to obtain 187 mg (68%) of the title compound in the form of a white solid.

$^{1}$H-NMR (400 MHz, DMSO-D$_{6}$) δ: 12.66 (1H, br s), 8.87 (1H, s), 7.48-7.44 (2H, m), 7.23-7.22 (2H, m), 6.47 (1H, s), 2.01-1.92 (1H, m), 1.81-1.72 (1H, m), 1.45 (3H, s), 0.81 (3H, t, J=7.4 Hz).

MS m/z: 321 (M+H)$^{+}$.

$[α]_{D}^{25}$ −8.12° (c 0.5, Methanol).

Example 5

Dicyclopropyl({[4-(trifluoromethoxy)phenyl]carbamoyl}amino)acetic acid

[Formula 27]

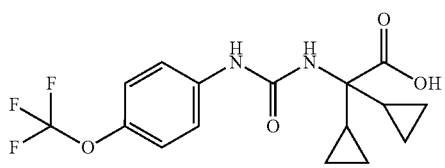

To a 1N sodium hydroxide (0.77 mL, 0.77 mmol) solution of amino(dicyclopropyl)acetic acid (CAS Registry Number: 6321-21-7) (100 mg, 0.64 mmol), a dichloromethane (3 mL) solution of 1-isocyanato-4-(trifluoromethoxy)benzene (CAS Registry Number: 35037-73-1) (262 mg, 1.29 mmol) was added, followed by stirring at room temperature for 4 hours. Ethyl acetate, water and a 1N sodium hydroxide solution (0.77 mL) were added to the resultant, and an organic layer and an aqueous layer were separated. A solid obtained by acidifying the aqueous layer with 2N hydrochloric acid was filtered, washed successively with water and n-hexane, and dried under reduced pressure to obtain 143 mg (62%) of the title compound in the form of a white solid.

$^{1}$H-NMR (400 MHz, DMSO-D$_{6}$) δ: 12.23 (1H, br s), 8.69 (1H, s), 7.41-7.37 (2H, m), 7.18 (2H, d, J=9.0 Hz), 6.12 (1H, s), 1.26-1.19 (2H, m), 0.45-0.30 (8H, m).

MS m/z: 359 (M+H)$^{+}$.

Example 6

2-Ethyl-N-{[4-(trifluoromethoxy)phenyl]carbamoyl}norvaline

[Formula 28]

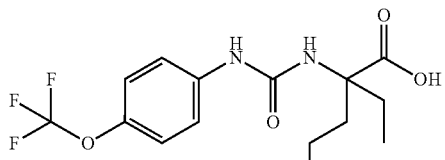

To a 1N sodium hydroxide (1.21 mL, 1.21 mmol) solution of 2-ethylnorvaline hydrochloride (CAS Registry Number: 1129277-25-3) (100 mg, 0.55 mmol), a dichloromethane (3 mL) solution of 1-isocyanato-4-(trifluoromethoxy)benzene (CAS Registry Number: 35037-73-1) (224 mg, 1.10 mmol) was added, followed by stirring at room temperature for 2.5 hours. Ethyl acetate, water and a 1N sodium hydroxide solution (0.66 mL) were added to the resultant, and an organic layer and an aqueous layer were separated. A solid obtained by acidifying the aqueous layer with 2N hydrochloric acid was filtered, washed successively with water and n-hexane, and dried under reduced pressure to obtain 88 mg (46%) of the title compound in the form of a white solid.

$^1$H-NMR (400 MHz, DMSO-D$_6$) δ: 13.05 (1H, br s), 9.10 (1H, s), 7.45-7.39 (2H, m), 7.17 (2H, d, J=9.0 Hz), 6.38 (1H, s), 2.26-2.14 (2H, m), 1.71-1.58 (2H, m), 1.27-1.18 (1H, m), 1.07-0.97 (1H, m), 0.81 (3H, t, J=7.2 Hz), 0.69 (3H, t, J=7.4 Hz).

MS m/z: 349 (M+H)$^+$.

Example 7

2-Cyclopropyl-2-({[4-(trifluoromethoxy)phenyl]carbamoyl}amino)butanoic acid

[Formula 29]

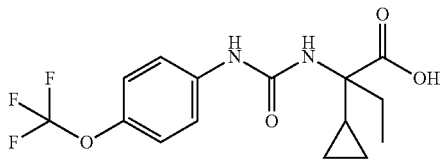

To a 1N sodium hydroxide (0.61 mL, 0.61 mmol) solution of 2-amino-2-cyclopropylbutanoic acid hydrochloride (CAS Registry Number: 1864016-20-5) (50 mg, 0.28 mmol), a dichloromethane (3 mL) solution of 1-isocyanato-4-(trifluoromethoxy)benzene (CAS Registry Number: 35037-73-1) (170 mg, 0.83 mmol) was added, followed by stirring at room temperature overnight. Ethyl acetate, water and a 1N sodium hydroxide solution (0.33 mL) were added to the resultant, and an organic layer and an aqueous layer were separated. A solid obtained by acidifying the aqueous layer with 2N hydrochloric acid was filtered, washed successively with water and n-hexane, and dried under reduced pressure to obtain 59 mg (61%) of the title compound in the form of a white solid.

$^1$H-NMR (400 MHz, DMSO-D$_6$) δ: 12.74 (1H, br s), 8.93 (1H, s), 7.42-7.38 (2H, m), 7.17 (2H, d, J=9.0 Hz), 6.18 (1H, s), 2.25-2.16 (1H, m), 1.98-1.90 (1H, m), 1.30-1.23 (1H, m), 0.77 (3H, t, J=7.4 Hz), 0.42-0.27 (4H, m).

MS m/z: 347 (M+H)$^+$.

Example 8

(−)-N-{[4-(Difluoromethoxy)phenyl]carbamoyl}-D-isovaline

[Formula 30]

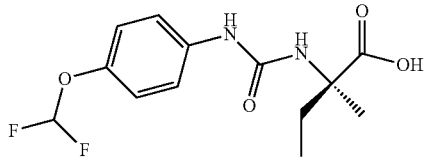

To a 1N sodium hydroxide (1.02 mL, 1.02 mmol) solution of D-isovaline (CAS Registry Number: 3059-97-0) (100 mg, 0.85 mmol), a dichloromethane (3 mL) solution of 1-(difluoromethoxy)-4-isocyanatobenzene (CAS Registry Number: 58417-15-5) (316 mg, 1.71 mmol) was added, followed by stirring at room temperature for 3.5 hours. Ethyl acetate, water and a 1N sodium hydroxide solution (1.02 mL) were added to the resultant, an organic layer and an aqueous layer were separated, and then, the aqueous layer was acidified with 2N hydrochloric acid and extracted with ethyl acetate. The thus obtained extract was washed successively with water and a saturated saline solution, and dried over anhydrous sodium sulfate. A residue obtained through filtration and concentration under reduced pressure was purified by silica gel column chromatography [elution solvent: methanol/ethyl acetate=1/10-1/1 (V/V)] to obtain 166 mg (64%) of the title compound in the form of a white solid. The thus obtained white solid was crystalline.

$^1$H-NMR (400 MHz, DMSO-D$_6$) δ: 12.65 (1H, br s), 8.75 (1H, s), 7.43-7.40 (2H, m), 7.12 (1H, t, J=74.7 Hz), 7.10-7.06 (2H, m), 6.44 (1H, s), 2.03-1.94 (1H, m), 1.83-1.74 (1H, m), 1.47 (3H, s), 0.83 (3H, t, J=7.4 Hz).

MS m/z: 303 (M+H)$^+$.

$[α]_D^{25}$ −7.89 (c 1.0, Methanol).

A powder X-ray diffraction pattern of the crystals obtained through irradiation with copper Kα radiation (λ=1.54 angstroms, scanning speed=20°/min) is illustrated in FIG. 1. Peaks each having relative intensity, calculated by assuming that the maximum peak intensity is 100, of 20 or more in FIG. 1 are shown in Table 1.

TABLE 1

| Peak No. | 2θ | d Value | Relative Intensity |
|---|---|---|---|
| 1 | 11.78 | 7.51 | 63 |
| 2 | 12.06 | 7.33 | 26 |
| 3 | 13.26 | 6.67 | 24 |
| 4 | 14.38 | 6.15 | 59 |
| 5 | 16.64 | 5.32 | 24 |
| 6 | 16.92 | 5.24 | 59 |
| 7 | 17.80 | 4.98 | 60 |
| 8 | 18.50 | 4.79 | 25 |
| 9 | 22.46 | 3.96 | 100 |
| 10 | 24.76 | 3.59 | 20 |

Example 9

2-({[4-(Difluoromethoxy)phenyl]carbamoyl}amino)-2-ethylbutanoic acid

[Formula 31]

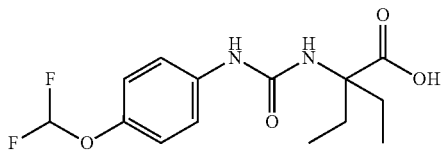

To a 1N sodium hydroxide (0.92 mL, 0.92 mmol) solution of 2-amino-2-ethylbutanoic acid (CAS Registry Number: 2566-29-2) (100 mg, 0.76 mmol), a dichloromethane (3 mL) solution of 1-(difluoromethoxy)-4-isocyanatobenzene (CAS Registry Number: 58417-15-5) (282 mg, 1.52 mmol) was added, followed by stirring at room temperature overnight. Ethyl acetate and water were added to the resultant, an organic layer and an aqueous layer were separated, and then, the aqueous layer was acidified with 2N hydrochloric acid and extracted with ethyl acetate. The thus obtained extract was washed with a saturated saline solution, dried over anhydrous sodium sulfate, filtered and concentrated under reduced pressure. The thus obtained residue was dissolved in a 1N sodium hydroxide solution, and insoluble matter was filtered. A solid obtained by acidifying the resultant with 2N hydrochloric acid was filtered, washed successively with water and n-hexane, and dried under reduced pressure to obtain 143 mg (59%) of the title compound in the form of a white solid.

$^1$H-NMR (400 MHz, DMSO-D$_6$) δ: 12.97 (1H, br s), 8.94 (1H, s), 7.37-7.32 (2H, m), 7.03 (1H, t, J=74.7 Hz), 7.02-6.97 (2H, m), 6.84 (1H, s), 2.23-2.15 (2H, m), 1.72-1.63 (2H, m), 0.70 (6H, t, J=7.4 Hz).

MS m/z: 317 (M+H)$^+$.

Example 10

Dicyclopropyl({[4-(difluoromethoxy)phenyl]carbamoyl}amino)acetic acid

[Formula 32]

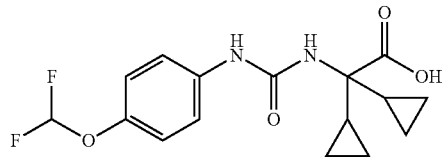

To a 1N sodium hydroxide (0.77 mL, 0.77 mmol) solution of amino(dicyclopropyl)acetic acid (CAS Registry Number: 6321-21-7) (100 mg, 0.64 mmol), a dichloromethane (3 mL) solution of 1-(difluoromethoxy)-4-isocyanatobenzene (CAS Registry Number: 58417-15-5) (239 mg, 1.29 mmol) was added, followed by stirring at room temperature for 5 hours. Ethyl acetate, water and a 1N sodium hydroxide solution (0.77 mL) were added to the resultant, and an organic layer and an aqueous layer were separated. A solid obtained by acidifying the aqueous layer with 2N hydrochloric acid was filtered, washed successively with water and n-hexane, and dried under reduced pressure to obtain 150 mg (68%) of the title compound in the form of a white solid.

$^1$H-NMR (400 MHz, DMSO-D$_6$) δ: 8.55 (1H, s), 7.34-7.30 (2H, m), 7.04 (1H, t, J=74.7 Hz), 7.02-6.98 (2H, m), 6.05 (1H, s), 1.25-1.18 (2H, m), 0.44-0.30 (8H, m).

MS m/z: 341 (M+H)$^+$.

Example 11

2-Cyclopropyl-2-({[4-(difluoromethoxy)phenyl]carbamoyl}amino)butanoic acid

[Formula 33]

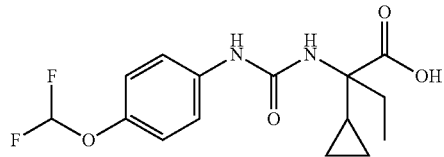

To a 1N sodium hydroxide (0.74 mL, 0.74 mmol) solution of 2-amino-2-cyclopropylbutanoic acid hydrochloride (CAS Registry Number: 1864016-20-5) (60 mg, 0.33 mmol), a dichloromethane (3 mL) solution of 1-(difluoromethoxy)-4-isocyanatobenzene (CAS Registry Number: 58417-15-5) (185 mg, 1.00 mmol) was added, followed by stirring at room temperature overnight. Ethyl acetate, water and a 1N sodium hydroxide solution (0.4 mL) were added to the resultant, and an organic layer and an aqueous layer were separated. A solid obtained by acidifying the aqueous layer with 2N hydrochloric acid was filtered, washed successively with water and n-hexane, and dried under reduced pressure to obtain 78 mg (71%) of the title compound in the form of a white solid.

$^1$H-NMR (400 MHz, DMSO-D$_6$) δ: 12.70 (1H, br s), 8.79 (1H, s), 7.35-7.31 (2H, m), 7.04 (1H, t, J=74.7 Hz), 7.02-6.98 (2H, m), 6.12 (1H, s), 2.24-2.15 (1H, m), 1.98-1.89 (1H, m), 1.30-1.23 (1H, m), 0.77 (3H, t, J=7.4 Hz), 0.42-0.27 (4H, m).

MS m/z: 329 (M+H)$^+$.

Example 12

2-Ethyl-({[4-(fluoromethoxy)phenyl]carbamoyl}amino)butanoic acid

[Formula 34]

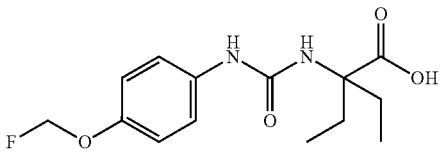

To a toluene (35.4 mL) solution of 4-(fluoromethoxy)aniline (CAS Registry Number: 1359823-67-8) (500 mg, 3.54 mmol) and triethylamine (1.19 mL, 8.50 mmol), triphosgene (547 mg, 1.84 mmol) was added, followed by stirring at room temperature for 5 hours. Insoluble matter was filtered with toluene, and then, the thus obtained filtrate was concentrated under reduced pressure to obtain 1-(fluoromethoxy)-4-isocyanatobenzene as a crude product in the form of light brown oil.

A dichloromethane (5 mL) solution of the thus obtained crude product was added to a 1N sodium hydroxide (1.83 mL, 1.83 mmol) solution of 2-amino-2-ethylbutanoic acid (CAS Registry Number: 2566-29-2) (200 mg, 1.52 mmol), followed by stirring at room temperature overnight. Ethyl acetate, water and a 1N sodium hydroxide solution (1.83 mL) were added to the resultant, and an organic layer and an aqueous layer were separated. A solid obtained by acidifying the aqueous layer with 2N hydrochloric acid was filtered, washed successively with water and n-hexane, and dried under reduced pressure to obtain 12 mg (3%) of the title compound in the form of a white solid.

$^1$H-NMR (400 MHz, DMSO-D$_6$) δ: 13.02 (1H, br s), 8.86 (1H, s), 7.34-7.30 (2H, m), 6.98-6.94 (2H, m), 6.29 (1H, s), 5.75 (2H, d, J=55.1 Hz), 2.26-2.17 (2H, m), 1.77-1.65 (2H, m), 0.72 (6H, t, J=7.2 Hz).

MS m/z: 299 (M+H)$^+$.

Example 13

N-{[4-(2,2,2-Trifluoroethyl)phenyl]carbamoyl}-D-isovaline

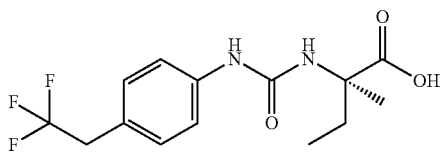

[Formula 35]

To a toluene (11.4 mL) solution of 4-(2,2,2-trifluoroethyl)aniline (CAS Registry Number: 131395-17-0) (400 mg, 2.28 mmol) and triethylamine (764 µL, 5.48 mmol), triphosgene (352 mg, 1.19 mmol) was added, followed by stirring at room temperature for 20 minutes, and then at 70° C. for 1.5 hours. The resultant was cooled to room temperature, and insoluble matter was filtered with toluene. The thus obtained filtrate was concentrated under reduced pressure to obtain 1-isocyanato-4-(2,2,2-trifluoroethyl)benzene as a crude product in the form of a light brown oil.

A dichloromethane (3 mL) solution of the thus obtained crude product was added to a 1N sodium hydroxide (1.02 mL, 1.02 mmol) solution of D-isovaline (CAS Registry Number: 3059-97-0) (100 mg, 0.85 mmol), followed by stirring at room temperature overnight. Ethyl acetate, water and a 1N sodium hydroxide solution (1.02 mL) were added to the resultant, and an organic layer and an aqueous layer were separated. A solid obtained by acidifying the aqueous layer with 2N hydrochloric acid was filtered, washed successively with water and n-hexane, and dried under reduced pressure to obtain 70 mg (26%) of the title compound in the form of a white solid.

$^1$H-NMR (400 MHz, DMSO-D$_6$) δ: 8.66 (1H, s), 7.32-7.30 (2H, m), 7.15 (2H, d, J=8.6 Hz), 6.38 (1H, s), 3.48 (2H, q, J=11.6 Hz), 1.95-1.86 (1H, m), 1.76-1.67 (1H, m), 1.40 (3H, s), 0.76 (3H, t, J=7.6 Hz).

MS m/z: 319 (M+H)$^+$.

Example 14

2-Ethyl-2-[({4-[(trifluoromethyl)sulfanyl]phenyl}carbamoyl)amino]butanoic acid

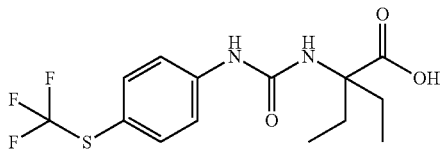

[Formula 36]

To a toluene (10.4 mL) solution of 4-[(trifluoromethyl)sulfanyl]aniline (CAS Registry Number: 372-16-7) (400 mg, 2.07 mmol) and triethylamine (693 µL, 4.97 mmol), triphosgene (319 mg, 1.08 mmol) was added, followed by stirring at room temperature for 15 minutes, and then at 70° C. for 2 hours. The resultant was cooled to room temperature, and insoluble matter was filtered with toluene. The thus obtained filtrate was concentrated under reduced pressure to obtain 1-isocyanato-4-[(trifluoromethyl)sulfanyl]benzene as a crude product in the form of a light brown oil.

A dichloromethane (3 mL) solution of the thus obtained crude product was added to a 1N sodium hydroxide (0.92 mL, 0.92 mmol) solution of 2-amino-2-ethylbutanoic acid (CAS Registry Number: 2566-29-2) (100 mg, 0.76 mmol), followed by stirring at room temperature for 2.5 hours. Ethyl acetate, water and a 1N sodium hydroxide solution (0.92 mL) were added to the resultant, and an organic layer and an aqueous layer were separated. A solid obtained by acidifying the aqueous layer with 2N hydrochloric acid was filtered, washed successively with water and n-hexane, and dried under reduced pressure to obtain 168 mg (63%) of the title compound in the form of a white solid.

$^1$H-NMR (400 MHz, DMSO-D$_6$) δ: 13.08 (1H, br s), 9.31 (1H, s), 7.53-7.46 (4H, m), 6.48 (1H, s), 2.25-2.16 (2H, m), 1.73-1.64 (2H, m), 0.70 (6H, t, J=7.4 Hz).

MS m/z: 351 (M+H)$^+$.

Example 15

(−)-N-{[4-(Difluoromethoxy)-3-fluorophenyl]carbamoyl}-D-isovaline

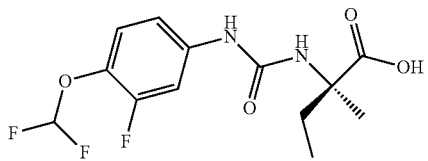

[Formula 37]

To a toluene (11.3 mL) solution of 4-(difluoromethoxy)-3-fluoroaniline (CAS Registry Number: 83190-01-6) (400 mg, 2.26 mmol) and triethylamine (755 µL, 5.42 mmol), triphosgene (348 mg, 1.17 mmol) was added, followed by stirring at room temperature for 20 minutes, and then at 70° C. for 80 minutes. The resultant was cooled to room temperature, and insoluble matter was filtered with toluene. The thus obtained filtrate was concentrated under reduced pressure to obtain 1-(difluoromethoxy)-2-fluoro-4-isocyanatobenzene as a crude product in the form of light brown oil.

A dichloromethane (3 mL) solution of the thus obtained crude product was added to a 1N sodium hydroxide (1.02 mL, 1.02 mmol) solution of D-isovaline (CAS Registry Number: 3059-97-0) (100 mg, 0.85 mmol), followed by stirring at room temperature for 3.5 hours. Ethyl acetate, water and a 1N sodium hydroxide solution (1.02 mL) were added to the resultant, an organic layer and an aqueous layer were separated, and then, the aqueous layer was acidified with 2N hydrochloric acid and extracted with ethyl acetate. The thus obtained extract was washed with a saturated saline solution, and dried over anhydrous sodium sulfate. A residue obtained through filtration and concentration under reduced pressure was purified by silica gel column chromatography [elution solvent: methanol/ethyl acetate=1/10-1/2 (V/V)] to obtain 49 mg (18%) of the title compound in the form of a white solid. The thus obtained white solid was crystalline.

$^1$H-NMR (400 MHz, DMSO-D$_6$) δ: 12.65 (1H, br s), 8.91 (1H, s), 7.54 (1H, dd, J=13.5, 2.5 Hz), 7.18 (1H, t, J=9.0 Hz), 7.06 (1H, t, J=73.5 Hz), 6.96 (1H, dq, J=8.9, 1.2 Hz), 6.47 (1H, s), 1.96-1.87 (1H, m), 1.76-1.67 (1H, m), 1.40 (3H, s), 0.75 (3H, t, J=7.4 Hz).

MS m/z: 321 (M+H)⁺.

[α]$_D^{25}$ −8.82° (c 1.0, Methanol).

Figure 2:
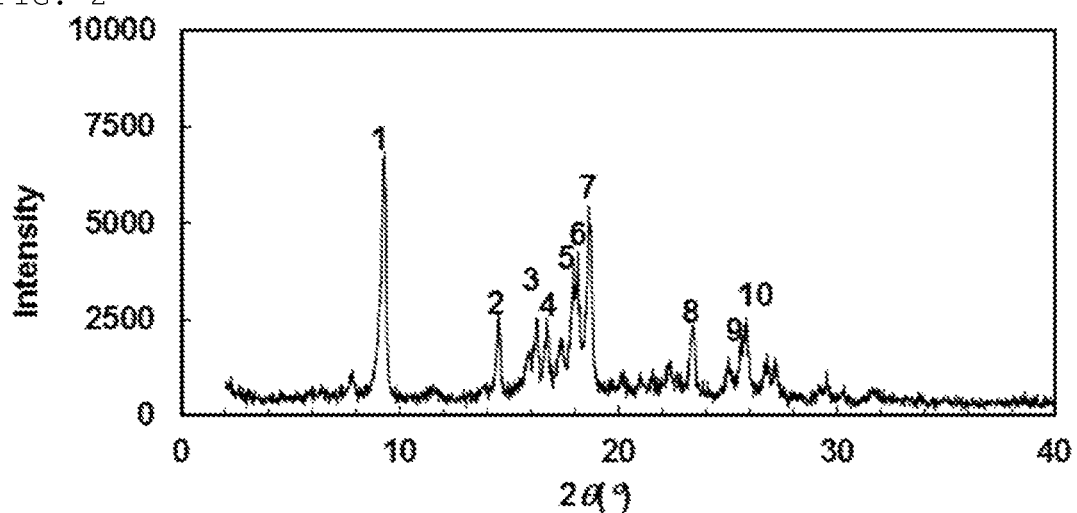
FIG. 2 is a powder X-ray diffraction diagram of crystals obtained in Example 15. The ordinate indicates diffraction intensity in count/sec. (cps), and the abscissa indicates a value of diffraction angle 2θ.

A powder X-ray diffraction pattern of the crystals obtained through irradiation with copper Kα radiation (λ=1.54 angstroms, scanning speed=20°/min) is illustrated in FIG. 2. Peaks each having relative intensity, calculated by assuming that the maximum peak intensity is 100, of 30 or more in FIG. 2 are shown in Table 2.

TABLE 2

| Peak No. | 2θ | d Value | Relative Intensity |
| --- | --- | --- | --- |
| 1 | 9.28 | 9.52 | 100 |
| 2 | 14.52 | 6.10 | 37 |
| 3 | 16.26 | 5.45 | 39 |
| 4 | 16.74 | 5.29 | 37 |
| 5 | 17.94 | 4.94 | 55 |
| 6 | 18.14 | 4.89 | 59 |
| 7 | 18.68 | 4.75 | 80 |
| 8 | 23.42 | 3.80 | 36 |
| 9 | 25.60 | 3.48 | 30 |
| 10 | 25.86 | 3.44 | 38 |

Example 16

2-({[4-(Difluoromethoxy)-2-fluorophenyl]carbamoyl}amino)-2-ethylbutanoic acid

[Formula 38]

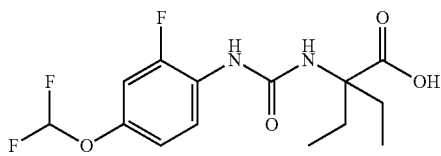

To a toluene (11.3 mL) solution of 4-(difluoromethoxy)-2-fluoroaniline (CAS Registry Number: 1003865-65-3) (400 mg, 2.26 mmol) and triethylamine (755 μL, 5.42 mmol), triphosgene (348 mg, 1.17 mmol) was added, followed by stirring at room temperature overnight. Insoluble matter was filtered with toluene, and the thus obtained filtrate was concentrated under reduced pressure to obtain 4-(difluoromethoxy)-2-fluoro-1-isocyanatobenzene as a crude product in the form of pale yellow oil.

A dichloromethane (3 mL) solution of the thus obtained crude product was added to a 1N sodium hydroxide (0.92 mL, 0.92 mmol) solution of 2-amino-2-ethylbutanoic acid (CAS Registry Number: 2566-29-2) (100 mg, 0.76 mmol), followed by stirring at room temperature for 5 hours. Ethyl acetate, water and a 1N sodium hydroxide solution (0.92 mL) were added to the resultant, and an organic layer and an aqueous layer were separated. A solid obtained by acidifying the aqueous layer with 2N hydrochloric acid was filtered, washed successively with water and n-hexane, and dried under reduced pressure to obtain 18 mg (7%) of the title compound in the form of a white solid.

¹H-NMR (400 MHz, DMSO-D₆) δ: 12.87 (1H, br s), 8.76 (1H, d, J=1.6 Hz), 8.07 (1H, t, J=9.2 Hz), 7.14 (1H, t, J=74.1 Hz), 7.14-7.10 (1H, m), 6.92-6.90 (1H, m), 6.87 (1H, s), 2.20-2.11 (2H, m), 1.76-1.67 (2H, m), 0.73 (6H, t, J=7.4 Hz).

MS m/z: 335 (M+H)⁺.

Example 17

N-{[4-(Difluoromethoxy)-2-fluorophenyl]carbamoyl}-D-isovaline

[Formula 39]

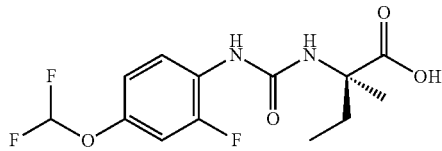

To a toluene (11.3 mL) solution of 4-(difluoromethoxy)-2-fluoroaniline (CAS Registry Number: 1003865-65-3) (400 mg, 2.26 mmol) and triethylamine (0.755 mL, 5.42 mmol), triphosgene (348 mg, 1.17 mmol) was added, followed by stirring at 70° C. for 2 hours. The resultant was cooled to room temperature, and insoluble matter was filtered with toluene. The thus obtained filtrate was concentrated under reduced pressure to obtain 4-(difluoromethoxy)-2-fluoro-1-isocyanatobenzene as a crude product in the form of pale yellow oil.

A dichloromethane (3 mL) solution of the thus obtained crude product was added to a 1N sodium hydroxide (1.02 mL, 1.02 mmol) solution of D-isovaline (CAS Registry Number: 3059-97-0) (100 mg, 0.85 mmol), followed by stirring at room temperature for 4 hours. Ethyl acetate, water and a 1N sodium hydroxide solution (1.02 mL) were added to the resultant, an organic layer and an aqueous layer were separated, and then, the aqueous layer was acidified with 2N hydrochloric acid and extracted with ethyl acetate. The thus obtained extract was washed with a saturated saline solution, and dried over anhydrous sodium sulfate. A residue obtained through filtration and concentration under reduced pressure was purified by silica gel column chromatography [elution solvent: methanol/ethyl acetate=1/10-1/1 (V/V)] to obtain 89 mg (33%) of the title compound in the form of a white solid.

¹H-NMR (400 MHz, DMSO-D₆) δ: 12.50 (1H, br s), 8.50 (1H, d, J=2.3 Hz), 8.08 (1H, t, J=9.2 Hz), 7.14 (1H, t, J=74.1 Hz), 7.13 (1H, dd, J=12.1, 2.7 Hz), 6.93-6.90 (1H, m), 6.88 (1H, s), 1.89-1.82 (1H, m), 1.78-1.69 (1H, m), 1.41 (3H, s), 0.80 (3H, t, J=7.4 Hz).

MS m/z: 321 (M+H)⁺.

Example 18

N-{[3-Chloro-4-(difluoromethoxy)phenyl]carbamoyl}-D-isovaline

[Formula 40]

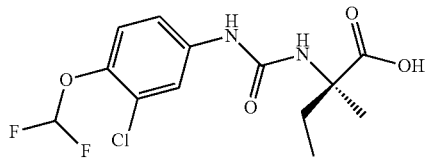

18a

Benzyl D-isovalinate

To a dichloromethane (10 mL) solution of benzyl N-(tert-butoxycarbonyl)-D-isovalinate (CAS Registry Number: 141345-74-6, Journal of the American Chemical Society, 1992, 114, 4095-4106) (1.98 g, 6.43 mmol), trifluoroacetic acid (4.92 mL, 64.3 mmol) was added, followed by stirring at room temperature for 50 minutes. The thus obtained reaction solution was concentrated under reduced pressure, saturated sodium bicarbonate was added thereto, and the resultant was extracted with dichloromethane. The thus obtained extract was washed with a saturated saline solution, and dried over anhydrous magnesium sulfate. The resultant was filtered and then concentrated under reduced pressure to obtain 1.25 g (94%) of the title compound in the form of colorless oil.

$^1$H-NMR (400 MHz, CDCl$_3$) δ: 7.36-7.27 (5H, m), 5.11 (2H, s), 1.76-1.73 (1H, m), 1.60-1.54 (1H, m), 1.30 (3H, s), 0.80 (3H, t, J=7.4 Hz).

18b

Benzyl N-{[3-chloro-4-(difluoromethoxy)phenyl]carbamoyl}-D-isovalinate

To a toluene (5.17 mL) solution of 3-chloro-4-(difluoromethoxy)aniline (200 mg, 1.03 mmol) and triethylamine (346 μL, 2.48 mmol), triphosgene (159 mg, 0.54 mmol) was added, followed by stirring at room temperature for 2 hours. Insoluble matter was filtered with toluene, and the thus obtained filtrate was concentrated under reduced pressure to obtain 2-chloro-1-(difluoromethoxy)-4-isocyanatobenzene as a crude product in the form of brown oil.

The thus obtained crude product was added to a tetrahydrofuran (9.65 mL) solution of the benzyl D-isovalinate (200 mg, 0.96 mmol) obtained in Example 18a, followed by stirring at room temperature for 25 minutes. A residue obtained through concentration under reduced pressure was purified by silica gel column chromatography [elution solvent: n-hexane/ethyl acetate=9/1-1/1 (V/V)] to obtain 390 mg (95%) of the title compound in the form of a light brown amorphous solid.

$^1$H-NMR (400 MHz, CDCl$_3$) δ: 7.53 (1H, d, J=2.3 Hz), 7.32-7.31 (5H, m), 7.09-7.07 (2H, m), 6.42 (1H, t, J=73.7 Hz), 6.36 (1H, br s), 5.42 (1H, br s), 5.19 (1H, d, J=12.1 Hz), 5.15 (1H, d, J=12.1 Hz), 2.26-2.17 (1H, m), 1.89-1.80 (1H, m), 1.61 (3H, s), 0.76 (3H, t, J=7.4 Hz).

18c

N-{[3-Chloro-4-(difluoromethoxy)phenyl]carbamoyl}-D-isovaline

To a methanol/tetrahydrofuran (1:1, 20 mL) solution of the benzyl N-{[3-chloro-4-(difluoromethoxy)phenyl]carbamoyl}-D-isovalinate (390 mg, 0.91 mmol) obtained in Example 18b, a 1N sodium hydroxide solution (9.14 mL, 9.14 mmol) was added, followed by stirring at 50° C. for 2.5 hours, and then at room temperature overnight. The resultant was concentrated under reduced pressure, ethyl acetate and water were added thereto, an organic layer and an aqueous layer were separated, and then, the aqueous layer was acidified with 2N hydrochloric acid and extracted with ethyl acetate. The thus obtained extract was washed successively with water and a saturated saline solution, and dried over anhydrous sodium sulfate. The residue obtained through filtration and concentration under reduced pressure was purified by silica gel column chromatography [elution solvent: methanol/ethyl acetate=1/10-1/1 (V/V)] to obtain 80 mg (26%) of the title compound in the form of a light brown solid.

$^1$H-NMR (400 MHz, DMSO-D$_6$) δ: 12.67 (1H, br s), 8.97 (1H, s), 7.74 (1H, d, J=2.3 Hz), 7.29-6.90 (3H, m), 6.54 (1H, s), 1.97-1.88 (1H, m), 1.76-1.67 (1H, m), 1.40 (3H, s), 0.75 (3H, t, J=7.4 Hz).

MS m/z: 337, 339 (M+H)$^+$.

Example 19

N-{[3-Cyano-4-(trifluoromethoxy)phenyl]carbamoyl}-D-isovaline

[Formula 41]

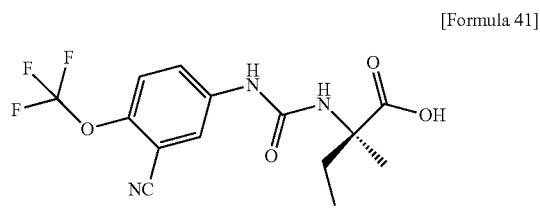 [SMILES: CC[C@@](C)(NC(=O)Nc1ccc(OC(F)(F)F)c(C#N)c1)C(=O)O]

To a toluene (2.97 mL) solution of triphosgene (295 mg, 0.99 mmol), a 1,4-dioxane (2.97 mL) solution of 5-amino-2-(trifluoromethoxy)benzonitrile (CAS Registry Number: 1261523-71-0) (300 mg, 1.48 mmol) was added, followed by stirring at 100° C. for 2.5 hours. The resultant was cooled to room temperature, insoluble matter was filtered with toluene, and then, the resultant was concentrated under reduced pressure to obtain 5-isocyanato-2-(trifluoromethoxy)benzonitrile as a crude product in the form of a light brown oil.

A dichloromethane (3 mL) solution of the thus obtained crude product was added to a 1N sodium hydroxide (1.02 mL, 1.02 mmol) solution of D-isovaline (CAS Registry Number: 3059-97-0) (100 mg, 0.85 mmol) and sodium hydrogen carbonate (143 mg, 1.71 mmol), followed by stirring at room temperature overnight. Ethyl acetate, water and a 1N sodium hydroxide solution (1.02 mL) were added to the resultant, an organic layer and an aqueous layer were separated, and then, the aqueous layer was acidified with 2N hydrochloric acid and extracted with ethyl acetate. The thus obtained extract was washed with a saturated saline solution and dried over anhydrous sodium sulfate. A residue obtained through filtration and concentration under reduced pressure was purified by silica gel column chromatography [elution solvent: methanol/ethyl acetate=1/20-3/2 (V/V)] to obtain 179 mg (61%) of the title compound in the form of a white solid.

$^1$H-NMR (400 MHz, DMSO-D$_6$) δ: 12.74 (1H, br s), 9.48 (1H, br s), 8.02 (1H, d, J=2.7 Hz), 7.65 (1H, dd, J=9.0, 2.7 Hz), 7.50 (1H, dd, J=9.2, 1.4 Hz), 6.84 (1H, br s), 2.00-1.91 (1H, m), 1.77-1.68 (1H, m), 1.40 (3H, s), 0.73 (3H, t, J=7.4 Hz).

Example 20

2-Ethyl-2-({[4-(trifluoromethyl)phenyl]carbamoyl}amino)butanoic acid

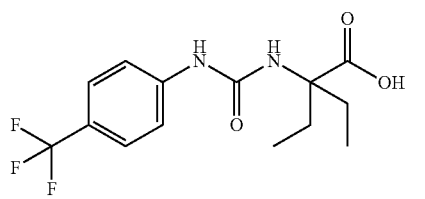
[Formula 42]

To a 1N sodium hydroxide (1.83 mL, 1.83 mmol) solution of 2-amino-2-ethylbutanoic acid (CAS Registry Number: 2566-29-2) (200 mg, 1.52 mmol), a dichloromethane (5 mL) solution of 1-isocyanato-4-(trifluoromethyl)benzene (CAS Registry Number: 1548-13-6) (856 mg, 4.57 mmol) solution was added, followed by stirring at room temperature overnight. Ethyl acetate, water and a 1N sodium hydroxide solution (1.83 mL) were added to the resultant, an organic layer and an aqueous layer were separated, and then, the aqueous layer was acidified with 2N hydrochloric acid. A solid obtained by acidifying the aqueous layer with 2N hydrochloric acid was filtered, washed successively with water and n-hexane, and dried under reduced pressure to obtain 364 mg (75%) of the title compound in the form of a white solid.

$^1$H-NMR (400 MHz, DMSO-D$_6$) δ: 13.13 (1H, br s), 9.36 (1H, s), 7.56 (4H, s), 6.51 (1H, s), 2.30-2.21 (2H, m), 1.77-1.68 (2H, m), 0.74 (6H, t, J=7.6 Hz).

MS m/z: 319 (M+H)$^+$.

Example 21

Dicyclopropyl[(phenylcarbamoyl)amino]acetic acid

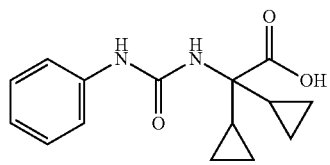
[Formula 43]

To a 1N sodium hydroxide (773 μL, 0.77 mmol) solution of amino(dicyclopropyl)acetic acid (CAS Registry Number: 6321-21-7) (100 mg, 0.64 mmol), a dichloromethane (3 mL) solution of isocyanatobenzene (CAS Registry Number: 103-71-9) (154 mg, 1.29 mmol) was added, followed by stirring at room temperature for 4.5 hours. Ethyl acetate, water and a 1N sodium hydroxide solution (773 μL) were added to the resultant, and an organic layer and an aqueous layer were separated. A solid obtained by acidifying the aqueous layer with 2N hydrochloric acid was filtered, washed successively with water and n-hexane, and dried under reduced pressure to obtain 72 mg (41%) of the title compound in the form of a white solid.

$^1$H-NMR (400 MHz, DMSO-D$_6$) δ: 12.18 (1H, br s), 8.46 (1H, s), 7.29-7.27 (2H, m), 7.19-7.14 (2H, m), 6.86-6.82 (1H, m), 6.04 (1H, s), 1.25-1.18 (2H, m), 0.43-0.30 (8H, m).

MS m/z: 275 (M+H)$^+$.

Example 22

2-Cyclopropyl-2-[(phenylcarbamoyl)amino]butanoic acid

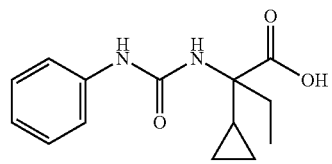
[Formula 44]

To a 1N sodium hydroxide (649 μL, 0.65 mmol) solution of 2-amino-2-cyclopropylbutanoic acid hydrochloride (CAS Registry Number: 1864016-20-5) (53 mg, 0.30 mmol), a dichloromethane (3 mL) solution of isocyanatobenzene (CAS Registry Number: 103-71-9) (105 mg, 0.89 mmol) was added, followed by stirring at room temperature for 4 hours. Ethyl acetate, water and a 1N sodium hydroxide solution (0.35 mL) were added to the resultant, and an organic layer and an aqueous layer were separated. A solid obtained by acidifying the aqueous layer with 2N hydrochloric acid was filtered, washed successively with water and n-hexane, and dried under reduced pressure to obtain 42 mg (54%) of the title compound in the form of a white solid.

$^1$H-NMR (400 MHz, DMSO-D$_6$) δ: 12.66 (1H, br s), 8.70 (1H, s), 7.31-7.28 (2H, m), 7.18-7.14 (2H, m), 6.86-6.81 (1H, m), 6.11 (1H, s), 2.23-2.14 (1H, m), 1.99-1.90 (1H, m), 1.30-1.23 (1H, m), 0.77 (3H, t, J=7.4 Hz), 0.42-0.27 (4H, m).

MS m/z: 263 (M+H)$^+$.

Example 23

2-Cyclopropyl-2-{[(4-fluorophenyl)carbamoyl]amino}butanoic acid

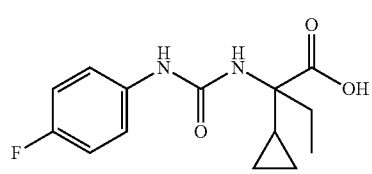
[Formula 45]

To a 1N sodium hydroxide (686 μL, 0.69 mmol) solution of 2-amino-2-cyclopropylbutanoic acid hydrochloride (CAS Registry Number: 1864016-20-5) (56 mg, 0.31 mmol), a dichloromethane (2 mL) solution of 1-fluoro-4-isocyanatobenzene (CAS Registry Number: 1195-45-5) (128 mg, 0.94 mmol) was added, followed by stirring at room temperature for 4 hours. Ethyl acetate, water and a 1N sodium hydroxide solution (0.37 mL) were added to the resultant, and an organic layer and an aqueous layer were separated. A solid obtained by acidifying the aqueous layer with 2N hydrochloric acid was filtered, washed successively with water and n-hexane, and dried under reduced pressure to obtain 57 mg (65%) of the title compound in the form of a white solid.

$^1$H-NMR (400 MHz, DMSO-D$_6$) δ: 12.68 (1H, br s), 8.74 (1H, s), 7.33-7.28 (2H, m), 7.04-6.97 (2H, m), 6.09 (1H, s), 2.24-2.15 (1H, m), 1.98-1.89 (1H, m), 1.30-1.23 (1H, m), 0.77 (3H, t, J=7.4 Hz), 0.42-0.27 (4H, m).

MS m/z: 281 (M+H)$^+$.

Example 24

N-[(3-Fluorophenyl)carbamoyl]-D-isovaline

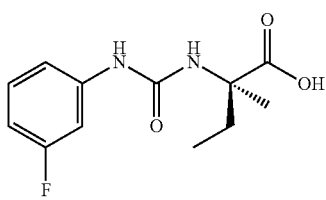

[Formula 46]

To a 1N sodium hydroxide (1.02 mL, 1.02 mmol) solution of D-isovaline (CAS Registry Number: 3059-97-0) (100 mg, 0.85 mmol), a dichloromethane (2 mL) solution of 1-fluoro-3-isocyanatobenzene (CAS Registry Number: 404-71-7) (234 mg, 1.71 mmol) was added, followed by stirring at room temperature for 3 hours. Ethyl acetate, water and a 1N sodium hydroxide solution (1.02 mL) were added to the resultant, and an organic layer and an aqueous layer were separated. A solid obtained by acidifying the aqueous layer with 2N hydrochloric acid was filtered, washed successively with water and n-hexane, and dried under reduced pressure to obtain 166 mg (77%) of the title compound in the form of a white solid.

$^1$H-NMR (400 MHz, DMSO-D$_6$) δ: 12.60 (1H, br s), 8.84 (1H, s), 7.40-7.36 (1H, m), 7.22-7.16 (1H, m), 6.94-6.91 (1H, m), 6.68-6.62 (1H, m), 6.44 (1H, s), 1.96-1.87 (1H, m), 1.76-1.67 (1H, m), 1.41 (3H, s), 0.76 (3H, t, J=7.4 Hz).

MS m/z: 255 (M+H)$^+$.

Example 25

(−)-N-[(4-Chlorophenyl)carbamoyl]-D-isovaline

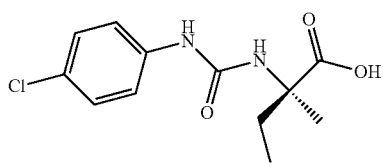

[Formula 47]

To a 1N sodium hydroxide (1.02 mL, 1.02 mmol) solution of D-isovaline (CAS Registry Number: 3059-97-0) (100 mg, 0.85 mmol), a dichloromethane (3 mL) solution of 1-chloro-4-isocyanatobenzene (CAS Registry Number: 104-12-1) (262 mg, 1.71 mmol) was added, followed by stirring at room temperature for 4.5 hours. Ethyl acetate and water were added to the resultant, and insoluble matter was filtered. After separating the thus obtained filtrate into an organic layer and an aqueous layer, a solid obtained by acidifying the aqueous layer with 2N hydrochloric acid was filtered, washed successively with water and n-hexane, and dried under reduced pressure to obtain 177 mg (77%) of the title compound in the form of a white solid. The obtained white solid was crystalline.

$^1$H-NMR (400 MHz, DMSO-D$_6$) δ: 12.56 (1H, br s), 8.74 (1H, s), 7.36-7.32 (2H, m), 7.23-7.19 (2H, m), 6.39 (1H, s), 1.96-1.87 (1H, m), 1.76-1.67 (1H, m), 1.40 (3H, s), 0.76 (3H, t, J=7.4 Hz).

MS m/z: 271, 273 (M+H)$^+$.

$[\alpha]_D^{25}$ −995° (c 1.0, Methanol).

Figure 3:
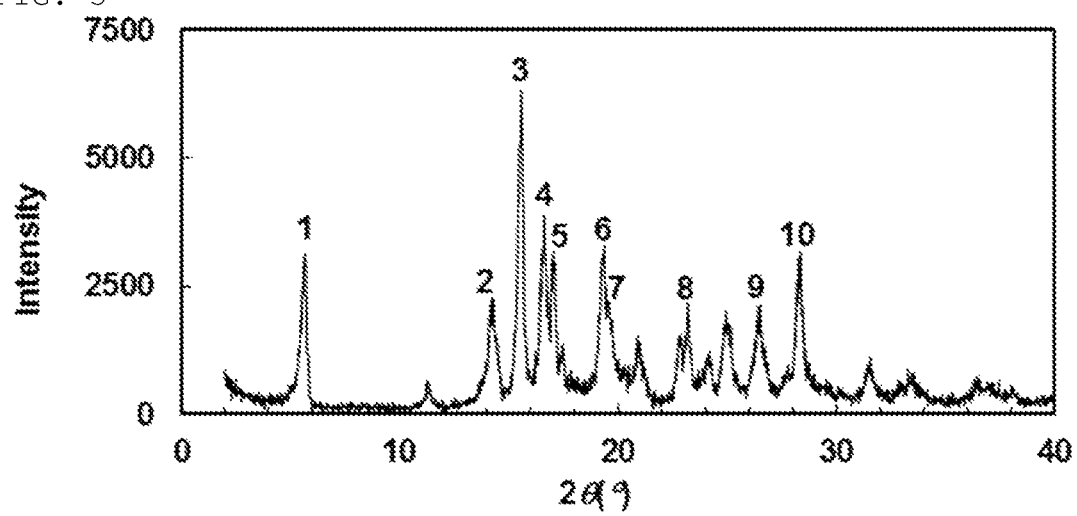
FIG. 3 is a powder X-ray diffraction diagram of crystals obtained in Example 25. The ordinate indicates diffraction intensity in count/sec. (cps), and the abscissa indicates a value of diffraction angle 2θ.

A powder X-ray diffraction pattern of the crystals obtained through irradiation with copper Kα radiation (λ=1.54 angstroms, scanning speed=20°/min) is illustrated in FIG. 3. Peaks each having relative intensity, calculated by assuming that the maximum peak intensity is 100, of 34 or more in FIG. 3 are shown in Table 3.

TABLE 3

| Peak No. | 2θ | d Value | Relative Intensity |
|---|---|---|---|
| 1 | 5.66 | 15.60 | 52 |
| 2 | 14.20 | 6.23 | 35 |
| 3 | 15.58 | 5.68 | 100 |
| 4 | 16.60 | 5.34 | 59 |
| 5 | 17.04 | 5.20 | 51 |
| 6 | 19.32 | 4.59 | 53 |
| 7 | 19.56 | 4.53 | 37 |
| 8 | 23.20 | 3.83 | 34 |
| 9 | 26.46 | 3.37 | 34 |
| 10 | 28.34 | 3.15 | 50 |

Example 26

N-[(3-Chlorophenyl)carbamoyl]-D-isovaline

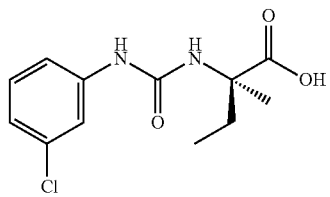

[Formula 48]

To a 1N sodium hydroxide (1.02 mL, 1.02 mmol) solution of D-isovaline (CAS Registry Number: 3059-97-0) (100 mg, 0.85 mmol), a dichloromethane (3 mL) solution of 1-chloro-3-isocyanatobenzene (CAS Registry Number: 2909-38-8) (262 mg, 1.71 mmol) was added, followed by stirring at room temperature for 2 hours. Ethyl acetate and water were added to the resultant, insoluble matter was filtered, and then, an organic layer and an aqueous layer were separated. A solid obtained by acidifying the aqueous layer with 2N hydrochloric acid was filtered, washed successively with water and n-hexane, and dried under reduced pressure to obtain 165 mg (71%) of the title compound in the form of a white solid.

$^1$H-NMR (400 MHz, DMSO-D$_6$) δ: 12.61 (1H, br s), 8.82 (1H, s), 7.62 (1H, t, J=2.0 Hz), 7.19 (1H, t, J=8.2 Hz), 7.08-7.05 (1H, m), 6.90-6.87 (1H, m), 6.44 (1H, s), 1.96-1.87 (1H, m), 1.77-1.68 (1H, m), 1.40 (3H, s), 0.76 (3H, t, J=7.4 Hz).

MS m/z: 271, 273 (M+H)$^+$.

Example 27

2-{[(5-Chlorothiophen-3-yl)carbamoyl]amino}-2-ethylbutanoic acid

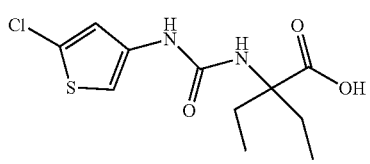

[Formula 49]

27a

Benzyl 2-{[(5-chlorothiophen-3-yl)carbamoyl]amino}-2-ethylbutanoic acid

Diphenylphosphoryl azide (508 mg, 1.85 mmol) was added to a tetrahydrofuran (8 mL) suspension of 5-chlorothiophene-3-carboxylic acid (CAS Registry Number: 36157-42-3) (250 mg, 1.54 mmol) and triethylamine (298 μL, 2.15 mmol), the resultant was stirred at room temperature for 7 minutes, and then, N,N-dimethylformamide (3 mL) was added thereto, followed by stirring at room temperature for 80 minutes. Benzyl 2-amino-2-ethylbutanoic acid (CAS Registry Number: 1413936-87-4, Beilstein Journal of Organic Chemistry, 2012, 8, 1265-1270) (408 mg, 1.85 mmol) was added thereto, followed by stirring at 70° C. for 4.5 hours. The resultant was cooled to room temperature, saturated sodium bicarbonate was added thereto, and the resultant was extracted with ethyl acetate. The thus obtained extract was washed successively with water and a saturated saline solution, and dried over anhydrous sodium sulfate. A residue obtained through filtration and concentration under reduced pressure was purified by silica gel column chromatography [elution solvent: n-hexane/ethyl acetate=9/1-3/1 (V/V)] to obtain 162 mg (28%) of the title compound in the form of a white solid.

$^1$H-NMR (400 MHz, CDCl$_3$) δ: 7.36-7.30 (5H, m), 6.83 (1H, d, J=2.0 Hz), 6.78 (1H, d, J=2.0 Hz), 6.40 (1H, s), 5.64 (1H, s), 5.16 (2H, s), 2.46-2.37 (2H, m), 1.85-1.76 (2H, m), 0.70 (6H, t, J=7.4 Hz).

27b

2-{[(5-Chlorothiophen-3-yl)carbamoyl]amino}-2-ethylbutanoic acid

To a methanol/tetrahydrofuran (1:1, 4 mL) solution of the benzyl 2-{[(5-chlorothiophen-3-yl)carbamoyl]amino}-2-ethylbutanoic acid (160 mg, 0.42 mmol) obtained in Example 27a, a 1N sodium hydroxide solution (4.20 mL, 4.20 mmol) was added, followed by stirring at room temperature overnight, and then at 50 to 60° C. for 10 hours. The resultant was concentrated under reduced pressure, diethyl ether and water were added thereto, and an organic layer and an aqueous layer were separated. A solid obtained by acidifying the aqueous layer with 2N hydrochloric acid was filtered, washed successively with water and n-hexane, and dried under reduced pressure to obtain 106 mg (87%) of the title compound in the form of a white solid. The obtained white solid was crystalline.

$^1$H-NMR (400 MHz, DMSO-D$_6$) δ: 13.02 (1H, s), 9.18 (1H, s), 6.93 (1H, d, J=2.0 Hz), 6.88 (1H, d, J=2.0 Hz), 6.28 (1H, s), 2.22-2.13 (2H, m), 1.62-1.71 (2H, m), 1.05 (6H, t, J=7.0 Hz).

MS m/z: 291, 293 (M+H)$^+$.

Figure 4:
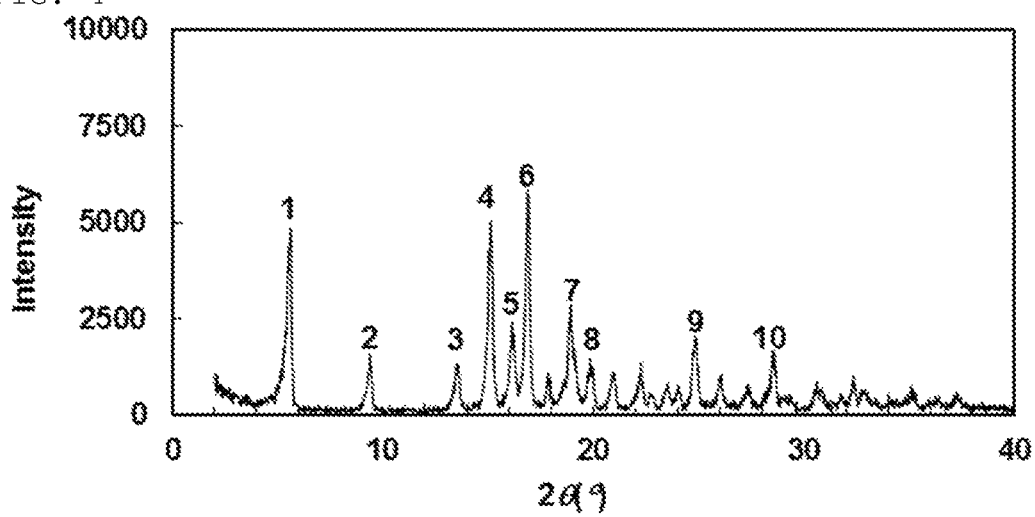
FIG. 4 is a powder X-ray diffraction diagram of crystals obtained in Example 27. The ordinate indicates diffraction intensity in count/sec. (cps), and the abscissa indicates a value of diffraction angle 2θ.

A powder X-ray diffraction pattern of the crystals obtained through irradiation with copper Kα radiation (λ=1.54 angstroms, scanning speed=20°/min) is illustrated in FIG. 4. Peaks each having relative intensity, calculated by assuming that the maximum peak intensity is 100, of 20 or more in FIG. 4 are shown in Table 4.

TABLE 4

| Peak No. | 2θ | d Value | Relative Intensity |
|---|---|---|---|
| 1 | 5.58 | 15.82 | 83 |
| 2 | 9.38 | 9.42 | 25 |
| 3 | 13.54 | 6.53 | 23 |
| 4 | 15.12 | 5.85 | 86 |
| 5 | 16.16 | 5.48 | 41 |
| 6 | 16.90 | 5.24 | 100 |
| 7 | 18.90 | 4.69 | 45 |
| 8 | 19.90 | 4.46 | 20 |
| 9 | 24.84 | 3.58 | 34 |
| 10 | 28.56 | 3.12 | 27 |

Example 28

2-{[(5-Chlorothiophen-2-yl)carbamoyl]amino}-2-ethylbutanoic acid

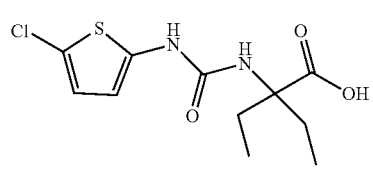

[Formula 50]

28a

Benzyl 2-{[(5-chlorothiophen-2-yl)carbamoyl]amino}-2-ethylbutanoic acid

Diphenylphosphoryl azide (406 mg, 1.48 mmol) was added to a toluene (4.9 mL) solution of 5-chlorothiophene-2-carboxylic acid (CAS Registry Number: 24065-33-6) (200 mg, 1.23 mmol) and triethylamine (239 μL, 1.72 mmol) at 0° C., the resultant was stirred at room temperature for 30 minutes, and then, benzyl 2-amino-2-ethylbutanoic acid (CAS Registry Number: 1413936-87-4) (Beilstein Journal of Organic Chemistry, 2012, 8, 1265-1270) (272 mg, 1.23 mmol) was added thereto, followed by stirring at 80° C. for 3.5 hours. The resultant was cooled to room temperature, saturated sodium bicarbonate was added thereto, and the resultant was extracted with ethyl acetate. The thus obtained extract was washed with a saturated saline solution, and dried over anhydrous sodium sulfate. A residue obtained through filtration and concentration under reduced pressure was purified by silica gel column chromatography [elution solvent: n-hexane/ethyl acetate=9/1-2/1 (V/V)] to obtain 342 mg (73%) of the title compound in the form of a white solid.

$^1$H-NMR (400 MHz, CDCl$_3$) δ: 7.35-7.27 (5H, m), 6.86 (1H, br s), 6.63 (1H, d, J=3.9 Hz), 6.33 (1H, d, J=4.3 Hz), 5.87 (1H, s), 5.14 (2H, s), 2.47-2.38 (2H, m), 1.85-1.75 (2H, m), 0.68 (6H, t, J=7.4 Hz).

28b

2-{[(5-Chlorothiophen-2-yl)carbamoyl]amino}-2-ethylbutanoic acid

To a methanol/tetrahydrofuran (2:1, 3 mL) solution of the benzyl 2-{[(5-chlorothiophen-2-yl)carbamoyl]amino}-2-ethylbutanoic acid (50 mg, 0.13 mmol) obtained in Example 28a, a 1N sodium hydroxide solution (1.05 mL, 1.05 mmol) was added, followed by stirring at room temperature overnight. The resultant was concentrated under reduced pressure, ethyl acetate and water were added thereto, and an organic layer and an aqueous layer were separated. A solid obtained by acidifying the aqueous layer with 2N hydrochloric acid was filtered, washed successively with water and n-hexane, and dried under reduced pressure to obtain 7 mg (18%) of the title compound in the form of a black solid.

$^1$H-NMR (400 MHz, DMSO-D$_6$) δ: 13.15 (1H, br s), 10.01 (1H, s), 6.71 (1H, d, J=3.9 Hz), 6.47 (1H, s), 6.11 (1H, d, J=4.3 Hz), 2.21-2.12 (2H, m), 1.71-1.63 (2H, m), 0.68 (6H, t, J=7.4 Hz).

MS m/z: 291, 293 (M+H)$^+$.

Example 29

N-[(3,4-Dichlorophenyl)carbamoyl]-D-isovaline

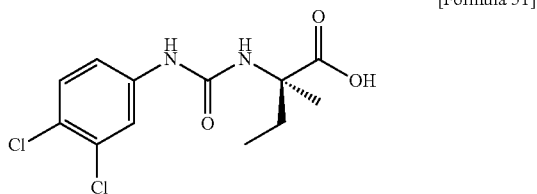

[Formula 51]

In the same manner as in Example 25, 105 mg (40%) of the title compound was obtained in the form of a white solid from D-isovaline (CAS Registry Number: 3059-97-0) (100 mg, 0.85 mmol), a 1N sodium hydroxide solution (1.02 mL, 1.02 mmol) and 1,2-dichloro-4-isocyanatobenzene (CAS Registry Number: 102-36-3) (321 mg, 1.71 mmol).

$^1$H-NMR (400 MHz, DMSO-D$_6$) δ: 12.75 (1H, br s), 9.03 (1H, s), 7.87 (1H, d, J=2.3 Hz), 7.48 (1H, d, J=8.6 Hz), 7.20 (1H, dd, J=8.8, 2.5 Hz), 6.58 (1H, s), 2.04-1.95 (1H, m), 1.83-1.74 (1H, m), 1.48 (3H, s), 0.83 (3H, t, J=7.4 Hz).

MS m/z: 305, 307 (M+H)$^+$.

Example 30

(−)-N-[(4-Bromophenyl)carbamoyl]-D-isovaline

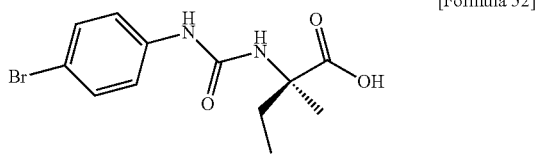

[Formula 52]

To a 1N sodium hydroxide (1.02 mL, 1.02 mmol) solution of D-isovaline (CAS Registry Number: 3059-97-0) (100 mg, 0.85 mmol), a dichloromethane (3 mL) solution of 1-bromo-4-isocyanatobenzene (CAS Registry Number: 2493-02-9) (338 mg, 1.71 mmol) was added, followed by stirring at room temperature overnight. Ethyl acetate and water were added to the resultant, and insoluble matter was filtered. After separating the thus obtained filtrate into an organic layer and an aqueous layer, a solid obtained by acidifying the aqueous layer with 2N hydrochloric acid was filtered, washed successively with water and n-hexane, and dried under reduced pressure to obtain 228 mg (85%) of the title compound in the form of a white solid. The obtained white solid was crystalline.

$^1$H-NMR (400 MHz, DMSO-D$_6$) δ: 12.69 (1H, s), 8.83 (1H, s), 7.42-7.35 (4H, m), 6.49 (1H, s), 2.03-1.94 (1H, m), 1.83-1.76 (1H, m), 1.47 (3H, s), 0.83 (3H, t, J=7.4 Hz).

MS m/z: 315, 317 (M+H)$^+$.

$[α]_D^{25}$ −8.70 (c 1.0, Methanol).

Figure 5:
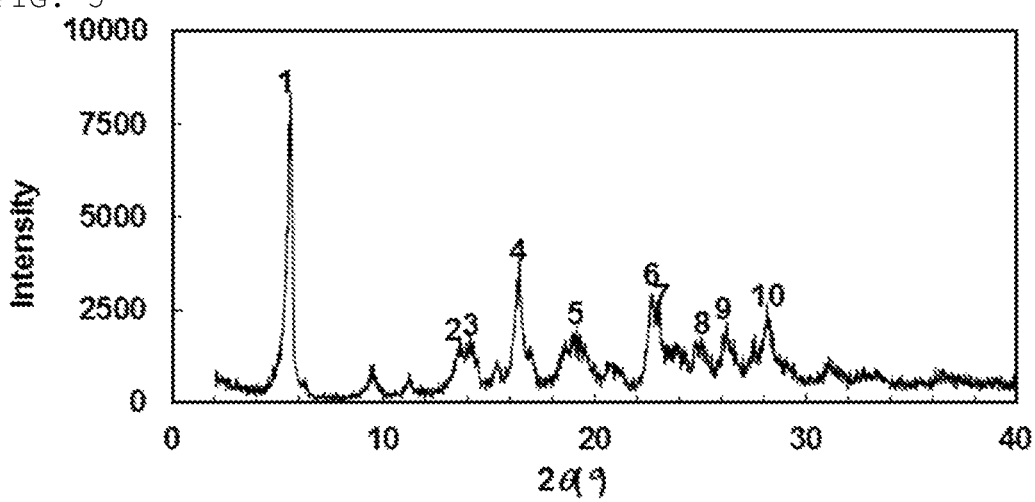
FIG. 5 is a powder X-ray diffraction diagram of crystals obtained in Example 30. The ordinate indicates diffraction intensity in count/sec. (cps), and the abscissa indicates a value of diffraction angle 2θ.

A powder X-ray diffraction pattern of the crystals obtained through irradiation with copper Kα radiation (λ=1.54 angstroms, scanning speed=20°/min) is illustrated in FIG. 5. Peaks each having relative intensity, calculated by assuming that the maximum peak intensity is 100, of 20 or more in FIG. 5 are shown in Table 5.

TABLE 5

| Peak No. | 2θ | d Value | Relative Intensity |
|---|---|---|---|
| 1 | 5.58 | 15.82 | 100 |
| 2 | 13.62 | 6.50 | 20 |
| 3 | 14.16 | 6.25 | 20 |
| 4 | 16.42 | 5.39 | 43 |
| 5 | 18.98 | 4.67 | 23 |
| 6 | 22.68 | 3.92 | 37 |
| 7 | 23.02 | 3.86 | 32 |
| 8 | 24.78 | 3.59 | 22 |
| 9 | 26.24 | 3.39 | 24 |
| 10 | 28.20 | 3.16 | 30 |

Example 31

(−)-N-[(4-Iodophenyl)carbamoyl]-D-isovaline

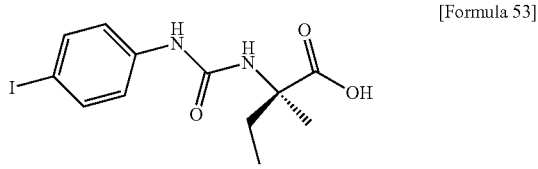 [SMILES: CC[C@@](C)(NC(=O)Nc1ccc(I)cc1)C(=O)O]

[Formula 53]

To a 1N sodium hydroxide (1.02 mL, 1.02 mmol) solution of D-isovaline (CAS Registry Number: 3059-97-0) (100 mg, 0.85 mmol), a dichloromethane (3 mL) solution of 1-iodo-4-isocyanatobenzene (CAS Registry Number: 15845-62-2) (418 mg, 1.71 mmol) was added, followed by stirring at room temperature overnight. Ethyl acetate, water and a 1N sodium hydroxide solution (1.02 mL, 1.02 mmol) were added to the resultant, and insoluble matter was filtered. After separating the thus obtained filtrate into an organic layer and an aqueous layer, a solid obtained by acidifying the aqueous layer with 2N hydrochloric acid was filtered, washed successively with water and n-hexane, and dried under reduced pressure to obtain 193 mg (62%) of the title compound in the form of a white solid. The obtained white solid was crystalline.

$^1$H-NMR (400 MHz, DMSO-D$_6$) δ: 12.60 (1H, br s), 8.73 (1H, s), 7.50-7.46 (2H, m), 7.19-7.15 (2H, m), 6.41 (1H, s), 1.95-1.86 (1H, m), 1.75-1.66 (1H, m), 1.39 (3H, s), 0.75 (3H, t, J=7.4 Hz).

MS m/z: 363 (M+H)$^+$.

[α]$_D^{25}$ −8.04° (c 1.0, Methanol).

Figure 6:
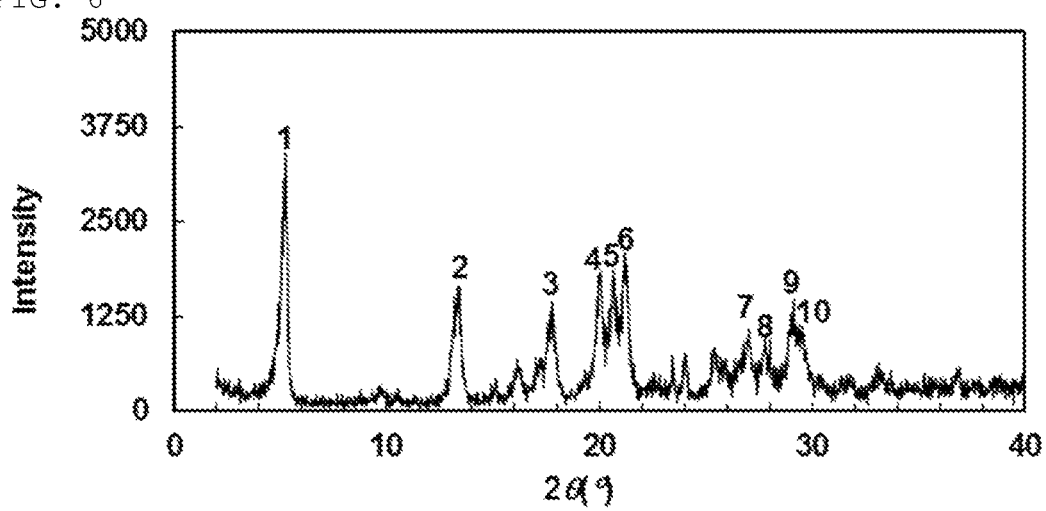
FIG. 6 is a powder X-ray diffraction diagram of crystals obtained in Example 31. The ordinate indicates diffraction intensity in count/sec. (cps), and the abscissa indicates a value of diffraction angle 2θ.

A powder X-ray diffraction pattern of the crystals obtained through irradiation with copper Kα radiation (λ=1.54 angstroms, scanning speed=20°/min) is illustrated in FIG. 6. Peaks each having relative intensity, calculated by assuming that the maximum peak intensity is 100, of 29 or more in FIG. 6 are shown in Table 6.

TABLE 6

| Peak No. | 2θ | d Value | Relative Intensity |
|---|---|---|---|
| 1 | 5.22 | 16.92 | 100 |
| 2 | 13.36 | 6.62 | 50 |
| 3 | 17.76 | 4.99 | 42 |
| 4 | 20.00 | 4.44 | 59 |
| 5 | 20.64 | 4.30 | 56 |
| 6 | 21.22 | 4.18 | 64 |
| 7 | 27.00 | 3.30 | 32 |
| 8 | 27.76 | 3.21 | 29 |
| 9 | 29.02 | 3.07 | 37 |
| 10 | 29.52 | 3.02 | 35 |

Example 32

2-{[(3-Cyanophenyl)carbamoyl]amino}-2-cyclopropylbutanoic acid

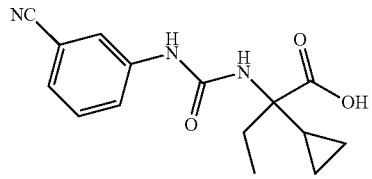

[Formula 54]

To a 1N sodium hydroxide (735 μL) solution of 2-amino-2-cyclopropylbutanoic acid monohydrochloride (CAS Registry Number: 1864016-20-5) (60 mg, 0.33 mmol), a dichloromethane/tetrahydrofuran (3:1, 4 mL) solution of 3-isocyanatobenzonitrile (CAS Registry Number: 16413-26-6) (144 mg, 1.00 mmol) was added, followed by stirring at room temperature overnight. Ethyl acetate, water and a 1N sodium hydroxide solution (0.4 mL) were added to the resultant, and an organic layer and an aqueous layer were separated. A solid obtained by acidifying the aqueous layer with 2N hydrochloric acid was filtered, washed successively with water and n-hexane, and dried under reduced pressure to obtain 22 mg (23%) of the title compound in the form of a white solid.

$^1$H-NMR (DMSO-D$_6$) δ: 12.79 (1H, s), 9.10 (1H, s), 7.88 (1H, t, J=1.8 Hz), 7.46 (1H, dq, J=8.3, 1.2 Hz), 7.39 (1H, t, J=7.8 Hz), 7.30 (1H, dt, J=7.6, 1.4 Hz), 6.30 (1H, s), 2.26-2.17 (1H, m), 1.99-1.90 (1H, m), 1.31-1.24 (1H, m), 0.77 (3H, t, J=7.4 Hz), 0.43-0.29 (4H, m).

MS m/z: 288 (M+H)$^+$.

Example 33

(+)-2-{[(3-Cyanophenyl)carbamoyl]amino}-2-cyclopropylbutanoic acid and (−)-2-{[(3-cyanophenyl)carbamoyl]amino}-2-cyclopropylbutanoic acid

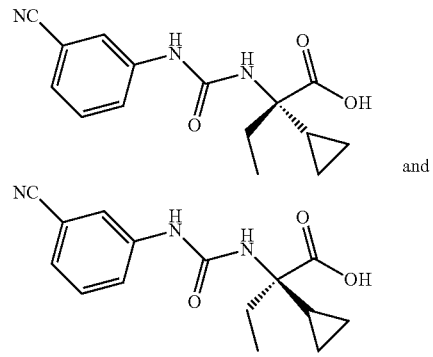

[Formula 55]

A supercritical CO$_2$ chromatography system of JASCO Corporation was used to perform optical resolution of 2-{[(3-cyanophenyl)carbamoyl]amino}-2-cyclopropylbutanoic acid (615 mg, 2.14 mmol), and under analysis conditions using an UPC$^2$ system of Waters as described below, 239 mg (39%) of the title compound in the form of a (+)-isomer having a retention time of 3.754 minutes was obtained in the form of a white solid, and 245 mg (40%) of the title compound in the form of a (−)-isomer having a retention time of 6.737 minutes was obtained in the form of a white solid. The white solid of the (+)-isomer of the title compound and the white solid of the (−)-isomer of the title compound thus obtained were both crystalline.

Figure 7:
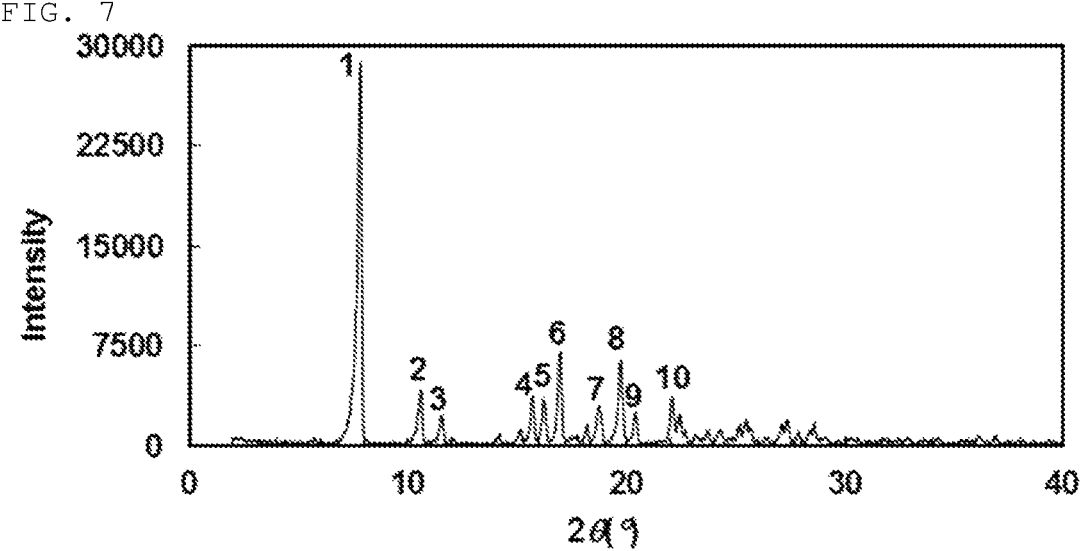
FIG. 7 is a powder X-ray diffraction diagram of crystalline (+)-2-{[(3-cyanophenyl)carbamoyl]amino}-2-cyclopropylbutanoic acid obtained in Example 33. The ordinate indicates diffraction intensity in count/sec. (cps), and the abscissa indicates a value of diffraction angle 2θ.

Analysis conditions:
Column: Acyon SFC CSP Amylose-c (5 μm) 250×4.6 mm I.D.
Elution solution: CO$_2$/ethanol (75/25)
Flow rate: 3.0 mL/min
Temperature: 35° C.
Back pressure: 13.8 MPa (2000 psi)
Back pressure: 10 MPa
Detection: UV (220 nm)
Injection amount: 5 μL (1.0 mg/mL)
Preparative conditions:
Column: Amylose-C (5 μm) 250×30 mm I.D.
Elution solution: CO$_2$/ethanol (75/25)
Flow rate: 120 mL/min
Temperature: 25° C.
Back pressure: 10 MPa
(+)-Isomer having retention time of 3.754 min:
$^1$H-NMR (DMSO-D$_6$) δ: 12.79 (1H, s), 9.10 (1H, s), 7.88 (1H, t, J=1.8 Hz), 7.46 (1H, dq, J=8.3, 1.2 Hz), 7.39 (1H, t, J=7.8 Hz), 7.30 (1H, dt, J=7.6, 1.4 Hz), 6.30 (1H, s), 2.26-2.17 (1H, m), 1.99-1.90 (1H, m), 1.31-1.24 (1H, m), 0.77 (3H, t, J=7.4 Hz), 0.43-0.29 (4H, m).
MS m/z: 288 (M+H)$^+$.
[α]$_D^{25}$ +25.81° (c 0.5, Methanol).
A powder X-ray diffraction pattern of crystals of the (+) isomer obtained through irradiation with copper Kα radiation (λ=1.54 angstroms, scanning speed=20°/min) is illustrated in FIG. 7. Peaks each having relative intensity, calculated by assuming that the maximum peak intensity is 100, of 8 or more in FIG. 7 are shown in Table 7.

TABLE 7

| Peak No. | 2θ | d Value | Relative Intensity |
| --- | --- | --- | --- |
| 1 | 7.82 | 11.30 | 100 |
| 2 | 10.58 | 8.35 | 15 |
| 3 | 11.54 | 7.66 | 8 |
| 4 | 15.70 | 5.64 | 13 |
| 5 | 16.22 | 5.46 | 13 |
| 6 | 16.96 | 5.22 | 24 |
| 7 | 18.74 | 4.73 | 11 |
| 8 | 19.72 | 4.50 | 22 |
| 9 | 20.42 | 4.35 | 9 |
| 10 | 22.08 | 4.02 | 13 |

(−)-Isomer having retention time of 6.737 min:
$^1$H-NMR (DMSO-D$_6$) δ: 12.79 (1H, s), 9.10 (1H, s), 7.88 (1H, t, J=1.8 Hz), 7.46 (1H, dq, J=8.3, 1.2 Hz), 7.39 (1H, t, J=7.8 Hz), 7.30 (1H, dt, J=7.6, 1.4 Hz), 6.30 (1H, s), 2.26-2.17 (1H, m), 1.99-1.90 (1H, m), 1.31-1.24 (1H, m), 0.77 (3H, t, J=7.4 Hz), 0.43-0.29 (4H, m).
MS m/z: 288 (M+H)$^+$.
$[α]_D^{25}$ −25.46° (c 0.5, Methanol).

Figure 8:
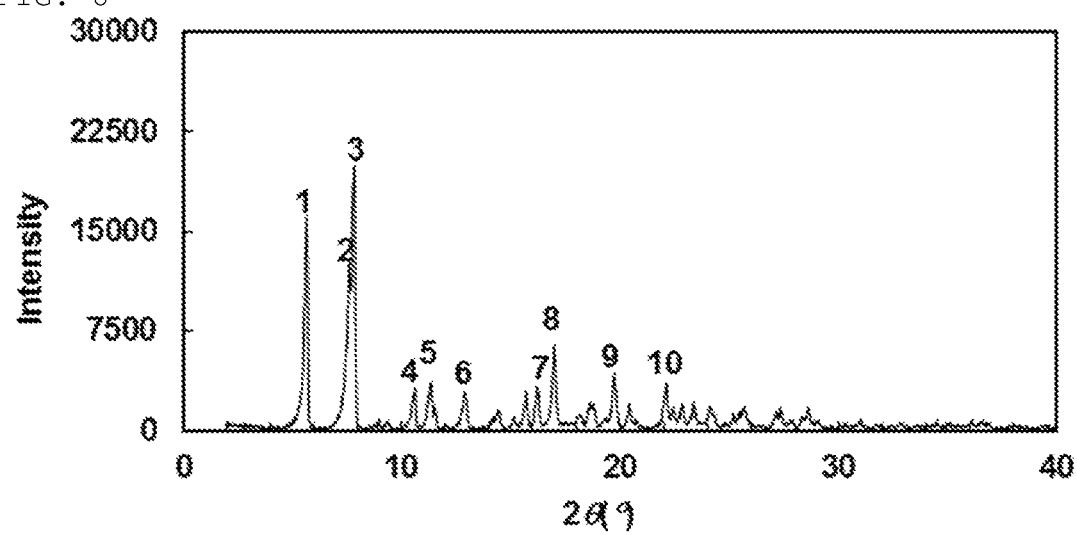
FIG. 8 is a powder X-ray diffraction diagram of crystalline (−)-2-{[(3-cyanophenyl)carbamoyl]amino}-2-cyclopropylbutanoic acid obtained in Example 33. The ordinate indicates diffraction intensity in count/sec. (cps), and the abscissa indicates a value of diffraction angle 2θ.

A powder X-ray diffraction pattern of crystals of the (−) isomer obtained through irradiation with copper Kα radiation (λ=1.54 angstroms, scanning speed=20°/min) is illustrated in FIG. 8. Peaks each having relative intensity, calculated by assuming that the maximum peak intensity is 100, of 15 or more in FIG. 8 are shown in Table 8.

TABLE 8

| Peak No. | 2θ | d Value | Relative Intensity |
| --- | --- | --- | --- |
| 1 | 5.64 | 15.66 | 77 |
| 2 | 7.60 | 11.62 | 60 |
| 3 | 7.82 | 11.30 | 100 |
| 4 | 10.60 | 8.34 | 15 |
| 5 | 11.34 | 7.80 | 19 |
| 6 | 12.92 | 6.85 | 15 |
| 7 | 16.24 | 5.45 | 16 |
| 8 | 16.98 | 5.22 | 30 |
| 9 | 19.72 | 4.50 | 21 |
| 10 | 22.10 | 4.02 | 18 |

Example 34

{[(3-Cyanophenyl)carbamoyl]amino}(dicyclopropyl)acetic acid

[Formula 56]

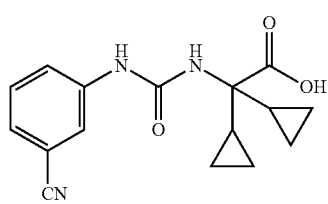

In the same manner as in Example 32, 80 mg (42%) of the title compound was obtained in the form of a white solid from amino(dicyclopropyl)acetic acid (CAS Registry Number: 6321-21-7) (100 mg, 0.64 mmol), a 1N sodium hydroxide solution (773 μL, 0.77 mmol) and 3-isocyanatobenzonitrile (CAS Registry Number: 16413-26-6) (186 mg, 1.29 mmol).
$^1$H-NMR (400 MHz, DMSO-D$_6$) δ: 8.83 (1H, s), 7.86 (1H, t, J=1.8 Hz), 7.47-7.43 (1H, m), 7.39 (1H, t, J=7.8 Hz), 7.30 (1H, dt, J=7.4, 1.4 Hz), 6.24 (1H, s), 1.26-1.19 (2H, m), 0.45-0.31 (8H, m).
MS m/z: 300 (M+H)$^+$.

Example 35

{[(4-Cyanophenyl)carbamoyl]amino}(dicyclopropyl)acetic acid

[Formula 57]

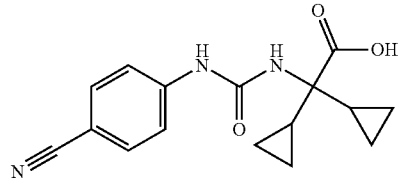

In the same manner as in Example 32, 24 mg (12%) of the title compound was obtained in the form of a white solid from amino(dicyclopropyl)acetic acid (CAS Registry Number: 6321-21-7) (100 mg, 0.64 mmol), a 1N sodium hydroxide solution (773 μL, 0.77 mmol) and 4-isocyanatobenzonitrile (CAS Registry Number: 40465-45-0) (186 mg, 1.29 mmol).
$^1$H-NMR (400 MHz, DMSO-D$_6$) δ: 12.33 (1H, s), 9.02 (1H, s), 7.66-7.63 (2H, m), 7.50-7.47 (2H, m), 6.31 (1H, s), 1.29-1.21 (2H, m), 0.48-0.33 (8H, m).
MS m/z: 300 (M+H)$^+$.

Example 36

2-{[(3-Cyano-5-fluorophenyl)carbamoyl]amino}-2-ethylbutanoic acid

[Formula 58]

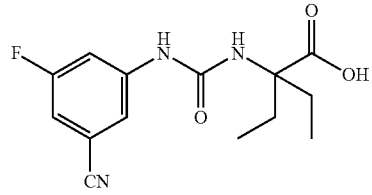

In the same manner as in Example 32, 20 mg (9%) of the title compound was obtained in the form of a pale yellow solid from 2-amino-2-ethylbutanoic acid (CAS Registry Number: 2566-29-2) (100 mg, 0.76 mmol), a 1N sodium hydroxide solution (915 μL, 0.92 mmol) and 3-fluoro-5-isocyanatobenzonitrile (CAS Registry Number: 1261862-00-3, ACS Chemical Neuroscience, 2013, 4, 1217-1228) (238 mg, 1.47 mmol).
$^1$H-NMR (400 MHz, DMSO-D$_6$) δ: 13.14 (1H, br s), 9.49 (1H, s), 7.57-7.52 (2H, m), 7.30-7.27 (1H, m), 6.56 (1H, s), 2.24-2.15 (2H, m), 1.73-1.64 (2H, m), 0.70 (6H, t, J=7.4 Hz).
MS m/z: 294 (M+H)$^+$.

Example 37

2-{[(4-Chloro-3-cyanophenyl)carbamoyl]amino}-2-ethylbutanoic acid

[Formula 59]

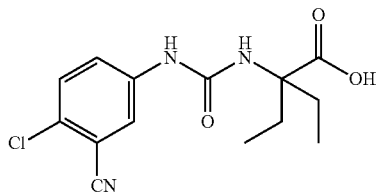

In the same manner as in Example 32, 6 mg (3%) of the title compound was obtained in the form of a pale yellow solid from 2-amino-2-ethylbutanoic acid (CAS Registry Number: 2566-29-2) (100 mg, 0.76 mmol), a 1N sodium hydroxide solution (1.83 mL, 1.83 mmol) and 2-chloro-5-isocyanatobenzonitrile (CAS Registry Number: 1261672-37-0) (468 mg, 2.62 mmol).

$^1$H-NMR (400 MHz, DMSO-D$_6$) δ: 8.18 (1H, br s), 8.18 (1H, br s), 7.48 (1H, d, J=8.6 Hz), 7.14 (1H, br s), 2.14-2.06 (2H, m), 1.69-1.61 (2H, m), 0.66 (6H, t, J=7.2 Hz).

MS m/z: 310, 312 (M+H)$^+$.

Example 38

({[4-(Cyanomethyl)phenyl]carbamoyl}amino)(dicyclopropyl)acetic acid

[Formula 60]

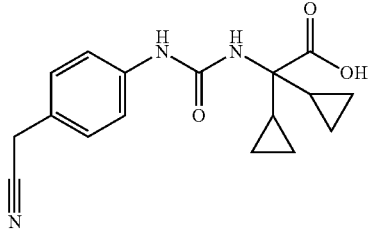

In the same manner as in Example 32, 137 mg (68%) of the title compound was obtained in the form of a white solid from amino(dicyclopropyl)acetic acid (CAS Registry Number: 6321-21-7) (100 mg, 0.64 mmol), a 1N sodium hydroxide solution (773 µL, 0.77 mmol) and (4-isocyanatophenyl)acetonitrile (CAS Registry Number: 59513-89-2) (204 mg, 1.29 mmol).

$^1$H-NMR (400 MHz, DMSO-D$_6$) δ: 12.21 (1H, br s), 8.55 (1H, s), 7.32-7.30 (2H, m), 7.15 (2H, d, J=8.6 Hz), 6.07 (1H, s), 3.88 (2H, s), 1.25-1.18 (2H, m), 0.44-0.30 (8H, m).

MS m/z: 314 (M+H)$^+$.

Example 39

2-({[4-(1-Cyanocyclopropyl)phenyl]carbamoyl}amino)-2-ethylbutanoic acid

[Formula 61]

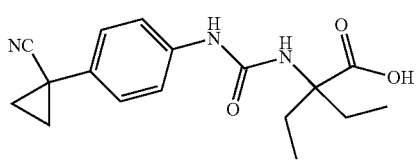

To a toluene (3.79 mL) solution of triphosgene (377 mg, 1.27 mmol), a 1,4-dioxane (3.79 mL) solution of 1-(4-aminophenyl)cyclopropanecarbonitrile (CAS Registry Number: 108858-86-2) (300 mg, 1.90 mmol) was added, followed by stirring at 100° C. for 4 hours. The resultant was cooled to room temperature, insoluble matter was filtered with toluene, and the resultant was concentrated under reduced pressure to obtain 1-(4-isocyanatophenyl)cyclopropanecarbonitrile as a crude product in the form of a light brown solid.

In the same manner as in Example 19, 201 mg (84%) of the title compound was obtained in the form of a pale yellow solid from the thus obtained crude product, 2-amino-2-ethylbutanoic acid (CAS Registry Number: 2566-29-2) (100 mg, 0.76 mmol), a 1N sodium hydroxide solution (0.92 mL, 0.92 mmol) and sodium hydrogen carbonate (128 mg, 1.52 mmol).

$^1$H-NMR (400 MHz, DMSO-D$_6$) δ: 12.99 (1H, br s), 8.97 (1H, s), 7.35-7.31 (2H, m), 7.15-7.12 (2H, m), 6.33 (1H, s), 2.23-2.14 (2H, m), 1.72-1.61 (4H, m), 1.35 (2H, dd, J=8.0, 5.3 Hz), 0.70 (6H, t, J=7.4 Hz).

MS m/z: 316 (M+H)$^+$.

Example 40

2-({[4-(1-Cyanoethyl)phenyl]carbamoyl}amino)-2-ethylbutanoic acid

[Formula 62]

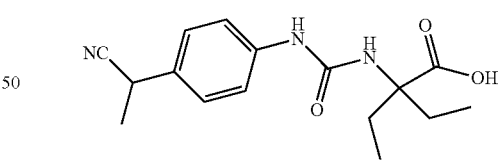

To a toluene (4.1 mL) solution of triphosgene (408 mg, 1.37 mmol), a 1,4-dioxane (4.1 mL) solution of 2-(4-aminophenyl)propanenitrile (CAS Registry Number: 28694-90-8) (300 mg, 2.05 mmol) was added, followed by stirring at 100° C. for 3.5 hours. The resultant was cooled to room temperature, insoluble matter was filtered with toluene, and the resultant was concentrated under reduced pressure to obtain 1-(4-isocyanatophenyl)propanenitrile as a crude product in the form of a light brown oil.

In the same manner as in Example 19, 178 mg (77%) of the title compound was obtained in the form of a white solid from the thus obtained crude product, 2-amino-2-ethylbutanoic acid (CAS Registry Number: 2566-29-2) (100 mg, 0.76 mmol), a 1N sodium hydroxide solution (915 µL, 0.92 mmol) and sodium hydrogen carbonate (128 mg, 1.52 mmol).

¹H-NMR (400 MHz, DMSO-D₆) δ: 13.00 (1H, br s), 8.97 (1H, s), 7.36-7.33 (2H, m), 7.21-7.18 (2H, m), 6.34 (1H, s), 4.14 (1H, q, J=7.3 Hz), 2.24-2.15 (2H, m), 1.72-1.63 (2H, m), 1.45 (3H, d, J=7.4 Hz), 0.70 (6H, t, J=7.2 Hz).

MS m/z: 304 (M+H)⁺.

Example 41

2-[(Biphenyl-4-ylcarbamoyl)amino]-2-ethylbutanoic acid

[Formula 63]

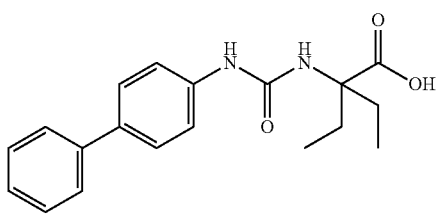

41a

Methyl 2-[(biphenyl-4-ylcarbamoyl)amino]-2-ethylbutanoic acid

To a N,N-dimethylformamide (5.12 mL) suspension of 4-isocyanatobiphenyl (CAS Registry Number: 92-95-5) (200 mg, 1.02 mmol), methyl 2-amino-2-ethylbutanoic acid (CAS Registry Number: 70974-26-4) (223 mg, 1.54 mmol) was added, followed by stirring at 50° C. for 8 hours, and then at room temperature overnight. Water was added thereto, the resultant was extracted with ethyl acetate, and the thus obtained extract was washed successively with water and a saturated saline solution, and dried over anhydrous sodium sulfate. A residue obtained through filtration and concentration under reduced pressure was purified by silica gel column chromatography [elution solvent: n-hexane/ethyl acetate=3/1-1/1 (V/V)] to obtain 222 mg (64%) of the title compound in the form of a colorless solid.

¹H-NMR (400 MHz, CDCl₃) δ: 7.54-7.50 (4H, m), 7.41-7.34 (4H, m), 7.31-7.26 (1H, m), 6.40 (1H, s), 5.74 (1H, s), 3.75 (3H, s), 2.53-2.43 (2H, m), 1.85-1.75 (2H, m), 0.77 (6H, t, J=7.4 Hz).

41b 3-(Biphenyl-4-yl)-5,5-diethylimidazolidine-2,4-dione

To a methanol/tetrahydrofuran (2:3, 5 mL) suspension of the methyl 2-[(biphenyl-4-ylcarbamoyl)amino]-2-ethylbutanoic acid (222 mg, 0.65 mmol) obtained in Example 41a, a 1N sodium hydroxide solution (1.30 mL, 1.30 mmol) was added, followed by stirring at room temperature for 2.5 hours. The resultant was acidified by adding 1N hydrochloric acid, and was concentrated under reduced pressure. Water was added thereto, the resultant was extracted with ethyl acetate, and the thus obtained extract was washed with a saturated saline solution and dried over anhydrous sodium sulfate. A solid obtained by adding diisopropyl ether to a residue obtained by filtration and concentration under reduced pressure was filtered, washed with diisopropyl ether, and dried under reduced pressure to obtain 183 mg (91%) of the title compound in the form of a solid.

¹H-NMR (400 MHz, CDCl₃) δ: 7.65-7.62 (2H, m), 7.56-7.53 (2H, m), 7.44-7.40 (4H, m), 7.36-7.31 (1H, m), 5.19 (1H, br s), 2.02-1.93 (2H, m), 1.77-1.68 (2H, m), 0.97 (6H, t, J=7.4 Hz).

MS m/z: 309 (M+H)⁺.

41c

2-[(Biphenyl-4-ylcarbamoyl)amino]-2-ethylbutanoic acid

To a methanol/tetrahydrofuran (2:1, 6 mL) solution of the 3-(biphenyl-4-yl)-5,5-diethylimidazolidine-2,4-dione (180 mg, 0.58 mmol) obtained in Example 41b, a 5N sodium hydroxide solution (1.17 mL, 5.84 mmol) was added, followed by stirring at 70° C. for 13 hours. The resultant was cooled to room temperature and concentrated under reduced pressure, ethyl acetate and water were added thereto, and an organic layer and an aqueous layer were separated. A solid obtained by acidifying the aqueous layer with 2N hydrochloric acid was filtered, washed successively with water and diisopropyl ether, and dried under reduced pressure to obtain 165 mg (87%) of the title compound in the form of a colorless solid.

¹H-NMR (400 MHz, DMSO-D₆) δ: 13.02 (1H, br s), 9.00 (1H, s), 7.58-7.56 (2H, m), 7.51-7.48 (2H, m), 7.44-7.37 (4H, m), 7.28-7.24 (1H, m), 6.37 (1H, s), 2.29-2.17 (2H, m), 1.73-1.65 (2H, m), 0.72 (6H, t, J=7.4 Hz).

MS m/z: 327 (M+H)⁺.

Example 42

2-Ethyl-2-{[(2'-fluorobiphenyl-4-yl)carbamoyl]amino}butanoic acid

[Formula 64]

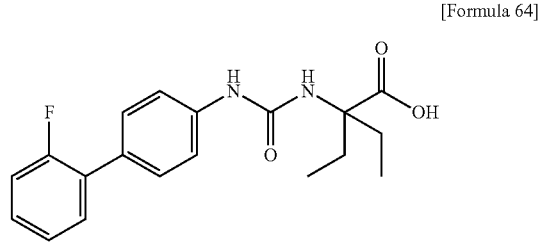 [SMILES: CCC(CC)(NC(=O)Nc1ccc(-c2ccccc2F)cc1)C(=O)O]

42a 3-(4-Bromophenyl)-5,5-diethylimidazolidine-2,4-dione

To a tetrahydrofuran (55 mL) solution of 1-bromo-4-isocyanatobenzene (CAS Registry Number: 2493-02-9) (2.18 g, 11.0 mmol), methyl 2-amino-2-ethylbutanoic acid (CAS Registry Number: 70974-26-4) (2.40 g, 16.5 mmol) was added, followed by stirring at 70° C. for 5 hours, and then at room temperature overnight. Methanol (15 mL) and a 5N sodium hydroxide solution (4.40 mL, 22.0 mmol) were added thereto, followed by stirring at room temperature for 1 hour. The resultant was neutralized with 2N hydrochloric acid and concentrated under reduced pressure, water was added thereto, and the resultant was extracted with ethyl acetate. The thus obtained extract was washed with water and a saturated saline solution, and dried over anhydrous sodium sulfate. A solid obtained by filtration and concentration under reduced pressure was filtered, washed with diisopropyl ether, and dried under reduced pressure to obtain 3.15 g (92%) of the title compound in the form of a colorless solid.

$^1$H-NMR (400 MHz, CDCl$_3$) δ: 7.57-7.53 (2H, m), 7.28-7.24 (2H, m), 5.34 (1H, br s), 1.98-1.89 (2H, m), 1.75-1.66 (2H, m), 0.93 (6H, t, J=7.4 Hz).

42b 5,5-Diethyl-3-(2'-fluorobiphenyl-4-yl)imidazolidine-2,4-dione

To an acetonitrile/water (5:2, 2.7 mL) solution of the 3-(4-bromophenyl)-5,5-diethylimidazolidine-2,4-dione (59 mg, 0.19 mmol) obtained in Example 42a and (2-fluorophenyl)boronic acid (CAS Registry Number: 1993-03-9) (39.8 mg, 0.28 mmol), potassium carbonate (65.5 mg, 0.47 mmol) and tetrakis(triphenylphosphine)palladium (0) (11 mg, 0.01 mmol) were added, followed by stirring at 70° C. under a nitrogen atmosphere for 3 hours. The resultant was cooled to room temperature, water was added thereto, and the resultant was extracted with ethyl acetate. The thus obtained extract was washed with a saturated saline solution, and dried over anhydrous sodium sulfate. A residue obtained through filtration and concentration under reduced pressure was purified by silica gel column chromatography [elution solvent: n-hexane/ethyl acetate=9/1-1/2 (V/V)] to obtain 53 mg (86%) of the title compound in the form of a white solid.

$^1$H-NMR (400 MHz, CDCl$_3$) δ: 7.63-7.59 (2H, m), 7.46-7.38 (3H, m), 7.33-7.28 (1H, m), 7.21-7.10 (2H, m), 5.22 (1H, br s), 2.02-1.93 (2H, m), 1.77-1.68 (2H, m), 0.97 (6H, t, J=7.4 Hz).

42c

2-Ethyl-2-{[(2'-fluorobiphenyl-4-yl)carbamoyl]amino}butanoic acid

To a methanol/tetrahydrofuran (1:1, 2 mL) solution of the 5,5-diethyl-3-(2'-fluorobiphenyl-4-yl)imidazolidine-2,4-dione (53 mg, 0.16 mmol) obtained in Example 42b, a 5N sodium hydroxide solution (0.65 mL, 3.25 mmol) was added, followed by stirring at 70° C. for 12 hours. The resultant was cooled to room temperature and concentrated under reduced pressure, diethyl ether and water were added thereto, and an organic layer and an aqueous layer were separated. A solid obtained by acidifying the aqueous layer with 2N hydrochloric acid was filtered, washed successively with water and diisopropyl ether, and dried under reduced pressure to obtain 46 mg (82%) of the title compound in the form of a white solid.

$^1$H-NMR (400 MHz, DMSO-D$_6$) δ: 13.04 (1H, br s), 9.05 (1H, s), 7.47-7.20 (8H, m), 6.38 (1H, s), 2.26-2.17 (2H, m), 1.74-1.65 (2H, m), 0.72 (6H, t, J=7.4 Hz).

MS m/z: 345 (M+H)$^+$.

Example 43

2-Ethyl-2-({[4-piperidine-1-yl)phenyl]carbamoyl}amino)butanoic acid

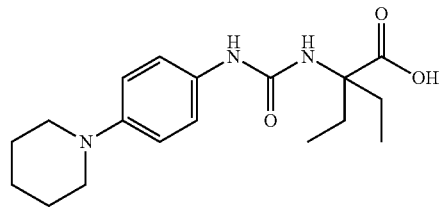

[Formula 65]

43a

2-Ethyl-2-({[4-piperidine-1-yl)phenyl]carbamoyl}amino)butanoic acid

A 1,4-dioxane (4.88 mL) suspension of the 3-(4-bromophenyl)-5,5-diethylimidazolidine-2,4-dione (152 mg, 0.49 mmol) obtained in Example 42a, piperidine (135 μL, 1.37 mmol), a chloro(2-dicyclohexylphosphino-2',6'-diisopropoxy-1,1'-biphenyl)[2-(2-aminoethylphenyl)]palladium (II) methyl-tert-butyl ether adduct (CAS Registry Number: 1028206-60-1) (19.9 mg, 0.02 mmol), sodium tert-butoxide (141 mg, 1.47 mmol) and 2-dicyclohexylphosphino-2',6'-diisopropoxybiphenyl (CAS Registry Number: 787618-22-8) (11.4 mg, 0.02 mmol) was stirred at 100° C. under a nitrogen atmosphere for 5 hours. The resultant was cooled to room temperature, water was added thereto, and the resultant was extracted with ethyl acetate. The thus obtained extract was washed successively with water and a saturated saline solution, and dried over anhydrous sodium sulfate. A residue obtained through filtration and concentration under reduced pressure was purified by silica gel column chromatography [elution solvent: n-hexane/ethyl acetate=9/1-1/2 (V/V)] to obtain 143 mg (93%) of the title compound in the form of a colorless solid.

$^1$H-NMR (400 MHz, CDCl$_3$) δ: 7.16-7.12 (2H, m), 6.94-6.90 (2H, m), 5.31 (1H, br s), 3.16-3.13 (4H, m), 1.97-1.88 (2H, m), 1.72-1.63 (6H, m), 1.57-1.51 (2H, m), 0.93 (6H, t, J=7.4 Hz).

43b

2-Ethyl-2-({[4-(piperidine-1-yl)phenyl]carbamoyl}amino)butanoic acid

To a methanol/tetrahydrofuran (1:1, 2 mL) solution of the 2-ethyl-2-({[4-(piperidine-1-yl)phenyl]carbamoyl}amino)butanoic acid (143 mg, 0.45 mmol) obtained in Example 43a, a 5N sodium hydroxide solution (907 μL, 4.53 mmol) was added, followed by stirring at 70° C. for 8.5 hours. The resultant was cooled to room temperature and concentrated under reduced pressure. Diethyl ether and water were added to the thus obtained residue, and an organic layer and an aqueous layer were separated. A solid obtained by acidifying the aqueous layer with 2N hydrochloric acid was filtered, washed successively with water and diisopropyl ether, and dried under reduced pressure to obtain 119 mg (79%) of the title compound in the form of a light brown solid.

$^1$H-NMR (400 MHz, DMSO-D$_6$) δ: 12.90 (1H, br s), 8.56 (1H, s), 7.15 (2H, d, J=9.0 Hz), 6.77 (2H, d, J=9.0 Hz), 6.16 (1H, s), 2.96-2.93 (4H, m), 2.22-2.13 (2H, m), 1.71-1.62 (2H, m), 1.60-1.54 (4H, m), 1.48-1.42 (2H, m), 0.70 (6H, t, J=7.4 Hz).

MS m/z: 334 (M+H)$^+$.

Example 44

2-({[4-(3,3-Difluoropyrrolidine-1-yl)phenyl]carbamoyl}amino)-2-ethylbutanoic acid

[Formula 66]

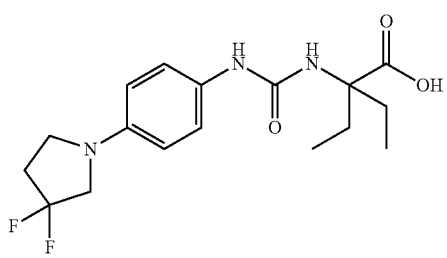

44a

3-[4-(3,3-Difluoropyrrolidine-1-yl)phenyl]-5,5-diethylimidazolidine-2,4-dione

In the same manner as in Example 43a, 117 mg (71%) of the title compound was obtained in the form of a white solid from the 3-(4-bromophenyl)-5,5-diethylimidazolidine-2,4-dione (152 mg, 0.49 mmol) obtained in Example 42a, 3,3-difluoropyrrolidine hydrochloride (CAS Registry Number: 163457-23-6) (196 mg, 1.37 mmol), a chloro(2-dicyclohexylphosphino-2',6'-diisopropoxy-1,1'-biphenyl)[2-(2-aminoethylphenyl)]palladium (II) methyl-tert-butyl ether adduct (CAS Registry Number: 1028206-60-1) (19.9 mg, 0.02 mmol), sodium tert-butoxide (272 mg, 2.83 mmol) and 2-dicyclohexylphosphino-2',6'-diisopropoxybiphenyl (CAS Registry Number: 787618-22-8) (11.4 mg, 0.02 mmol).

$^1$H-NMR (400 MHz, CDCl$_3$) δ: 7.18-7.15 (2H, m), 6.57-6.54 (2H, m), 5.22 (1H, br s), 3.65 (2H, t, J=13.3 Hz), 3.50 (2H, t, J=7.2 Hz), 2.52-2.41 (2H, m), 1.98-1.89 (2H, m), 1.73-1.64 (2H, m), 0.93 (6H, t, J=7.4 Hz).

44b 2-({[4-(3,3-Difluoropyrrolidine-1-yl)phenyl]carbamoyl}amino)-2-ethylbutanoic acid In the same manner as in Example 43b, 60 mg (49%) of the title compound was obtained in the form of a light brown solid from the 3-[4-(3,3-difluoropyrrolidine-1-yl)phenyl]-5,5-diethylimidazolidine-2,4-dione (117 mg, 0.35 mmol) obtained in Example 44a and a 5N sodium hydroxide solution (694 µL, 3.47 mmol).

$^1$H-NMR (400 MHz, DMSO-D$_6$) δ: 12.92 (1H, br s), 8.56 (1H, s), 7.23-7.19 (2H, m), 6.56-6.52 (2H, m), 6.18 (1H, s), 3.61 (2H, t, J=13.7 Hz), 3.39 (2H, t, J=7.2 Hz), 2.57-2.45 (2H, m), 2.26-2.17 (2H, m), 1.75-1.66 (2H, m), 0.74 (6H, t, J=7.4 Hz).

MS m/z: 356 (M+H)$^+$.

Example 45

(+)-N-{[4-(Trifluoromethoxy)phenyl]carbamoyl}-L-isovaline

[Formula 67]

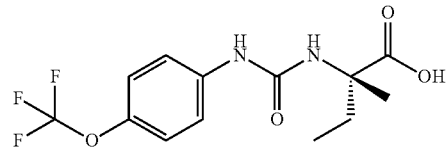

In the same manner as in Example 4, 208 mg (71%) of the title compound was obtained in the form of a white solid from L-isovaline (CAS Registry Number: 595-40-4) (100 mg, 0.85 mmol), 1N sodium hydroxide (1.02 mL, 1.02 mmol) and 1-isocyanato-4-(trifluoromethoxy)benzene (CAS Registry Number: 35037-73-1) (347 mg, 1.71 mmol).

$^1$H-NMR (400 MHz, DMSO-D$_6$) δ: 12.66 (1H, br s), 8.87 (1H, s), 7.48-7.44 (2H, m), 7.23-7.22 (2H, m), 6.47 (1H, s), 2.01-1.92 (1H, m), 1.81-1.72 (1H, m), 1.45 (3H, s), 0.81 (3H, t, J=7.4 Hz).

MS m/z: 321 (M+H)$^+$.

$[α]_D^{25}$+8.670 (c 0.5, Methanol).

Example 46

(+)-N-{[4-(Difluoromethoxy)phenyl]carbamoyl}-L-isovaline

[Formula 68]

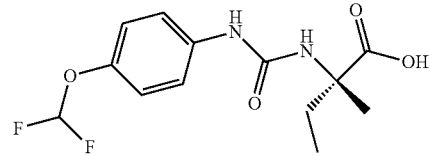

In the same manner as in Example 4, 103 mg (40%) of the title compound was obtained in the form of a white solid from L-isovaline (CAS Registry Number: 595-40-4) (100 mg, 0.85 mmol), 1N sodium hydroxide (1.02 mL, 1.02 mmol) and 1-(difluoromethoxy)-4-isocyanatobenzene (CAS Registry Number: 58417-15-5) (316 mg, 1.71 mmol).

$^1$H-NMR (400 MHz, DMSO-D$_6$) δ: 12.65 (1H, br s), 8.75 (1H, s), 7.43-7.40 (2H, m), 7.12 (1H, t, J=74.7 Hz), 7.10-7.06 (2H, m), 6.44 (1H, s), 2.03-1.94 (1H, m), 1.83-1.74 (1H, m), 1.47 (3H, s), 0.83 (3H, t, J=7.4 Hz).

MS m/z: 303 (M+H)$^+$.

$[α]^5$+8.110 (c 1.0, Methanol).

Example 47

(+)-N-{[4-(Difluoromethoxy)-3-fluorophenyl]carbamoyl}-L-isovaline

[Formula 69]

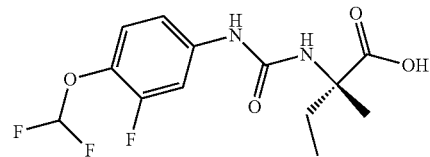

To a toluene (14.1 mL) solution of 4-(difluoromethoxy)-3-fluoroaniline (CAS Registry Number: 83190-01-6) (500 mg, 2.82 mmol) and triethylamine (944 μL, 6.77 mmol), triphosgene (436 mg, 1.47 mmol) was added, followed by stirring at room temperature for 2.5 hours. Insoluble matter was filtered with toluene, and the thus obtained filtrate was concentrated under reduced pressure to obtain 1-(difluoromethoxy)-2-fluoro-4-isocyanatobenzene as a crude product in the form of a light brown oil.

In the same manner as in Example 4, 10 mg (3%) of the title compound was obtained in the form of a white solid from the thus obtained crude product, L-isovaline (CAS Registry Number: 595-40-4) (110 mg, 0.94 mmol), and 1N sodium hydroxide (1 mL, 1 mmol).

$^1$H-NMR (400 MHz, DMSO-D$_6$) δ: 12.65 (1H, br s), 8.91 (1H, s), 7.54 (1H, dd, J=13.5, 2.5 Hz), 7.18 (1H, t, J=9.0 Hz), 7.06 (1H, t, J=73.5 Hz), 6.96 (1H, dq, J=8.9, 1.2 Hz), 6.47 (1H, s), 1.96-1.87 (1H, m), 1.76-1.67 (1H, m), 1.40 (3H, s), 0.75 (3H, t, J=7.4 Hz).

MS m/z: 321 (M+H)$^+$.

$[α]_D^{25}$+9.05° (c 1.0, Methanol).

Example 48

(+)-N-[(4-Chlorophenyl)carbamoyl]-L-isovaline

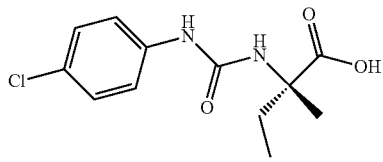

[Formula 70]

In the same manner as in Example 4, 292 mg (63%) of the title compound was obtained in the form of a white solid from L-isovaline (CAS Registry Number: 595-40-4) (200 mg, 1.71 mmol), 1N sodium hydroxide (2.05 mL, 2.05 mmol) and 1-chloro-4-isocyanatobenzene (CAS Registry Number: 104-12-1) (524 mg, 3.41 mmol).

$^1$H-NMR (400 MHz, DMSO-D$_6$) δ: 12.56 (1H, br s), 8.74 (1H, s), 7.36-7.32 (2H, m), 7.23-7.19 (2H, m), 6.39 (1H, s), 1.96-1.87 (1H, m), 1.76-1.67 (1H, m), 1.40 (3H, s), 0.76 (3H, t, J=7.4 Hz).

MS m/z: 271, 273 (M+H)$^+$.

$[α]_D^{25}$+9.26° (c 1.0, Methanol).

Example 49

(+)-N-[(4-Bromophenyl)carbamoyl]-L-isovaline

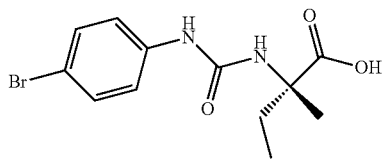

[Formula 71]

In the same manner as in Example 4, 193 mg (62%) of the title compound was obtained in the form of a white solid from L-isovaline (CAS Registry Number: 595-40-4) (115 mg, 0.98 mmol), 1N sodium hydroxide (1.18 mL, 1.18 mmol) and 1-bromo-4-isocyanatobenzene (CAS Registry Number: 2493-02-9) (389 mg, 1.96 mmol).

$^1$H-NMR (400 MHz, DMSO-D$_6$) δ: 12.69 (1H, s), 8.83 (1H, s), 7.42-7.35 (4H, m), 6.49 (1H, s), 2.03-1.94 (1H, m), 1.83-1.76 (1H, m), 1.47 (3H, s), 0.83 (3H, t, J=7.4 Hz).

MS m/z: 315, 317 (M+H)$^+$.

$[α]^5$+9.100 (1.0, Methanol)

Example 50

(+)-N-[(4-Iodophenyl)carbamoyl]-L-isovaline

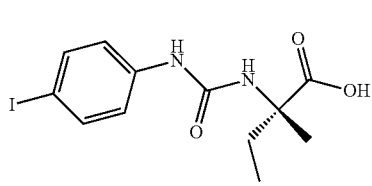

[Formula 72]

In the same manner as in Example 4, 194 mg (55%) of the title compound was obtained in the form of a white solid from L-isovaline (CAS Registry Number: 595-40-4) (115 mg, 0.98 mmol), 1N sodium hydroxide (1.18 mL, 1.18 mmol) and 1-iodo-4-isocyanatobenzene (CAS Registry Number: 15845-62-2) (481 mg, 1.96 mmol).

$^1$H-NMR (400 MHz, DMSO-D$_6$) δ: 12.60 (1H, br s), 8.73 (1H, s), 7.50-7.46 (2H, m), 7.19-7.15 (2H, m), 6.41 (1H, s), 1.95-1.86 (1H, m), 1.75-1.66 (1H, m), 1.39 (3H, s), 0.75 (3H, t, J=7.4 Hz).

MS m/z: 363 (M+H)$^+$.

$[α]_D^{25}$+8.52° (c 0.89, Methanol).

(Test Example 1) Tryptophanase Enzyme Inhibitory Activity

Tryptophanase inhibitory activity was evaluated by a method using lactate dehydrogenase (LDH). The reaction time-dependent reduction in NADH conjugated with the enzymatic reaction, with LDH, of pyruvic acid produced through the enzymatic reaction of L-tryptophan as a substrate with tryptophanase, was measured with a spectrophotometer (Phillips-R S et al., Biochemistry, 23, 6228-6234 (1984)). Enzyme inhibitory activity obtained without adding a test compound (by adding DMSO alone) in the presence of tryptophanase was used as a control. As the enzyme, tryptophanase of *Bacteroides* thetaiotamicron (Genbank accession number: HC914434.1) was used.

A test compound solution was prepared by dissolving each test compound in DMSO in an arbitrary concentration (from 30 mM to 30 nM at 10-fold common ratio). LDH, NADH and L-tryptophan were prepared, using distilled water, respectively to concentrations of 80 units/mL, 10 mM and 50 mM. *Bacteroides* tryptophanase was prepared to 30 mg/mL. A potassium phosphate buffer was used as the buffer. Compositions of reaction solutions are shown in Table 9.

TABLE 9

| Composition of Reaction Solution | Concentration | Final Concentration | Reaction Solution | | |
|---|---|---|---|---|---|
| | | | Reaction Solution A | Reaction Solution B | Reaction Solution C |
| Distilled Water | — | — | | | |
| KPB (pH 8.3) | 1M | 125 mM | | | |
| LDH | 80 units/mL | 2.5 units/mL | | | |
| NADH | 10 mM | 0.3125 mM | | | |
| Bacteroides Tryptophanase | 30 mg/mL | 0.015 mg/mL | | | |
| Test Compound Solution | Arbitrary Concentration | 1/100 of Preparation Concentration | | | |
| L-Tryptophan | 50 mM | 10 mM | | | |

A reaction solution A was dispensed at 284.8 μL per well into a 96-well plate, and the test compound solution was added at 3.2 μL per well to obtain a final concentration of 1/100 (reaction solution B). The reaction solution B was incubated at 37° C. for 30 minutes, L-tryptophan was added thereto at 32 μL per well to obtain a final concentration of 10 mM (reaction solution C), and the enzyme reaction was performed at 37° C. over 30 minutes with absorbance at 340 nm measured for monitoring the NADH loss. Based on the NADH loss, the tryptophanase inhibitory activity of the compound was evaluated. Besides, the following compounds were similarly tested instead of the test compound.

Compound A: 2-ethyl-2-[(phenylcarbamoyl)amino]butanoic acid

[Formula 73]

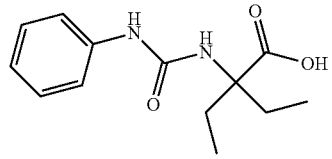

Compound B: 2-{[(3-chlorophenyl)carbamoyl]amino}-2-ethylbutanoic acid

[Formula 74]

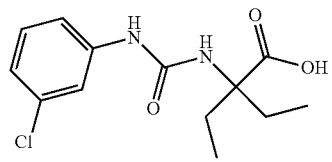

Compound C: 2-{[(4-chlorophenyl)carbamoyl]amino}-2-ethylbutanoic acid

[Formula 75]

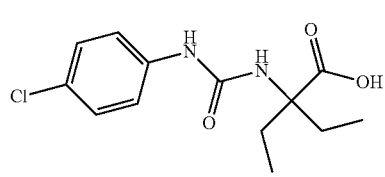

Compound D: 2-ethyl-2-{[(4-fluorophenyl)carbamoyl]amino}butanoic acid

[Formula 76]

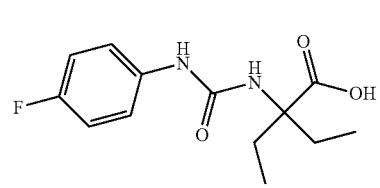

Compound E: 2-ethyl-2-{[(3-fluorophenyl)carbamoyl]amino}butanoic acid

[Formula 77]

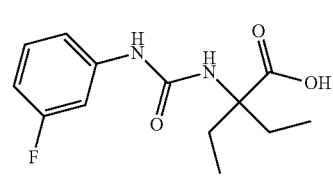

Compound F: 2-{[(3-cyanophenyl)carbamoyl]amino}-2-ethylbutanoic acid

[Formula 78]

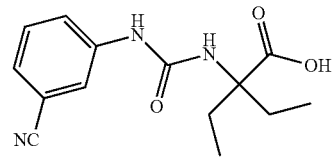

Compound G: 2-({[4-(cyanomethyl)phenyl]carbamoyl}amino)-2-ethylbutanoic acid

[Formula 79]

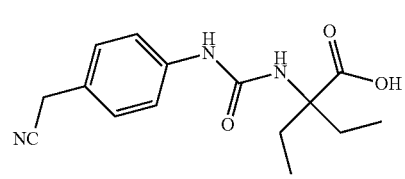

and

Compound H: 2-ethyl-2-[(thiophen-3-ylcarbamoyl)amino]butanoic acid

[Formula 80]

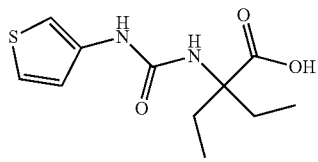

Inhibitory activities (IC50, μM) of these test compounds are shown in Table 10-1 and Table 10-2.

TABLE 10

| Test Compound | Bacteroides Activity of Inhibiting Tryptophanase (IC50, μM) |
|---|---|
| Compound of Example 1 | 3.7 |
| Compound of Example 2 | 20.3 |
| Compound of Example 3 | 8.7 |
| Compound of Example 4 | 8.8 |
| Compound of Example 5 | 1.7 |
| Compound of Example 6 | 5.3 |
| Compound of Example 7 | 0.3 |
| Compound of Example 8 | 12.8 |
| Compound of Example 10 | 1.9 |
| Compound of Example 11 | 0.6 |
| Compound of Example 13 | 6.7 |
| Compound of Example 14 | 0.4 |
| Compound of Example 15 | 13.5 |
| Compound of Example 16 | 4.2 |
| Compound of Example 17 | 12.3 |
| Compound of Example 18 | 5.3 |
| Compound of Example 19 | 35.6 |
| Compound of Example 20 | 11.6 |
| Compound of Example 21 | 5.0 |
| Compound of Example 22 | 2.1 |
| Compound of Example 23 | 5.2 |
| Compound of Example 24 | 33.2 |
| Compound of Example 25 | 26.8 |
| Compound of Example 26 | 13.2 |
| Compound of Example 27 | 6.0 |
| Compound of Example 28 | 3.2 |
| Compound of Example 29 | 15.5 |
| Compound of Example 30 | 22.1 |
| Compound of Example 31 | 7.9 |
| Compound of Example 32 | 1.0 |
| (+) Isomer Compound of Example 33 | 0.6 |
| (−) Isomer Compound of Example 33 | 7.70 |
| Compound of Example 34 | 1.8 |
| Compound of Example 35 | 10.9 |
| Compound of Example 36 | 20.1 |
| Compound of Example 37 | 25.0 |
| Compound of Example 38 | 3.4 |
| Compound of Example 39 | 5.2 |
| Compound of Example 40 | 5.8 |
| Compound of Example 41 | 0.3 |
| Compound of Example 42 | 0.1 |
| Compound of Example 43 | 1.6 |
| Compound of Example 44 | 2.5 |
| Compound A | 20.0 |
| Compound B | 7.4 |
| Compound C | 16.0 |
| Compound D | 38.1 |
| Compound E | 18.9 |
| Compound F | 16.5 |
| Compound G | 4.7 |
| Compound H | 34.1 |

In this manner, the compounds of the present invention exhibited excellent tryptophanase inhibitory activity. Accordingly, the compounds of the present invention are useful as pharmaceuticals as an agent for reducing indoxyl sulfate in the blood, an agent for preventing or treating a disease caused by an increase in indoxyl sulfate in the blood, an agent for delaying transition to renal replacement therapy in a patient in a period of conservative treatment of chronic kidney disease, and an agent for suppressing worsening of remaining renal function in a patient after transition to renal replacement therapy.

(Test Example 2) Indole Production Suppressing Effect

The effect of a tryptophanase inhibitory compound to suppress indole production from a viable bacterium can be evaluated through the following operation.

When *E. coli* (*Escherichia Coli*) is used as a strain known to produce indole, the strain is cultured in an LB medium at 37° C. for 12 to 18 hours under anaerobic conditions, and then, suspended in an assay medium (5 mM L-Tryptophan/PBS(+)/25 mM HEPES (pH8)) in such a manner as to obtain O.D. of about 0.3. When bacteroides is used, the strain is cultured in a modified GAM medium at 37° C. for 12 to 18 hours under anaerobic conditions, and then suspended in an assay medium (5 mM L-Tryptophan/PBS(+)/25 mM HEPES (pH8)) in such a manner as to obtain O.D. of about 1.1. The thus obtained viable bacterial suspension prepared to have a final concentration of a compound of 1 μM to 10 mM is dispensed at 200 μL per well into a 96-well plate and cultured at 37° C. for 2 to 4 hours under anaerobic conditions, and O.D., an ATP concentration (that can be quantitatively determined by using BacTiter-Glo (Promega Corporation)) and an indole concentration in the culture supernatant (that can be quantitatively determined by utilizing Ehrlich reaction) are measured. The effect of the tryptophanase inhibitory compound to suppress indole production from a viable bacterium can be evaluated depending on the degree of lowering of the indole concentration in the culture supernatant. It can be checked whether or not the effect is derived from a function other than tryptophanase inhibition, such as a bactericidal function or a bacterial growth inhibitory function, depending on lowering of the O.D. or reduction in the ATP concentration or by performing a generally practiced antibacterial activity test (a MIC (minimum growth inhibition concentration) test) using levofloxacin or the like as a positive control.

The activities of inhibiting indole production of the compounds of the respective examples shown in Table 11 were measured by the above-described method using *Bacteroides* to evaluate the effect of inhibiting indole production. The results are shown in Table 11.

TABLE 11

| Test Compound | Eroides Activity of Inhibiting Indole Production(IC50, μM) |
|---|---|
| Compound of Example 8 | 7 |
| Compound of Example 15 | 14 |
| Compound of Example 25 | 23 |
| Compound of Example 27 | 5 |
| Compound of Example 30 | 14 |

TABLE 11-continued

| Test Compound | Eroides Activity of Inhibiting Indole Production(IC50, µM) |
|---|---|
| Compound of Example 31 | <3 |
| (+) Isomer Compound of Example 33 | <3 |
| (−) Isomer Compound of Example 33 | 9 |
| Compound A | 8 |
| Compound B | <3 |
| Compound C | 6 |
| Compound D | 11 |
| Compound E | 7 |
| Compound F | 12 |
| Compound G | 8 |
| Compound H | 11 |

In this manner, the compounds of the present invention exhibited excellent activity of inhibiting indole production. Accordingly, the compounds of the present invention are useful as pharmaceuticals as an agent for reducing indoxyl sulfate in the blood, an agent for preventing or treating a disease caused by an increase in indoxyl sulfate in the blood, an agent for delaying transition to renal replacement therapy in a patient in a period of conservative treatment of chronic kidney disease, and an agent for suppressing worsening of remaining renal function in a patient after transition to renal replacement therapy.

(Test Example 3) Effect of Reducing Indoxyl Sulfate Concentration in the Plasma of Mice An effect of a tryptophanase inhibitory compound to reduce an indoxyl sulfate concentration in the plasma of a mouse can be evaluated through the following operation.

After fasting a male BALB/c mouse overnight, a tryptophanase compound dissolved or suspended at a concentration of 0.01 to 10 mg/mL in a 0.5% methylcellulose (MC) solution used as a solvent and a 0.5% MC solution are orally administered by gavage at a dose of 10 mL/kg respectively to a test compound group and to a solvent control group. When 30 minutes have elapsed after the administration of the test compound or the solvent, L-tryptophan, that is, a substrate of tryptophanase, is orally administered by gavage at a dose of 1 to 3 g/kg. The L-tryptophan is suspended in a 0.5% tragacanth solution. For 12 hours after the administration of the L-tryptophan, blood is collected over time from a tail vein by using a hematocrit tube. The thus obtained blood is centrifuged at 11,000 rpm for 5 minutes to collect plasma, and the indoxyl sulfate concentration in the plasma is measured singly by liquid chromatography (fluorescence detection) or its combination with a mass spectrometer used subsequently. The indoxyl sulfate concentration in the plasma of the test compound group against the indoxyl sulfate concentration in the plasma of the solvent control group is calculated as, for example, a ratio of the area under a curve of the indoxyl sulfate concentration, and thus, the efficacy of each compound in a living body can be compared.

The indoxyl sulfate concentrations in plasma obtained by using the compounds of the respective examples shown in Table 12 below were measured by the above-described method to evaluate the effect of reducing indoxyl sulfate concentration. The results are shown in Table 12.

TABLE 12

| Test Compound | Indoxyl Sulfate Reduction Effect in Male BALB/c Mouse Plasma (Indoxyl sulfate reduction effect in plasma 6 hours after administering L-tryptophan: ED75−, mg/kg) |
|---|---|
| Compound of Example 8 | 1 |
| Compound of Example 15 | 1 |
| Compound of Example 25 | 1 |
| Compound of Example 27 | 1 |
| Compound of Example 30 | 1 |
| Compound of Example 31 | 1 |
| (+) Isomer Compound of Example 33 | 1 |
| (−) Isomer Compound of Example 33 | >1 |
| Compound A | 1 |
| Compound B | >1 |
| Compound C | >1 |
| Compound D | 1 |
| Compound E | >1 |
| Compound F | 1 |
| Compound G | 1 |
| Compound H | 1 |

In this manner, the compounds of the present invention exhibited an excellent indoxyl sulfate-reducing function in plasma. Accordingly, the compounds of the present invention are useful as pharmaceuticals as an agent for reducing indoxyl sulfate in the blood, an agent for preventing or treating a disease caused by an increase in indoxyl sulfate in the blood, an agent for delaying transition to renal replacement therapy in a patient in a period of conservative treatment of chronic kidney disease, and an agent for suppressing worsening of remaining renal function in a patient after transition to renal replacement therapy.

(Formulation Example 1) Hard Capsule

A unit capsule was produced by filling each standard two-part hard gelatin capsule with 100 mg of the compound of Example 1 in the form of a powder, 150 mg of lactose, 50 mg of cellulose and 6 mg of magnesium stearate, and the resultant capsule was washed and then dried.

(Formulation Example 2) Soft Capsule

A soft capsule containing 100 mg of an active component was obtained by preparing a mixture of the compound of Example 2 in digestible oil such as soybean oil, cottonseed oil or olive oil and injecting the resultant into gelatin by using a positive displacement pump, and the resultant capsule was washed and then dried.

(Formulation Example 3) Tablet

A tablet was produced by an ordinary method using 100 mg of the compound of Example 3, 0.2 mg of colloidal silicon dioxide, 5 mg of magnesium stearate, 275 mg of microcrystalline cellulose, 11 mg of starch and 98.8 mg of lactose.

The resultant tablet may be coated with a coating if desired.

(Formulation Example 4) Suspension

A suspension containing, in 5 mL, 100 mg of the compound of Example 4 in the form of a fine powder, 100 mg of sodium carboxymethylcellulose, 5 mg of sodium benzoate, 1.0 g of a sorbitol solution (The Japanese Pharmacopoeia) and 0.025 mL of vanillin was produced.

INDUSTRIAL APPLICABILITY

The inventive compound (I) or a pharmacologically acceptable salt thereof has an excellent tryptophanase inhibitory effect, and is useful as an agent for reducing indoxyl sulfate in the blood, an agent for preventing or treating a disease caused by an increase in indoxyl sulfate in the blood, an agent for delaying transition to renal replacement therapy in a patient in a period of conservative treatment of chronic kidney disease, and an agent for suppressing worsening of remaining renal function in a patient after transition to renal replacement therapy.

The invention claimed is:

1. A compound represented by formula (I) or a pharmacologically acceptable salt thereof:

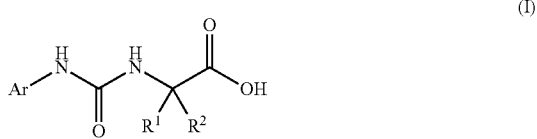

(I)

wherein
Ar represents a group represented by the following formula:

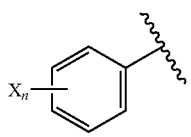

wherein $R^1$ represents a $C_3$-$C_6$ cycloalkyl group, $R^2$ represents a $C_2$-$C_6$ alkyl group or a $C_3$-$C_6$ cycloalkyl group, n represents 0, 1 or 2, and X each independently represents a halogen atom, a cyano group, a halogeno $C_1$-$C_6$ alkyl group, a cyano $C_1$-$C_6$ alkyl group, a cyano $C_3$-$C_6$ cycloalkyl group, a halogeno $C_1$-$C_6$ alkoxy group, a halogeno $C_1$-$C_6$ alkylthio group, a saturated cyclic amino group, a halogeno saturated cyclic amino group, a phenyl group or a halogeno phenyl group.

2. The compound according to claim 1 represented by formula (I-4), or a pharmacologically acceptable salt thereof:

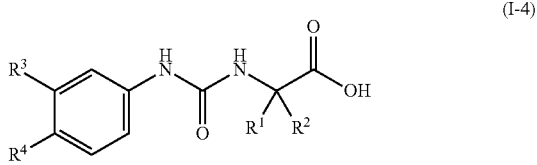

(I-4)

wherein $R^1$ represents a $C_3$-$C_6$ cycloalkyl group, $R^2$ represents a $C_2$-$C_6$ alkyl group or a $C_3$-$C_6$ cycloalkyl group, $R^3$ represents a hydrogen atom, a halogen atom or a cyano group, and $R^4$ represents a halogen atom, a cyano group, a halogeno $C_1$-$C_6$ alkyl group, a cyano $C_1$-$C_6$ alkyl group, a cyano $C_3$-$C_6$ cycloalkyl group, a halogeno $C_1$-$C_6$ alkoxy group, a halogeno $C_1$-$C_6$ alkylthio group, a saturated cyclic amino group, a halogeno saturated cyclic amino group, a phenyl group or a halogeno phenyl group.

3. The compound according to claim 1, or a pharmacologically acceptable salt thereof, wherein $R^1$ represents a cyclopropyl group.

4. The compound according to claim 1, or a pharmacologically acceptable salt thereof, wherein $R^2$ represents an ethyl group or a cyclopropyl group.

5. The compound according to claim 2, or a pharmacologically acceptable salt thereof, wherein $R^3$ represents a hydrogen atom, and $R^4$ represents a fluorine atom, a cyano group, a cyanomethyl group, a 2,2,2-trifluoroethyl group, a difluoromethoxy group or a trifluoromethoxy group.

6. The compound according to claim 2, or a pharmacologically acceptable salt thereof, wherein $R^3$ represents a cyano group, and $R^4$ represents a hydrogen atom.

7. The compound according to claim 1, or a pharmacologically acceptable salt thereof, selected from the group consisting of: dicyclopropyl({[4-(trifluoromethoxy)phenyl]carbamoyl}amino)acetic acid, 2-cyclopropyl-2-({[4-(trifluoromethoxy)phenyl]carbamoyl}amino)butanoic acid, 2-cyclopropyl-2-({[4-(difluoromethoxy)phenyl]carbamoyl}amino)butanoic acid, 2-cyclopropyl-2-[(phenylcarbamoyl)amino]butanoic acid, 2-cyclopropyl-2-{[(4-fluorophenyl)carbamoyl]amino}butanoic acid, and 2-{[(3-cyanophenyl)carbamoyl]amino}-2-cyclopropylbutanoic acid.

8. The compound according to claim 1, or a pharmacologically acceptable salt thereof, selected from the group consisting of: (2R)-2-{[(3-cyanophenyl)carbamoyl]amino}-2-cyclopropylbutanoic acid, and (2S)-2-{[(3-cyanophenyl)carbamoyl]amino}-2-cyclopropylbutanoic acid.

9. A pharmaceutical composition comprising, as an active ingredient, the compound according to claim 1, or a pharmacologically acceptable salt thereof.

10. A crystal of the compound according to claim 1, selected from the group consisting of:
a crystal of (+)-2-{[(3-cyanophenyl)carbamoyl]amino}-2-cyclopropylbutanoic acid having characteristic main peaks at interplanar spacings of 11.30, 8.35, 7.66, 5.64, 5.46, 5.22, 4.73, 4.50, 4.35 and 4.02 angstroms; and
a crystal of (−)-2-{[(3-cyanophenyl)carbamoyl]amino}-2-cyclopropylbutanoic acid having characteristic peaks at interplanar spacings of 15.66, 11.62, 11.30, 8.35, 7.80, 6.84, 5.45, 5.22, 4.5 and 4.02 angstroms;
all in powder X-ray diffraction obtained through irradiation with copper Kα line (wavelength $\lambda$=1.54 angstroms).

11. A pharmaceutical composition comprising, as an active ingredient, any one of the crystals of the compound according to claim 10.

12. A method for inhibiting tryptophanase in a mammal, comprising administering to a mammal an effective amount of a compound according to claim 1.

13. A method for reducing indoxyl sulfate in the blood of a mammal, comprising administering to a mammal an effective amount of a compound according to claim 1.

14. A method for suppressing worsening of renal function in a mammal, comprising administering to a mammal an effective amount of a compound according to claim 1.

15. A method for treating a disease caused by increase of indoxyl sulfate in blood, comprising administering to a mammal an effective amount of a compound according to claim 1.

16. The method of claim 12, wherein the compound, or a pharmacologically acceptable salt thereof, selected from the group consisting of:
- dicyclopropyl({[4-(trifluoromethoxy)phenyl]carbamoyl}amino)acetic acid,
- 2-cyclopropyl-2-({[4-(trifluoromethoxy)phenyl]carbamoyl}amino)butanoic acid,
- 2-cyclopropyl-2-({[4-(difluoromethoxy)phenyl]carbamoyl}amino)butanoic acid,
- 2-cyclopropyl-2-[(phenylcarbamoyl)amino]butanoic acid,
- 2-cyclopropyl-2-{[(4-fluorophenyl)carbamoyl]amino}butanoic acid,
- 2-{[(3-cyanophenyl)carbamoyl]amino}-2-cyclopropylbutanoic acid,
- (2R)-2-{[(3-cyanophenyl)carbamoyl]amino}-2-cyclopropylbutanoic acid, and
- (2S)-2-{[(3-cyanophenyl)carbamoyl]amino}-2-cyclopropylbutanoic acid.

17. The method of claim 12, wherein the mammal is a human.

18. The method of claim 13, wherein the compound, or a pharmacologically acceptable salt thereof, selected from the group consisting of:
- dicyclopropyl({[4-(trifluoromethoxy)phenyl]carbamoyl}amino)acetic acid,
- 2-cyclopropyl-2-({[4-(trifluoromethoxy)phenyl]carbamoyl}amino)butanoic acid,
- 2-cyclopropyl-2-({[4-(difluoromethoxy)phenyl]carbamoyl}amino)butanoic acid,
- 2-cyclopropyl-2-[(phenylcarbamoyl)amino]butanoic acid,
- 2-cyclopropyl-2-{[(4-fluorophenyl)carbamoyl]amino}butanoic acid,
- 2-{[(3-cyanophenyl)carbamoyl]amino}-2-cyclopropylbutanoic acid,
- (2R)-2-{[(3-cyanophenyl)carbamoyl]amino}-2-cyclopropylbutanoic acid, and
- (2S)-2-{[(3-cyanophenyl)carbamoyl]amino}-2-cyclopropylbutanoic acid.

19. The method of claim 13, wherein the mammal is a human.

20. The method of claim 14, wherein the compound, or a pharmacologically acceptable salt thereof, selected from the group consisting of:
- dicyclopropyl({[4-(trifluoromethoxy)phenyl]carbamoyl}amino)acetic acid,
- 2-cyclopropyl-2-({[4-(trifluoromethoxy)phenyl]carbamoyl}amino)butanoic acid,
- 2-cyclopropyl-2-({[4-(difluoromethoxy)phenyl]carbamoyl}amino)butanoic acid,
- 2-cyclopropyl-2-[(phenylcarbamoyl)amino]butanoic acid,
- 2-cyclopropyl-2-{[(4-fluorophenyl)carbamoyl]amino}butanoic acid,
- 2-{[(3-cyanophenyl)carbamoyl]amino}-2-cyclopropylbutanoic acid,
- (2R)-2-{[(3-cyanophenyl)carbamoyl]amino}-2-cyclopropylbutanoic acid, and
- (2S)-2-{[(3-cyanophenyl)carbamoyl]amino}-2-cyclopropylbutanoic acid.

21. The method of claim 14, wherein the mammal is a human.

22. The method of claim 15, wherein the compound, or a pharmacologically acceptable salt thereof, selected from the group consisting of:
- dicyclopropyl({[4-(trifluoromethoxy)phenyl]carbamoyl}amino)acetic acid,
- 2-cyclopropyl-2-({[4-(trifluoromethoxy)phenyl]carbamoyl}amino)butanoic acid,
- 2-cyclopropyl-2-({[4-(difluoromethoxy)phenyl]carbamoyl}amino)butanoic acid,
- 2-cyclopropyl-2-[(phenylcarbamoyl)amino]butanoic acid,
- 2-cyclopropyl-2-{[(4-fluorophenyl)carbamoyl]amino}butanoic acid,
- 2-{[(3-cyanophenyl)carbamoyl]amino}-2-cyclopropylbutanoic acid,
- (2R)-2-{[(3-cyanophenyl)carbamoyl]amino}-2-cyclopropylbutanoic acid, and
- (2S)-2-{[(3-cyanophenyl)carbamoyl]amino}-2-cyclopropylbutanoic acid.

23. The method of claim 15, wherein the mammal is a human.

24. A method for reducing indoxyl sulfate in blood, comprising administering, to a mammal, an effective dose of the compound according to the crystal of the compound according to claim 10.

25. The method according to claim 24, wherein the mammal is a human.

\* \* \* \* \*